US008628696B2

(12) United States Patent
Fujdala et al.

(10) Patent No.: US 8,628,696 B2
(45) Date of Patent: Jan. 14, 2014

(54) MOLECULAR PRECURSORS FOR OPTOELECTRONICS

(75) Inventors: Kyle L. Fujdala, San Jose, CA (US);
Wayne A. Chomitz, Oakland, CA (US);
Zhongliang Zhu, San Jose, CA (US);
Matthew C. Kuchta, San Francisco, CA (US)

(73) Assignee: Precursor Energetics, Inc., Santa Clara, CA (US)

( * ) Notice: Subject to any disclaimer, the term of this patent is extended or adjusted under 35 U.S.C. 154(b) by 467 days.

(21) Appl. No.: 12/848,961

(22) Filed: Aug. 2, 2010

(65) Prior Publication Data

US 2011/0146532 A1 Jun. 23, 2011

Related U.S. Application Data

(60) Provisional application No. 61/287,677, filed on Dec. 17, 2009.

(51) Int. Cl.
*H01B 1/12* (2006.01)

(52) U.S. Cl.
USPC .............. 252/519.34; 252/519.14; 252/519.2; 252/519.4; 257/E31.04; 438/95; 427/74; 136/258

(58) Field of Classification Search
USPC ................. 252/519.34, 519.14, 519.2, 519.4; 136/258; 257/E31.04; 438/95; 427/74
See application file for complete search history.

(56) References Cited

U.S. PATENT DOCUMENTS

| | | | |
|---|---|---|---|
| 2,514,981 A | 7/1950 | Walker | |
| 5,436,204 A | 7/1995 | Albin | |
| 5,441,897 A | 8/1995 | Noufi | |
| 5,681,975 A | 10/1997 | Brennan | |
| 5,871,630 A | 2/1999 | Bhattacharya | |
| 5,882,722 A | 3/1999 | Kydd | |
| 5,976,614 A | 11/1999 | Bhattacharya | |
| 5,981,868 A | 11/1999 | Kushiya | |
| 5,985,691 A | 11/1999 | Basol | |
| 6,066,196 A | 5/2000 | Kaloyeros | |
| 6,126,740 A | 10/2000 | Schulz | |
| 6,325,490 B1 | 12/2001 | Yang | |
| 6,368,892 B1 | 4/2002 | Arya | |
| 6,372,538 B1 | 4/2002 | Wendt | |
| 6,500,733 B1 | 12/2002 | Stanbery | |
| 6,518,086 B2 | 2/2003 | Beck | |
| 6,635,307 B2 | 10/2003 | Huang | |
| 6,797,874 B2 | 9/2004 | Stanbery | |
| 6,830,778 B1 | 12/2004 | Schulz | |
| 6,852,920 B2 | 2/2005 | Sager | |
| 6,875,661 B2 | 4/2005 | Mitzi | |
| 6,967,115 B1 | 11/2005 | Sheats | |
| 6,974,976 B2 | 12/2005 | Hollars | |
| 6,987,071 B1 | 1/2006 | Bollman | |
| 6,992,202 B1 | 1/2006 | Banger | |
| 7,026,258 B2 | 4/2006 | Taunier | |
| 7,094,651 B2 | 8/2006 | Mitzi | |
| 7,109,520 B2 | 9/2006 | Yu | |
| 7,179,677 B2 | 2/2007 | Ramanathan | |
| 7,194,197 B1 | 3/2007 | Wendt | |
| 7,235,736 B1 | 6/2007 | Buller | |
| 7,247,346 B1 | 7/2007 | Sager | |
| 7,259,322 B2 | 8/2007 | Gronet | |
| 7,306,823 B2 | 12/2007 | Sager | |
| 7,341,917 B2 | 3/2008 | Milliron | |
| 7,384,680 B2 | 6/2008 | Bi | |
| 7,494,841 B2 | 2/2009 | Mitzi | |
| 7,517,718 B2 | 4/2009 | Mitzi | |
| 7,563,392 B1 | 7/2009 | Hsu | |
| 7,618,841 B2 | 11/2009 | Mitzi | |
| 7,663,057 B2 | 2/2010 | Yu | |
| 8,067,262 B2 * | 11/2011 | Fujdala et al. .................. 438/95 |
| 8,497,390 B2 * | 7/2013 | Fujdala et al. .................. 556/28 |
| 8,512,603 B2 * | 8/2013 | Fujdala et al. ........... 252/519.34 |
| 2003/0123167 A1 | 7/2003 | Kolberg | |
| 2004/0063320 A1 | 4/2004 | Hollars | |
| 2004/0250848 A1 | 12/2004 | Sager | |
| 2005/0121068 A1 | 6/2005 | Sager | |
| 2005/0183767 A1 * | 8/2005 | Yu et al. ........................ 136/263 |
| 2006/0060237 A1 | 3/2006 | Leidholm | |
| 2006/0062902 A1 | 3/2006 | Sager | |
| 2006/0157103 A1 | 7/2006 | Sheats | |
| 2007/0163638 A1 | 7/2007 | Van Duren | |
| 2007/0163640 A1 | 7/2007 | Van Duren | |
| 2007/0163641 A1 | 7/2007 | Van Duren | |
| 2007/0163642 A1 | 7/2007 | Van Duren | |

(Continued)

FOREIGN PATENT DOCUMENTS

EP 0534459 A2 3/1993
JP 5790867 6/1982

(Continued)

OTHER PUBLICATIONS

Eichofer, J. Chem. Soc., Dalton Trans., 2000, 941-944.
Chen, Physical Review B 79, 165211, 1-10 (2009).
Banger, K K et al., Applied Organometallic Chemistry, 2002 ; 16: 617-627.
Banger, K K et al., Inorg Chem, 2003 ; 42(24): 7713-7715.
Chen, Yu et al., Chem Mater, 2007 ; 19: 5256-5261.
Dennler, Gilles et al., Adv Mater, 2009 ; 21: 1323-1338.
Kaelin, M et al., Solar Energy, 2004 ; 77: 749-756.
Kundu, Sambhu N. et al., Thin Solid Films, 2006 ; 515: 2625-2631.
Yoon, Seok Hwan et al., Bull Korean Chem Soc, 2006 ; 27(12): 2071-2073.
Beachley, Organometallics 1996, 15, 3653-3658.
Borisova, Organometallics 2002, 21, 4005-4008.
Deivaraj, Inorg. Chem. 2002, 41, 3755-3760.

(Continued)

*Primary Examiner* — Douglas McGinty
(74) *Attorney, Agent, or Firm* — Eckman Basu LLP

(57) ABSTRACT

This invention relates to compounds and compositions used to prepare semiconductor and optoelectronic materials and devices. This invention provides a range of compounds, compositions, materials and methods directed ultimately toward photovoltaic applications, as well as devices and systems for energy conversion, including solar cells. In particular, this invention relates to molecular precursor compounds and precursor materials for preparing photovoltaic layers.

20 Claims, 18 Drawing Sheets

(56) References Cited

U.S. PATENT DOCUMENTS

| | | | |
|---|---|---|---|
| 2007/0163643 | A1 | 7/2007 | Van Duren |
| 2007/0163644 | A1 | 7/2007 | Van Duren |
| 2007/0169812 | A1* | 7/2007 | Robinson et al. ............. 136/262 |
| 2007/0169813 | A1 | 7/2007 | Robinson |
| 2007/0178620 | A1 | 8/2007 | Basol |
| 2007/0207565 | A1 | 9/2007 | Kodas |
| 2007/0264488 | A1 | 11/2007 | Lee |
| 2008/0057203 | A1 | 3/2008 | Robinson |
| 2008/0057616 | A1 | 3/2008 | Robinson |
| 2008/0124833 | A1 | 5/2008 | Ruiz |
| 2008/0135099 | A1 | 6/2008 | Yu |
| 2008/0135811 | A1 | 6/2008 | Yu |
| 2008/0135812 | A1 | 6/2008 | Yu |
| 2008/0138501 | A1 | 6/2008 | Yu |
| 2008/0142072 | A1 | 6/2008 | Yu |
| 2008/0142080 | A1 | 6/2008 | Yu |
| 2008/0142081 | A1 | 6/2008 | Yu |
| 2008/0142082 | A1 | 6/2008 | Yu |
| 2008/0142083 | A1 | 6/2008 | Yu |
| 2008/0142084 | A1 | 6/2008 | Yu |
| 2008/0145633 | A1 | 6/2008 | Kodas |
| 2008/0149176 | A1 | 6/2008 | Sager |
| 2008/0175982 | A1 | 7/2008 | Robinson |
| 2008/0213467 | A1 | 9/2008 | Yu |
| 2008/0257201 | A1 | 10/2008 | Harris |
| 2009/0169723 | A1 | 7/2009 | Hanket |
| 2009/0253227 | A1 | 10/2009 | Defries |
| 2009/0260670 | A1 | 10/2009 | Li |
| 2009/0280598 | A1 | 11/2009 | Curtis |
| 2009/0280624 | A1 | 11/2009 | Curtis |
| 2010/0029036 | A1 | 2/2010 | Robinson |
| 2010/0291758 | A1 | 11/2010 | Robinson |
| 2011/0030795 | A1* | 2/2011 | Fujdala et al. ................ 136/262 |
| 2013/0125988 | A1* | 5/2013 | Cao et al. ...................... 136/264 |

FOREIGN PATENT DOCUMENTS

| | | |
|---|---|---|
| JP | 10-273783 A | 10/1998 |
| JP | 2000-058893 A | 2/2000 |
| JP | 200283824 | 3/2002 |
| JP | 2008056511 | 8/2006 |
| JP | 2008-56511 A | 3/2008 |
| KR | 10-2009-0029495 A | 3/2009 |
| KR | 10-2009-0050558 A | 5/2009 |
| WO | WO9304212 A1 | 3/1993 |
| WO | WO2007082080 A1 | 7/2007 |
| WO | WO2008057119 A1 | 5/2008 |
| WO | WO2008063190 A2 | 5/2008 |
| WO | WO2008104087 A1 | 9/2008 |

OTHER PUBLICATIONS

Deivaraj, Chem. Mater. 2003, 15, 2383-2391.
Kuckmann, Inorg. Chem. 2005, 44, 3449-3458.
Lazell, Chem. Mater. 1999, 11, 3430-3432.
Malik, Chem. Mater. 2001, 13, 913-920.
McAleese, Chem. Vap. Deposition 1998, 4, No. 3, 94-96.
Nguyen, Chem. Commun., 2006, 2182-2184.
Nomura, Polyhedron 1989, vol. 8, No. 15, 1891-1896.
Nomura, J. Mater. Chem., 1992,2(7), 765-766.
Stoll, Chem. Mater. 1998, 10, 650-657.
Tian, Inorg. Chem. 2006, 45, 8258-8263.
Tran, Organometallics 2000, 19, 5202-5208.
Wallbank, Organometallics 2005, 24, 788-790.
Kumar, J. Chem. Soc. Dalton Trans. 1988, p. 1045-1047, Reactions of Some Main Group Metals with Diphenyl Disulphide and Diphenyl Diselenide.
Green, Inorg. Chem. 1989, V28, 123-127.
Nomura, Polyhedron vol. 9, No. 2/3, pp. 361-366, 1990.
Nomura, Applied Organometallic Chemistry, vol. 6, 685-691 (1992).
Hirpo, J. Am. Chem. Soc. 1993, V115, 1597-1599.
Ohlmann, J. Chem. Soc., Chem. Commun., 1995, p. 1011-1012.
Beck, Thin Solid Films 272 ( 1996) 71-82.
Grigsby, J. Chem. Soc., Dalton Trans., 1998, pp. 2547-2556.
Suh, Inorg. Chem. 1999, 38, 1627-1633.
Banger, Chem. Mater. 2001, 13, 3827-3829.
Deivaraj, Chem. Commun., 2001, 2304-2305.
Kapur, Thin Solid Films 431-432 (2003) 53-57.
Ahlrichs, Eur. J. Inorg. Chem. 2006, 345-350.
Milliron, Chem. Mater., vol. 18, No. 3, 2006, p. 587-590.
Vittal, Acc. Chem. Res. 2006, 39, 869-877.
Yamada, Science and Technology of Advanced Materials 7 (2006) 42-45.
Borecki, Inorg. Chem. 2007, 46, 2478-2484.
Schneider, Chem. Mater. 2007, 19, 2780-2785.
Merdes, Thin Solid Films 516 (2008) 7335-7339.
Panthani, J. Am. Chem. Soc. 2008, 130, 16770-16777.
Hepp, Solution Processing of Inorganic Materials, edited by David Mitzi, 2009, Chapter 6, p. 157-198.
Hou, Thin Solid Films (2009) pp. 1-4, Low-temperature processing of a solution-deposited CuInSSe thin-film solar cell.
Malik, J. Mater. Res., vol. 24, No. 4, Apr. 2009, p. 1375-1387.
Mitzi, Thin Solid Films 517 (2009) 2158-2162.
Park, Journal ofCrystalGrowth 311 (2009) 2621-2625.
Dwyer, Solar Energy Materials & Solar Cells 94 (2010) 598-605.
Hibberd, Prog. Photovolt: Res. Appl. 2010; 18:434-452.
Niki, Prog. Photovolt: Res. Appl. 2010; 18:453-466.
Yuan, Chem. Mater. 2010,22,285-287.

* cited by examiner

MOLECULAR PRECURSORS FOR OPTOELECTRONICS

CROSS REFERENCE TO RELATED APPLICATIONS

This application claims the benefit of U.S. Provisional Application No. 61/287,677, filed Dec. 17, 2009, which is hereby incorporated by reference in its entirety.

BACKGROUND

The development of photovoltaic devices such as solar cells is important for providing a renewable source of energy and many other uses. The demand for power is ever-rising as the human population increases. In many geographic areas, solar cells may be the only way to meet the demand for power. The total energy from solar light impinging on the earth for one hour is about $4 \times 10^{20}$ joules. It has been estimated that one hour of total solar energy is as much energy as is used worldwide for an entire year. Thus, billions of square meters of efficient solar cell devices will be needed.

Photovoltaic devices are made by a variety of processes in which layers of semiconducting material are created on a substrate. Layers of additional materials are used to protect the photovoltaic semiconductor layers and to conduct electrical energy out of the device. Thus, the usefulness of an optoelectronic or solar cell product is in general limited by the nature and quality of the photovoltaic layers.

For example, one way to produce a solar cell product involves depositing a thin, light-absorbing, solid layer of the material copper indium gallium diselenide, known as "CIGS," on a substrate. A solar cell having a thin film CIGS layer can provide low to moderate efficiency for conversion of sunlight to electricity. The CIGS layer can be made by processing at relatively high temperatures several elemental sources containing the atoms needed for CIGS. In general, CIGS materials are complex, having many possible solid phases.

The CIGS elemental sources must be formed or deposited, either individually or as a mixture, in a thin, uniform layer on the substrate. For example, deposition of the CIGS sources can be done as a co-deposition, or as a multistep deposition. The difficulties with these approaches include lack of uniformity of the CIGS layers, such as the appearance of different solid phases, imperfections in crystalline particles, voids, cracks, and other defects in the layers. Another problem in some processes is the inability to precisely control the stoichiometric ratios of the metal atoms in the layers.

For example, some methods for solar cells are disclosed in U.S. Pat. Nos. 5,441,897, 5,976,614, 6,518,086, 5,436,204, 5,981,868, 7,179,677, 7,259,322, U.S. Patent Publication No. 2009/0280598, and PCT International Application Publication Nos. WO2008057119 and WO2008063190.

A further difficulty is the need to heat the substrate to high temperatures to finish the film. This can cause unwanted defects due to rapid chemical or physical transformation of the layers. High temperatures may also limit the nature of the substrate that can be used. For example, it is desirable to make thin film photovoltaic layers on a flexible substrate such as a polymer or plastic that can be formed into a roll for processing and installation on a building or outdoor structure. Polymer substrates may not be compatible with the high temperatures needed to process the semiconductor layers. Preparing thin film photovoltaic layers on a flexible substrate is an important goal for providing renewable solar energy and developing new generations of electro-optical products.

Moreover, methods for large scale manufacturing of solar cells can be difficult because of the chemical processes involved. In general, large scale processes for solar cells are unpredictable because of the difficulty in controlling numerous chemical and physical parameters involved in forming an absorber layer of suitable quality on a substrate, as well as forming the other layers required to make an efficient solar cell and provide electrical conductivity.

What is needed are compounds and compositions to produce materials for photovoltaic layers, especially thin film layers for solar cell devices and other products.

BRIEF SUMMARY

This invention relates to compounds and compositions used to prepare semiconductor and optoelectronic materials and devices including thin film and band gap materials. This invention provides a range of compounds, compositions, materials and methods directed ultimately toward photovoltaic applications and other semiconductor materials, as well as devices and systems for energy conversion, including solar cells. In particular, this invention relates to novel processes, compounds and materials for preparing semiconductor materials.

This invention provides compounds, compositions, materials and methods for preparing semiconductors and materials, as well as optoelectronic devices and photovoltaic layers. Among other things, this disclosure provides precursor molecules and compositions for making and using semiconductors such as for photovoltaic layers, solar cells and other uses.

In various embodiments of this invention, chemically and physically uniform semiconductor layers can be prepared with the molecular precursor compounds described herein.

In further embodiments, solar cells and other products can be made in processes operating at relatively low temperatures with the compounds and compositions of this disclosure.

The molecular precursor compounds and compositions of this disclosure can provide enhanced processability for solar cell production, and the ability to be processed on a variety of substrates including polymers at relatively low temperatures.

The advantages provided by the compounds, compositions, and materials of this invention in making photovoltaic layers and other semiconductors and devices are generally obtained regardless of the morphology or architecture of the semiconductors or devices.

In some embodiments, this invention provides compounds comprising the formula $M^A$-$(ER^1)(ER^2)(ER^3)M^BR^4$, wherein $M^A$ is a monovalent metal atom, $M^B$ is an atom of Group 13, each E is independently S, Se, or Te, and $R^1$, $R^2$, $R^3$, and $R^4$ are the same or different and are independently selected from alkyl, aryl, heteroaryl, alkenyl, amido, silyl, and inorganic and organic ligands. $M^A$ may be Cu or Ag, and $M^B$ may be Ga or In. Each of $R^1$, $R^2$, $R^3$ and $R^4$ can be independently (C1-12)alkyl, or (C1-4)alkyl.

In certain embodiments, a compound may be a dimer having the formula $(M^A$-$(ER^1)(ER^2)(ER^3)M^BR^4)_2$.

In further embodiments, a compound can have the formula $(M^{A1}$-$(ER^1)(ER^2)(ER^3)M^BR^4)(M^{A2}$-$(ER^1)(ER^2)(ER^3)M^BR^4)$, wherein $M^{A1}$ and $M^{A2}$ are different monovalent metal atoms.

In certain embodiments, $M^A$ is a divalent metal atom, and the formula is Z-$M^A$-$(ER^1)(ER^2)(ER^3)M^BR^4$, wherein Z is selected from alkyl, aryl, heteroaryl, alkenyl, amido, silyl, and inorganic and organic ligands.

In additional embodiments, $(ER^1)$ is $(ER^1Z)$, and the formula is $M^A(ER^1Z)(ER^2)(ER^3)M^BR^4$, wherein Z is attached to $M^A$ and Z is a neutral moiety selected from —NR$_2$, —PR$_2$, —AsR$_2$, -ER, —SR, —OR, and —SeR, where R is alkyl or aryl.

In some aspects, $M^A$ is a divalent metal atom, (ER$^1$) is (ER$^1$Z), and the formula is $M^A$(ER$^1$Z)(ER$^2$)(ER$^3$)M$^B$R$^4$, wherein Z is attached to $M^A$ and Z is an anionic moiety selected from —NR$_2$, -E$^-$, —O$^-$, —R$^-$, -ERNR$^-$, -ERE$^-$, and —SiR$_2^-$, where R is alkyl or aryl.

Embodiments of this invention may further provide an ink comprising one or more compounds above and one or more carriers. The ink can be a solution of the compounds in an organic carrier, or a slurry or suspension. An ink may further contain one or more components selected from the group of a surfactant, a dispersant, an emulsifier, an anti-foaming agent, a dryer, a filler, a resin binder, a thickener, a viscosity modifier, an anti-oxidant, a flow agent, a plasticizer, a conductivity agent, a crystallization promoter, an extender, a film conditioner, an adhesion promoter, and a dye.

In some aspects, this invention provides methods for making a molecular precursor compound having the formula $M^A$-(ER$^2$)(ER$^3$)(ER$^4$)M$^B$R$^1$, comprising: a) providing a first compound R$^1_2$M$^B$ER$^2$; and b) contacting the first compound with a second compound $M^A$(ER$^3$) in the presence of a third compound HER$^4$; wherein M$^B$ is a Group 13 atom, $M^A$ is a monovalent metal atom, each E is independently for each occurrence S, Se, or Te, and R$^1$, R$^2$, R$^3$ and R$^4$ are the same or each different and are independently selected from alkyl, aryl, heteroaryl, alkenyl, amido, silyl, and inorganic and organic ligands. The first, second and third compounds can be contacted in a process of depositing, spraying, coating, or printing. The first, second and third compounds can be contacted at a temperature of from about −60° C. to about 100° C.

In some variations, this disclosure provides an article comprising one or more compounds or inks above deposited onto a substrate. The depositing can be done by spraying, spray coating, spray deposition, spray pyrolysis, printing, screen printing, inkjet printing, aerosol jet printing, ink printing, jet printing, stamp/pad printing, transfer printing, pad printing, flexographic printing, gravure printing, contact printing, reverse printing, thermal printing, lithography, electrophotographic printing, electrodepositing, electroplating, electroless plating, bath deposition, coating, dip coating, wet coating, spin coating, knife coating, roller coating, rod coating, slot die coating, meyerbar coating, lip direct coating, capillary coating, liquid deposition, solution deposition, layer-by-layer deposition, spin casting, solution casting, and combinations of any of the forgoing.

A substrate may be selected from a semiconductor, a doped semiconductor, silicon, gallium arsenide, insulators, glass, molybdenum glass, silicon dioxide, titanium dioxide, zinc oxide, silicon nitride, a metal, a metal foil, molybdenum, aluminum, beryllium, cadmium, cerium, chromium, cobalt, copper, gallium, gold, lead, manganese, molybdenum, nickel, palladium, platinum, rhenium, rhodium, silver, stainless steel, steel, iron, strontium, tin, titanium, tungsten, zinc, zirconium, a metal alloy, a metal silicide, a metal carbide, a polymer, a plastic, a conductive polymer, a copolymer, a polymer blend, a polyethylene terephthalate, a polycarbonate, a polyester, a polyester film, a mylar, a polyvinyl fluoride, polyvinylidene fluoride, a polyethylene, a polyetherimide, a polyethersulfone, a polyetherketone, a polyimide, a polyvinylchloride, an acrylonitrile butadiene styrene polymer, a silicone, an epoxy, paper, coated paper, and combinations of any of the forgoing. A substrate may be a shaped substrate including a tube, a cylinder, a roller, a rod, a pin, a shaft, a plane, a plate, a blade, a vane, a curved surface or a spheroid.

This invention further includes methods for making an article, the method comprising: (a) providing one or more compounds or inks; (b) providing a substrate; and (c) depositing the compounds or inks onto the substrate. Step (c) can be repeated. The method can include heating the substrate at a temperature of from about 100° C. to about 400° C. to convert the compounds or inks to a material. The method can include heating the substrate at a temperature of from about 100° C. to about 400° C. to convert the compounds or inks to a material, followed by repeating step (c). The method can include annealing the material by heating the substrate at a temperature of from about 300° C. to about 650° C. The method may include heating the substrate at a temperature of from about 100° C. to about 400° C. to convert the compounds or inks to a material, and annealing the material by heating the substrate at a temperature of from about 300° C. to about 650° C.

In certain variations, the method can include heating the substrate at a temperature of from about 100° C. to about 400° C. to convert the compounds or inks to a material, depositing the compounds or inks onto the substrate, and annealing the material by heating the substrate at a temperature of from about 300° C. to about 650° C. The method may include (d) heating the substrate at a temperature of from about 100° C. to about 400° C. to convert the compounds or inks to a material; (e) depositing the compounds or inks onto the substrate; (f) repeating steps (d) and (e); and (g) annealing the material by heating the substrate at a temperature of from about 300° C. to about 650° C. In certain embodiments, the method includes (d) heating the substrate at a temperature of from about 100° C. to about 400° C. to convert the compounds or inks to a material; (e) annealing the material by heating the substrate at a temperature of from about 300° C. to about 650° C.; and (f) repeating steps (c), (d) and (e). In further embodiments, the method can include an optional step of selenization or sulfurization, either before, during or after any step of heating or annealing.

Embodiments of this disclosure include methods for making a material comprising, (a) providing one or more compounds or inks above; (b) providing a substrate; (c) depositing the compounds or inks onto the substrate; and (d) heating the substrate at a temperature of from about 20° C. to about 650° C. in an inert atmosphere, thereby producing a material.

This invention includes a thin film material made by a process comprising, (a) providing one or more compounds or inks above;

(b) providing a substrate;

(c) depositing the compounds or inks onto the substrate; and (d) heating the substrate at a temperature of from about 20° C. to about 650° C. in an inert atmosphere, thereby producing a thin film material having a thickness of from 0.05 to 10 micrometers.

In some aspects, this invention includes methods for making a photovoltaic absorber layer on a substrate comprising, (a) providing one or more compounds or inks above;

(b) providing a substrate;

(c) depositing the compounds or inks onto the substrate; and (d) heating the substrate at a temperature of from about 100° C. to about 650° C. in an inert atmosphere, thereby producing a photovoltaic absorber layer having a thickness of from 0.001 to 100 micrometers.

Embodiments of this invention further include a photovoltaic device comprising precursor or material above, and a photovoltaic system for providing electrical power comprising a photovoltaic device, as well as methods for providing electrical power comprising using a photovoltaic system to convert light into electrical energy.

This brief summary, taken along with the detailed description of the invention, as well as the figures, the appended examples and claims, as a whole, encompass the disclosure of the invention.

BRIEF DESCRIPTION OF THE DRAWINGS

FIG. 1 shows an embodiment of a family of molecular precursor compounds MP1. As shown in FIG. 1, the structure of these molecular precursor compounds can be represented by the formula $M^A$-$(ER^2)(ER^3)(ER^4)M^BR^1$, where E is a chalcogen, $M^A$ is a monovalent metal atom and $M^B$ is an atom of Group 13. The molecular structure of the family of compounds is of a dimer, represented by the formula $(M^A$-$(ER^2)(ER^3)(ER^4)M^BR^1)_2$. $M^A$ is stabilized by interactions with one or more chalcogen atoms of the ligands $(ER^2)$, $(ER^3)$, and $(ER^4)$. $M^B$ is stabilized by having four ligands attached.

FIG. 2 shows an embodiment of a family of molecular precursor compounds MP2. As shown in FIG. 2, the structure of these molecular precursor compounds is represented by the formula $(R^1M^{B1}(ER^2)(ER^3)(ER^4)$-$M^{A1})$ $(M^{A2}$-$(ER^5)(ER^6)(ER^7)M^{B2}R^8)$, where E is a chalcogen, $M^{A1}$ and $M^{A2}$ are the same or different monovalent metal atoms, and $M^{B1}$ and $M^{B2}$ are different atoms of Group 13. $M^{A1}$ and $M^{A2}$ are stabilized by interactions with chalcogen atoms of three of the ligands $(ER^n)$. $M^{B1}$ and $M^{B2}$ are stabilized by having four ligands attached.

FIG. 3 shows an embodiment of a family of molecular precursor compounds MP3. As shown in FIG. 3, the structure of these molecular precursor compounds is represented by the formula $(R^4E)M^A(ER^3)(ER^5)(ER^2)M^BR^1$, where E is a chalcogen, $M^A$ is a divalent metal atom, and $M^B$ is an atom of Group 13. $M^A$ is stabilized by having chalcogen-containing ligands attached. $M^B$ is stabilized by having four ligands attached.

FIG. 4 shows an embodiment of a family of molecular precursor compounds MP3. As shown in FIG. 4, the structure of these molecular precursor compounds is represented by the formula $R^5M^A(ER^4)(ER^3)(ER^2)M^BR^1$, where E is a chalcogen, $M^A$ is a divalent metal atom, and $M^B$ is an atom of Group 13. $M^A$ is stabilized by having ligands attached. $M^B$ is stabilized by having ligands attached.

FIG. 5 shows an embodiment of a family of molecular precursor compounds MP4. As shown in FIG. 5, the structure of these molecular precursor compounds is represented by the formula $M^A(ER^2Z)(ER^3)(ER^2)M^BR^1$, where E is a chalcogen, $M^A$ is a metal atom, and $M^B$ is an atom of Group 13. $M^A$ is stabilized by having ligands attached, including Z which is a neutral or anionic moiety attached to $M^A$. $M^B$ is stabilized by having four ligands attached.

FIG. 8 shows the structure of an embodiment of a molecular precursor compound (MP1) as determined by single crystal X-ray diffraction. As shown in FIG. 8, the molecular structure of this compound is represented by the formula $(Cu-(S^tBu)_3In^nBu)_2$.

FIG. 9 shows the transition of a molecular precursor embodiment (MP1) of this invention into a material as determined by thermogravimetric analysis. As shown in FIG. 9, the molecular structure of the precursor compound is represented by the formula $(Cu-(S^tBu)_3In^tBu)_2$. The transition of the precursor compound into the material $CuInS_2$ takes place sharply and is completed at a temperature of about 240° C.

FIG. 10 shows the transition of a molecular precursor embodiment (MP1) of this invention into a material as determined by thermogravimetric analysis. As shown in FIG. 10, the molecular structure of the precursor compound is represented by the formula $(Cu-(Se^tBu)_3Ga^tBu)_2$. The transition of the precursor compound into the material $CuGaSe_2$ takes place sharply and is completed at a temperature of about 210° C.

FIG. 11 shows the transition of a molecular precursor embodiment (MP1) of this invention into a material as determined by thermogravimetric analysis. As shown in FIG. 11, the molecular structure of the precursor compound is represented by the formula $(Cu-(S^tBu)_3Ga^tBu)_2$. The transition of the precursor compound into the material $CuGaS_2$ takes place sharply and is completed at a temperature of about 225° C.

FIG. 12 shows the transition of a molecular precursor embodiment (MP1) of this invention into a material as determined by thermogravimetric analysis. As shown in FIG. 12, the molecular structure of the precursor compound is represented by the formula $(Cu-(Se^tBu)_3In^tBu)_2$. The transition of the precursor compound into the material $CuInSe_2$ takes place sharply and is completed at a temperature of about 192° C.

FIG. 13 shows the transition of a mixture of molecular precursor embodiments (MP1) of this invention into a material as determined by thermogravimetric analysis. As shown in FIG. 13, the molecular structures of the precursor compounds are represented by the formulas $(Cu-(Se^tBu)_3In^tBu)_2$ and $(Cu-(Se^tBu)_3Ga^tBu)_2$. The transition of the precursor compounds into the material $CuIn_{0.75}Ga_{0.25}Se_2$ takes place sharply and is completed at a temperature of about 195° C.

FIG. 14 shows the transition of a molecular precursor embodiment (MP1-Ag) of this invention into a material as determined by thermogravimetric analysis. As shown in FIG. 14, the molecular structure of the precursor compound is represented by the formula $(Ag-(Se^tBu)_3In^nBu)_2$. The transition of the precursor compound into the material $AgInSe_2$ is completed at a temperature of about 205° C.

FIG. 15 shows the transition of a molecular precursor embodiment (MP1-Ag) of this invention into a material as determined by thermogravimetric analysis. As shown in FIG. 15, the molecular structure of the precursor compound is represented by the formula $(Ag-(Se^tBu)_3Ga^nBu)_2$. The transition of the precursor compound into the material $AgGaSe_2$ is completed at a temperature of about 210° C.

FIG. 16 shows the transition of a molecular precursor embodiment (MP1-Ag) of this invention into a material as determined by thermogravimetric analysis. As shown in FIG. 16, the molecular structure of the precursor compound is represented by the formula $(Ag-(Se^tBu)_3In^sBu)_2$. The transition of the precursor compound into the material $AgInSe_2$ is completed at a temperature of about 195° C.

FIG. 17 shows the transition of a molecular precursor embodiment (MP1-Ag) of this invention into a material as determined by thermogravimetric analysis. As shown in FIG. 17, the molecular structure of the precursor compound is represented by the formula $(Ag-(Se^tBu)_3Ga^sBu)_2$.

The transition of the precursor compound into the material AgGaSe$_2$ is completed at a temperature of about 195° C.

Figure 18:
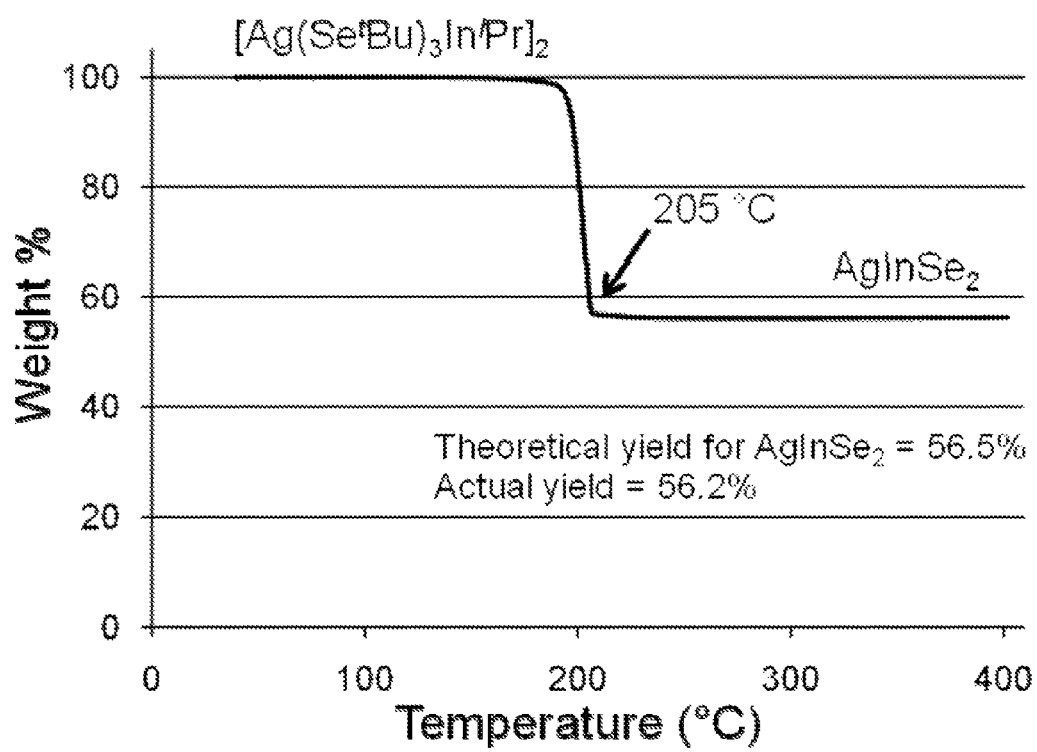

FIG. 18: FIG. 18 shows the transition of a molecular precursor embodiment (MP1-Ag) of this invention into a material as determined by thermogravimetric analysis. As shown in FIG. 18, the molecular structure of the precursor compound is represented by the formula (Ag—(Se$^t$Bu)$_3$In$^i$Pr)$_2$. The transition of the precursor compound into the material AgInSe$_2$ is completed at a temperature of about 205° C.

DETAILED DESCRIPTION

This disclosure provides a range of novel compounds, compositions, materials and methods for semiconductor and optoelectronic materials and devices including thin film photovoltaics and various semiconductor band gap materials.

This invention provides compounds and compositions for photovoltaic applications, as well as for devices and systems for energy conversion, including solar cells.

The compounds and compositions of this disclosure include molecular precursor compounds and precursors for materials for preparing novel semiconductor and photovoltaic materials, films, and products. Among other advantages, this disclosure provides stable molecular precursor compounds for making and using layered materials and photovoltaics, such as for solar cells and other uses.

In general, the structure and properties of the compounds, compositions, and materials of this invention provide advantages in making photovoltaic layers, semiconductors, and devices regardless of the morphology, architecture, or manner of fabrication of the semiconductors or devices.

The molecular precursor compounds of this invention are desirable for preparing semiconductor materials and compositions. A molecular precursor has a structure containing two or more different metal atoms which may be bound to each other through interactions or bridges with one or more chalcogen atoms of chalcogen-containing moieties.

With this structure, when a molecular precursor is used in a process such as deposition, coating or printing on a substrate or surface, as well as processes involving annealing, sintering, thermal pyrolysis, and other semiconductor manufacturing processes, use of the molecular precursors can enhance the formation of a semiconductor and its properties.

For example, the use of a molecular precursor in semiconductor manufacturing processes can enhance the formation of M-E-M' bonding, such as is required for chalcogen-containing semiconductor compounds and materials, where M is an atom of one of Groups 3 to 12, M' is an atom of Group 13, and E is a chalcogen.

In aspects of this invention, chemically and physically uniform semiconductor layers can be prepared with molecular precursor compounds.

In further embodiments, solar cells and other products can be made in processes operating at relatively low temperatures using the precursor compounds and compositions of this disclosure.

The molecular precursors of this disclosure are useful to prepare inks that can be used in various methods to prepare semiconductor materials.

The molecular precursor compounds and compositions of this disclosure can provide enhanced processability for solar cell production.

Certain molecular precursor compounds and compositions of this disclosure provide the ability to be processed at relatively low temperatures, as well as the ability to use a variety of substrates including flexible polymers in solar cells.

Empirical Formulas of Molecular Precursors

This disclosure provides a range of molecular precursor compounds having two or more different metal atoms and one or more chalcogen atoms.

In certain aspects, a molecular precursor compound may contain one or more metal atoms, and one or more atoms of Group 13, as well as combinations thereof. Any of these atoms may be bonded to one or more atoms selected from atoms of Group 15, S, Se, and Te, as well as one or more ligands. A molecular precursor compound may be a neutral compound, or an ionic form, or have a charged complex or counterion.

A molecular precursor compound may contain one or more atoms selected from the transition metals of Group 3 through Group 12, B, Al, Ga, In, Tl, Si, Ge, Sn, Pb, and Bi. Any of these atoms may be bonded to one or more atoms selected from atoms of Group 15, S, Se, and Te, as well as one or more ligands.

A molecular precursor compound may contain one or more atoms selected from Ni, Pd, Pt, Cu, Ag, Au, Zn, Cd, Hg, B, Al, Ga, In, Tl, Si, Ge, Sn, Pb, and Bi. Any of these atoms may be bonded to one or more atoms selected from atoms of Group 15, S, Se, and Te, as well as one or more ligands.

In some embodiments, a molecular precursor compound may contain one or more atoms selected from Cu, Ag, Zn, Ga, In, Tl, Si, Ge, Sn, and Pb. Any of these atoms may be bonded to one or more atoms selected from atoms of Group 15, S, Se, and Te, as well as one or more ligands.

In some embodiments, a molecular precursor compound may contain one or more atoms selected from Cu, Ag, Zn, Ga, In, Tl, Si, Ge, Sn, and Pb. Any of these atoms may be bonded to one or more chalcogen atoms, as well as one or more ligands.

In some variations, a molecular precursor compound may contain one or more atoms selected from Cu, Ag, Ga, and In. Any of these atoms may be bonded to one or more atoms selected from S, Se, and Te, as well as one or more ligands.

Precursor Molecular Structure and Properties

A molecular precursor compound of this disclosure is stable at ambient temperatures. Molecular precursors can be used for making layered materials, optoelectronic materials, and devices. Using molecular precursors advantageously allows control of the stoichiometry, structure, and ratios of various atoms in a material, layer, or semiconductor.

Molecular precursor compounds of this invention may be solids, solids with low melting temperatures, oily substances, or liquids at ambient temperatures. Embodiments of this disclosure that are fluids at ambient temperatures can provide superior processability for production of solar cells and other products, as well as the enhanced ability to be processed on a variety of substrates including flexible substrates.

In general, a molecular precursor compound can be processed through the application of heat, light, kinetic, mechanical or other energy to be converted to a material, including a semiconductor material. In these processes, a molecular precursor compound undergoes a transition to become a material. The conversion of a molecular precursor compound to a material can be done in processes known in the art, as well as the novel processes of this disclosure.

Embodiments of this invention may further provide processes for making optoelectronic materials. Following the synthesis of a molecular precursor compound, the compound can be deposited, sprayed, or printed onto a substrate by various means. Conversion of the molecular precursor compound to a material can be done during or after the process of depositing, spraying, or printing the compound onto the substrate.

A molecular precursor compound of this disclosure may have a transition temperature below about 400° C., or below about 300° C., or below about 280° C., or below about 260° C., or below about 240° C., or below about 220° C., or below about 200° C.

In some aspects, molecular precursors of this disclosure include molecules that are fluid or liquid at relatively low temperatures and can be processed as a neat liquid. In certain embodiments, a molecular precursor has a liquid state at a temperature below about 200° C., or below about 180° C., or below about 160° C., or below about 140° C., or below about 120° C., or below about 100° C., or below about 80° C., or below about 60° C., or below about 40° C.

A molecular precursor compound of this invention can be crystalline or amorphous, and can be soluble in various non-aqueous solvents.

A molecular precursor compound may contain ligands, or ligand fragments, or portions of ligands that can be removed under mild conditions, at relatively low temperatures, and therefore provide a facile route to convert the molecular precursor to a material or semiconductor. The ligands, or some atoms of the ligands, may be removable in various processes, including certain methods for depositing, spraying, and printing, as well as by application of energy.

These advantageous features allow enhanced control over the structure of a semiconductor material made with the molecular precursor compounds of this invention.

Molecular Precursors (MP1) for Semiconductors and Optoelectronics

In some embodiments, a molecular precursor compound of the family MP1 contains an atom $M^B$ of Group 13 selected from Al, Ga, and In, which is stabilized by having ligands attached. These molecular precursor compounds further contain a monovalent metal atom $M^A$ selected from Cu, Au, Ag, and Hg, which is stabilized by interactions with one or more chalcogen atoms. The atom $M^A$ may further be stabilized by interacting with another $M^A$ atom. Aside from interactions with chalcogen atoms, the atom $M^A$ has no other ligands attached.

Figure 1:
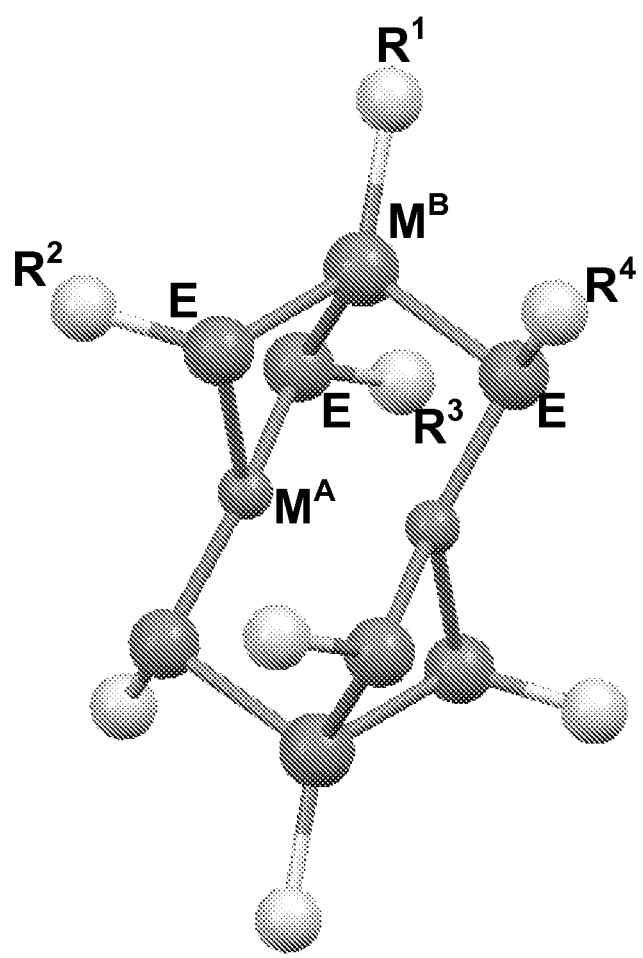
FIG. 1.

The structure of a family of MP1 precursor molecules represented by the formula $M^A\text{-}(ER^2)(ER^3)(ER^4)M^BR^1$ is shown in FIG. 1.

The molecular structure of the family of compounds is of a dimer, represented by the formula $(M^A\text{-}(ER^2)(ER^3)(ER^4)M^BR^1)_2$.

The local structure surrounding the atom $M^B$ in a molecule of the MP1 family is a tetrahedral arrangement of four atoms. At one apex of the $M^B$ tetrahedron is an atom of $R^1$ through which it is attached to $M^B$. The remainder of the tetrahedron is formed by the chalcogen atoms of three of the ligands $(ER^2)$, $(ER^3)$, and $(ER^4)$, each of which is attached through a chalcogen atom to $M^B$.

The local structure surrounding the atom $M^A$ includes bonding interactions with three chalcogen atoms that belong to three of the ligands $(ER^2)$, $(ER^3)$, and $(ER^4)$. The three ligands $(ER^2)$, $(ER^3)$, and $(ER^4)$, are chalcogen bridging ligands that are each shared through bonding of their chalcogen atom to an $M^A$ atom and an $M^B$ atom. The atom $M^A$ may further be stabilized by interacting with another $M^A$ atom. Aside from interactions with chalcogen atoms, the atom $M^A$ has no other ligands attached.

The portion $R^n$, where n is 1, 2, 3, or 4, of each of the ligands attached to the atoms $M^A$ and $M^B$ may be a good leaving group in relation to a transition of the molecular precursor compound at elevated temperatures or upon application of energy.

The arrangement of atoms in a molecular precursor compound of the MP1 family may be described by the formula $M^A\text{-}(ER^2)(ER^3)(ER^4)M^BR^1$, wherein E is chalcogen, and $R^1$, $R^2$, $R^3$, and $R^4$ are the same or different and are groups attached through a carbon or non-carbon atom, including alkyl, aryl, heteroaryl, alkenyl, amido, silyl, and inorganic and organic ligands. In some embodiments, $R^1$, $R^2$, $R^3$, and $R^4$ are the same or different and are alkyl groups attached through a carbon atom.

In some embodiments, molecular precursor compounds of the MP1 family advantageously do not contain a phosphine ligand, or a ligand or attached compound containing phosphorus, arsenic, or antimony, or a halogen ligand.

Embodiments of this invention further provide a family MP1 of molecular precursor compounds in which the arrangement of atoms may be described by the formula $Cu\text{-}(ER^2)(ER^3)(ER^4)(In,Ga)R^1$, wherein E is chalcogen, and $R^1$, $R^2$, $R^3$, and $R^4$ are the same or different and are groups attached through a carbon or non-carbon atom, including alkyl, aryl, heteroaryl, alkenyl, amido, silyl, and inorganic and organic ligands. In some embodiments, $R^1$, $R^2$, $R^3$, and $R^4$ are the same or different and are alkyl groups attached through a carbon atom.

In certain variations, a molecular precursor compound of the MP1 family contains an atom $M^B$, being In or Ga, which is stabilized by attached ligands. These molecular precursor compounds further contain an atom $M^A$, being Cu, which is stabilized by interactions with one or more chalcogen atoms. The atom $M^A$ may further be stabilized by interacting with another $M^A$ atom. Aside from interactions with chalcogen atoms, the atom $M^A$ has no other ligands attached.

In additional aspects, a molecular precursor compound may have the formula $(M^{A1}\text{-}(ER^1)(ER^2)(ER^3)M^BR^4)(M^{A2}\text{-}(ER^1)(ER^2)(ER^3)M^BR^4)$, wherein $M^{A1}$ and $M^{A2}$ are different atoms defined as for $M^A$.

In further embodiments, the groups $R^1$, $R^2$, $R^3$, and $R^4$ may independently be (C1-22)alkyl groups. In these embodiments, the alkyl group may be a (C1)alkyl(methyl), or a (C2)alkyl(ethyl), or a (C3)alkyl, or a (C4)alkyl, or a (C5)alkyl, or a (C6)alkyl, or a (C7)alkyl, or a (C8)alkyl, or a (C9)alkyl, or a (C10)alkyl, or a (C11)alkyl, or a (C12)alkyl, or a (C13)alkyl, or a (C14)alkyl, or a (C15)alkyl, or a (C16)alkyl, or a (C17)alkyl, or a (C18)alkyl, or a (C19)alkyl, or a (C20)alkyl, or a (C21)alkyl, or a (C22)alkyl.

In certain embodiments, the groups $R^1$, $R^2$, $R^3$, and $R^4$ may independently be (C1-12)alkyl groups. In these embodiments, the alkyl group may be a (C1)alkyl(methyl), or a (C2)alkyl(ethyl), or a (C3)alkyl, or a (C4)alkyl, or a (C5)alkyl, or a (C6)alkyl, or a (C7)alkyl, or a (C8)alkyl, or a (C9)alkyl, or a (C10)alkyl, or a (C11)alkyl, or a (C12)alkyl.

In certain embodiments, the groups $R^1$, $R^2$, $R^3$, and $R^4$ may independently be (C1-6)alkyl groups. In these embodiments, the alkyl group may be a (C1)alkyl(methyl), or a (C2)alkyl(ethyl), or a (C3)alkyl, or a (C4)alkyl, or a (C5)alkyl, or a (C6)alkyl.

In further variations, $R^1$ is (C8)alkyl and $R^2$, $R^3$, and $R^4$ are the same and are (C3-4)alkyl.

In other forms, $R^1$ is (C6)alkyl and $R^2$, $R^3$, and $R^4$ are the same and are (C3-4)alkyl.

In some aspects, a molecular precursor compound can be represented by the formula $(M^A\text{-}(ER^2)(ER^3)(ER^4)M^BR^1)_2$, referred to as a dimer, wherein $M^A$ is a monovalent atom selected from Cu, Au, Ag, and Hg, which is stabilized by interactions with one or more chalcogen atoms. The atom $M^A$ may further be stabilized by interacting with another $M^A$ atom. Aside from interactions with chalcogen atoms, the atom $M^A$ has no other ligands attached. $M^B$ is an atom of Ga or In, each E is independently S or Se, and $R^1$, $R^2$, $R^3$, and $R^4$ are as defined above. In certain variations, $M^A$ is an atom of Group 11, or $M^A$ is Cu.

A molecular precursor compound of the MP1 family may be crystalline, or non-crystalline.

Examples of molecular precursor compounds of the MP1 family of this disclosure include compounds having any one of the formulas: Cu—$(S^tBu)_3In^iPr$; Cu—$(S^tBu)_3In^nBu$; Cu—$(Se^tBu)_3In^nBu$; Cu—$(S^tBu)_3In^sBu$; Cu—$(Se^tBu)_3Ga^tBu$; Cu—$(S^tBu)_3Ga^tBu$; Cu—$(Se^tBu)_3In^tBu$; Cu—$(Se^tBu)_3In^iPr$; Cu—$(Se^tBu)_3In^sBu$; Cu—$(Se^tBu)_3Ga^iPr$; Cu—$(S^tBu)_3Ga^iPr$; and a dimer of any of the foregoing.

Examples of molecular precursor compounds of the MP1 family of this disclosure include compounds having any one of the formulas: Cu—$(S^tBu)_3In(NEt_2)$; Cu—$(S^tBu)_3In(N^iPr_2)$; Cu—$(Se^tBu)_3In(NEt_2)$; Cu—$(S^tBu)_3In(NMe_2)$; Cu—$(Se^tBu)_3Ga(NEt_2)$; Cu—$(S^tBu)_3Ga(N^nBu_2)$; Cu—$(Se^tBu)_3In(NEt_2)$; Cu—$(Se^tBu)_3In(N^iPr_2)$; Cu—$(Se^tBu)_3In(N^iPr_2)$; Cu—$(Se^tBu)_3Ga(N^iPr_2)$; Cu—$(S^tBu)_3Ga(N^sBu_2)$; and a dimer of any of the foregoing.

Examples of molecular precursor compounds of the MP1 family of this disclosure include compounds having any one of the formulas: Cu—$(S^tBu)_3Tl^iPr$; Cu—$(S^tBu)_3Tl^nBu$; Cu—$(Se^tBu)_3Tl^nBu$; Cu—$(S^tBu)_3Tl^tBu$; Cu—$(Se^tBu)_3Tl^tBu$; Cu—$(Se^tBu)_3Tl^iPr$; and a dimer of any of the foregoing.

Examples of molecular precursor compounds of the MP1 family of this disclosure include compounds having any one of the formulas: Au—$(S^tBu)_3In^iPr$; Ag—$(S^tBu)_3In^nBu$; Hg—$(Se^tBu)_3Ga^tBu$; and a dimer of any of the foregoing.

Examples of molecular precursor compounds of the MP1 family of this disclosure include compounds having any one of the formulas: Cu—$(S^nBu)_2(S^tBu)In^tBu$; Cu—$(S^tBu)_2(S^nBu)In^iPr$; Cu—$(S^tBu)_2(S^iPr)In^nBu$; Cu—$(S^tBu)_2(Se^iPr)In^iPr$; Cu-$(Te^tBu)_2(Se^iPr)In^nBu$; Cu—$(Se^tBu)_2(Te^iPr)In^nBu$; Cu—$(S^tBu)_2(Te^iPr)In^tBu$; and a dimer of any of the foregoing.

Examples of molecular precursor compounds of the MP1 family of this disclosure include compounds having any one of the formulas: Cu—$(S^tBu)(S^iPr)(S^nBu)In^iPr$; Cu—$(Se^tBu)(S^iPr)(S^nBu)In^nBu$; Cu—$(Se^tBu)(S^iPr)(Te^nBu)In^tBu$; Cu—$(Se^tBu)(Se^iPr)(Se^nBu)In^iPr$; and a dimer of any of the foregoing.

Examples of molecular precursor compounds of the MP1 family of this disclosure include compounds having any one of the formulas: Cu—$(S^tBu)_3In(n$-octyl$)$; Cu—$(S^tBu)_3In(n$-dodecyl$)$; Cu—$(Se^tBu)_3In($branched-C18$)$; Cu—$(S^tBu)_3In($branched-C22$)$; Cu—$(Se(n$-hexyl$))_3Ga^tBu$; Cu—$(S(n$-octyl$))_3Ga^tBu$; and a dimer of any of the foregoing.

As used herein, the term dimer refers to a molecule composed of two moieties having the same empirical formula. For example, (Cu—$(S^tBu)_3In^iPr)_2$ is a dimer of Cu—$(S^tBu)_3In^iPr$.

Preparation of Molecular Precursors (MP1)

Embodiments of this invention provide a family MP1 of precursor molecules which can be synthesized from a compound containing an atom $M^B$ of Group 13 selected from Al, Ga, In, and Tl, and a compound containing a monovalent atom $M^A$ selected from Cu, Au, Ag, and Hg.

Advantageously facile routes for the synthesis and isolation of molecular precursor compounds of this invention have been discovered, as described below.

In some aspects, synthesis of a molecular precursor of the MP1 family begins with providing a compound having the formula $R^1_2M^BER^2$.

A compound having the formula $R^1_2M^BER^2$ containing a Group 13 atom $M^B$ can be prepared by reacting $M^BR^1_3$ with $HER^2$, where $R^1$, $R^2$, and E are as defined above.

In other variations, a compound having the formula $R^1_2M^BER^2$ containing a Group 13 atom $M^B$ can be prepared by reacting $R^1_2M^BX$ with $M^CER^2$, where $R^1$, $R^2$ and E are as defined above, X is halogen, and $M^C$ is an alkali metal.

In additional variations, a compound having the formula $R^1_2M^BER^2$ containing a Group 13 atom $M^B$ can be prepared by reacting $R^1_2M^BX$ with $R^2ESi(CH_3)_3$, where $R^1$, $R^2$ and E are as defined above, and X is halogen.

To prepare a molecular precursor of the MP1 family, the compound $R^1_2M^BER^2$ may be reacted with a compound containing a monovalent atom $M^A$ defined above.

In some embodiments, a compound $R^1_2M^BER^2$ can be contacted with a chalcogen-containing compound $M^A(ER^3)$ in the presence of one equivalent of $HER^4$, where $M^A$, $M^B$, E, $R^1$, $R^2$, $R^3$, and $R^4$ are as defined above. As shown in Reaction Scheme 1a, $M^BR^1_3$ can be reacted with $HER^2$ to form $R^1_2M^BER^2$. The product $R^1_2M^BER^2$ can be contacted with a compound $M^A(ER^3)$ in the presence of one equivalent of $HER^4$ to form a molecular precursor compound having the formula $M^A$-$(ER^2)(ER^3)(ER^4)M^BR^1$.

REACTION SCHEME 1a:

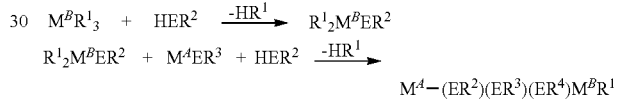

In Reaction Scheme 1a, for each occurrence, E may be S, Se, or Te.

In certain variations, the starting compound $M^BR^1_3$ may be stabilized as an adduct, for example, as the diethylether adduct, and the diethylether may be removed.

Alternatively, in some embodiments, $M^BR^1_3$ can be reacted with a compound $M^A(ER^3)$ in the presence of two equivalents of $HER^2$ to form a molecular precursor compound having the formula $M^A$-$(ER^2)_2(ER^3)M^BR^1$. As shown in Reaction Scheme 1b, $M^BR^1_3$ can be reacted with compounds $M^A(ER^3)$, $HER^2$, and $HER^4$ to form a molecular precursor compound having the formula $M^A$-$(ER^2)(ER^3)(ER^4)M^BR^1$.

REACTION SCHEME 1b:

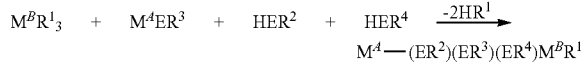

In further aspects, a compound $(NR^1_2)M^B(R^2)(ER^3)$ may be contacted with a chalcogen-containing compound $M^A(ER^4)$ in the presence of one equivalent of $HER^5$, where $M^A$, $M^B$, E, $R^1$, $R^2$, $R^3$, and $R^4$ are as defined above, $R^5$ is defined the same as $R^1$, $R^2$, $R^3$, and $R^4$, and $NR^1_2$ is amido. As shown in Reaction Scheme 1c, $(NR^1_2)M^BR^2_2$ may be reacted with $HER^3$ to form $(NR^1_2)M^B(R^2)(ER^3)$. The product $(NR^1_2)M^B(R^2)(ER^3)$ may be contacted with a compound $M^A(ER^4)$ in the presence of one equivalent of $HER^5$ to form a molecular precursor compound having the formula $M^A$-$(ER^3)(ER^4)(ER^5)M^B(NR^1_2)$.

REACTION SCHEME 1c:

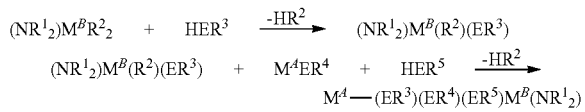

In Reaction Scheme 1c, the ligand ($NR^1_2$) corresponds to the $R^1$ of Reaction Scheme 1a.

In additional variations, a compound $R^1_2M^BX_2$ can be contacted with a chalcogen-containing compound $M^4(ER^2)$ in the presence of one equivalent of $R^3ESi(CH_3)_3$ and one equivalent of $R^4ESi(CH_3)_3$, where $M^4$, $M^B$, E, $R^1$, $R^2$, $R^3$, and $R^4$ are as defined above. As shown in Reaction Scheme 1d, $R^1M^BX_2$ can be reacted with $M^4(ER^2)$, $R^3ESi(CH_3)_3$, and $R^4ESi(CH_3)_3$ to form a molecular precursor compound having the formula $M^4$-$(ER^2)(ER^3)(ER^4)M^BR^1$.

REACTION SCHEME 1d:

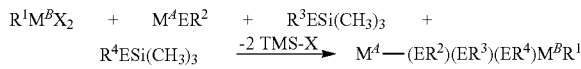

The reactions and manipulations of reagents can be carried out using known techniques under controlled inert atmosphere, such as dry nitrogen, and anaerobic conditions using a drybox and a Schlenk line system.

In certain examples, a molecular precursor of the MP1 family can be synthesized by the following procedure. A Schlenk tube can be charged with $R^1_2M^B(ER^2)$ and an equimolar amount of $M^4(ER^2)$ in a glovebox in an inert, anaerobic atmosphere. To this mixture can be added dry solvent via cannula on a Schlenk line. The mixture can optionally be heated to dissolve or disperse the components. An equimolar amount of $HER^2$ can be added by use of a syringe and the Schlenk tube sealed under $N_2$. The mixture can be heated, optionally for about 12 hours at a temperature from about 30° C. to about 120° C. The solution can then be cooled, optionally for several hours at a temperature from about –80° C. to about 15° C. A solid or crystalline product can be isolated.

Among other things, in some embodiments, certain starting compounds were made in order to synthesize molecular precursor molecules of this disclosure. The starting compounds include certain compounds having one of the formulas $M^4ER$ and $R^1_2M^BER^2$, where $M^B$ is Ga or In, E is S or Se, and $R^1$ and $R^2$ are alkyl. Examples of the starting compounds that were prepared include $CuSe^tBu$, $^nBu_2In(Se^tBu)$, $^tBu_2Ga(Se^tBu)$, $^tBu_2In(Se^tBu)$, and $^iPr_2In(Se^tBu)$.

Methods for making compounds comprising the formula $M^4ER$ include reacting $M^4Cl$ with LiER, and reacting $M^4_2O$ with 2 equivalents of HER. In another method, $M^4Cl$ can be reacted with $RESi(CH_3)_3$. In one example, CuCl was reacted with $^tBuSeSi(CH_3)_3$ in THF, and filtered. A red precipitate was obtained which was washed with pentane and dried under vacuum. A red solid was isolated at a yield of 90%.

Molecular Precursors (MP2) for Semiconductors and Optoelectronics

In some embodiments, a molecular precursor compound of the family MP2 contains two different atoms $M^{B1}$ and $M^{B2}$ of Group 13 selected from Al, Ga, In, and Tl, which are stabilized by having ligands attached. These molecular precursor compounds further contain two monovalent atoms $M^{A1}$ and $M^{A2}$ which are the same or different and are selected from Cu, Au, Ag, and Hg. $M^{A1}$ and $M^{A2}$ are each stabilized by interactions with one or more chalcogen atoms. The atoms $M^{A1}$ and $M^{A2}$ may further be stabilized by interacting with each other. Aside from interactions with chalcogen atoms, the atoms $M^{A1}$ and $M^{A2}$ have no other ligands attached.

Figure 2:
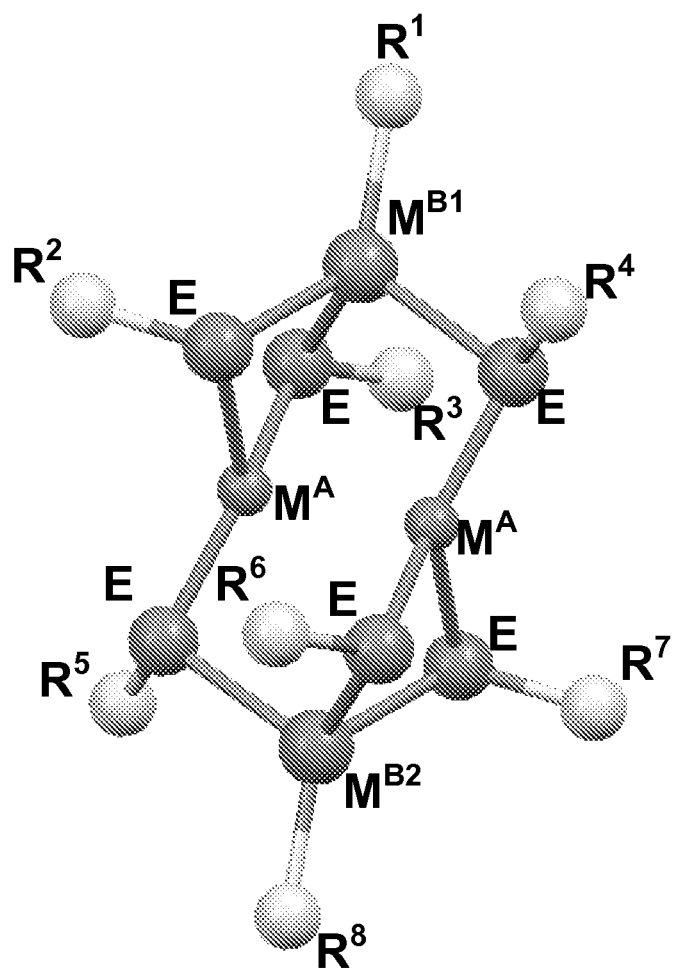
FIG. 2.

The general structure of a family of MP2 precursor molecules can be represented) by the formula $(R^1M^{B1}(ER^2)(ER^3)(ER^4)$-$M^{A1})(M^{A2}$-$(ER^5)(ER^6)(ER^7)M^{B2}R^8)$, as shown in FIG. 2.

As shown in FIG. 2, the local structure surrounding the atom $M^{B1}$ in a molecule of the MP2 family is a tetrahedral arrangement of four atoms. At one apex of the tetrahedron is an atom of $R^1$ through which it is attached to $M^{B1}$. The remainder of the tetrahedron is formed by the chalcogen atoms of three ligands $(ER^2)$, $(ER^3)$, and $(ER^4)$, each of which is attached through a chalcogen atom to $M^{B1}$.

As shown in FIG. 2, the local structure surrounding the atom $M^{B2}$ is a tetrahedral arrangement of four atoms. At one apex of the tetrahedron is a carbon atom of $R^8$ through which it is attached to $M^{B2}$. The remainder of the tetrahedron is formed by the chalcogen atoms of three ligands $(ER^5)$, $(ER^6)$, and $(ER^7)$, each of which is attached through a chalcogen atom to $M^{B2}$.

As shown in FIG. 2, the local structure surrounding each of the atoms $M^{A1}$ and $M^{A2}$ (labels "$M^A$" in FIG. 2) includes bonding interactions with three chalcogen atoms. For one of the two atoms $M^{A1}$ or $M^{A2}$, the three chalcogen atoms with which it has bonding interactions belong to the three ligands $(ER^2)$, $(ER^3)$, and $(ER^5)$. For the other of the two atoms $M^{A1}$ or $M^{A2}$, the three chalcogen atoms belong to the three ligands $(ER^4)$, $(ER^6)$, and $(ER^7)$. The ligands $(ER^2)$, $(ER^3)$, $(ER^4)$, $(ER^5)$, $(ER^6)$, and $(ER^7)$ are chalcogen bridging ligands that are each shared through bonding of their chalcogen atom to an $M^A$ atom and an $M^B$ atom. Atoms $M^{A1}$ and $M^{A2}$ may further be stabilized by interacting with each other. Aside from interactions with chalcogen atoms, the atoms $M^A$ have no other ligands attached.

The portion $R^n$, where n is 1, 2, 3, 4, 5, 6, 7 or 8, of each of the ligands attached to the atoms $M^A$ and $M^B$ may be a good leaving group in relation to a transition of the molecular precursor compound at elevated temperatures or upon application of energy.

The arrangement of atoms in a molecular precursor compound of the MP2 family may be described by the formula $(R^1M^{B1}(ER^2)(ER^3)(ER^4)$-$M^{A1})(M^{A2}$-$(ER^5)(ER^6)(ER^7)M^{B2}R^8)$, wherein E is chalcogen, and $R^1$, $R^2$, $R^3$, $R^4$, $R^5$, $R^6$, $R^7$, and $R^8$ are the same or different and are groups attached through a carbon or non-carbon atom, including alkyl, aryl, heteroaryl, alkenyl, amido, silyl, and inorganic and organic ligands. In some embodiments, $R^1$, $R^2$, $R^3$, $R^4$, $R^5$, $R^6$, $R^7$, and $R^8$ are the same or different and are alkyl groups attached through a carbon atom.

In some embodiments, molecular precursor compounds of the MP2 family advantageously do not contain a phosphine ligand, or a ligand or attached compound containing phosphorus, arsenic, or antimony, or a halogen ligand.

In further embodiments, the groups $R^1$, $R^2$, $R^3$, $R^4$, $R^5$, $R^6$, $R^7$, and $R^8$ may independently be (C1-22)alkyl groups. In these embodiments, the alkyl group may be a (C1)alkyl(methyl), or a (C2)alkyl(ethyl), or a (C3)alkyl, or a (C4)alkyl, or a (C5)alkyl, or a (C6)alkyl, or a (C7)alkyl, or a (C8)alkyl, or a (C9)alkyl, or a (C10)alkyl, or a (C11)alkyl, or a (C12)alkyl, or a (C13)alkyl, or a (C14)alkyl, or a (C15)alkyl, or a (C16) alkyl, or a (C17)alkyl, or a (C18)alkyl, or a (C19)alkyl, or a (C20)alkyl, or a (C21)alkyl, or a (C22)alkyl.

In certain embodiments, the groups $R^1$, $R^2$, $R^3$, $R^4$, $R^5$, $R^6$, $R^7$, and $R^8$ may independently be (C1-12)alkyl groups. In these embodiments, the alkyl group may be a (C1)alkyl(methyl), or a (C2)alkyl(ethyl), or a (C3)alkyl, or a (C4)alkyl, or a (C5)alkyl, or a (C6)alkyl, or a (C7)alkyl, or a (C8)alkyl, or a (C9)alkyl, or a (C10)alkyl, or a (C11)alkyl, or a (C12)alkyl.

In certain embodiments, the groups $R^1$, $R^2$, $R^3$, $R^4$, $R^5$, $R^6$, $R^7$, and $R^8$ may independently be (C1-6)alkyl groups. In these embodiments, the alkyl group may be a (C1)alkyl(methyl), or a (C2)alkyl(ethyl), or a (C3)alkyl, or a (C4)alkyl, or a (C5)alkyl, or a (C6)alkyl.

In further variations, $R^1$ and $R^8$ are (C8)alkyl and $R^2$, $R^3$, $R^4$, $R^5$, $R^6$, and $R^7$ are the same and are (C3-4)alkyl.

In other forms, $R^1$ and $R^8$ are (C6)alkyl and $R^2$, $R^3$, $R^4$, $R^5$, $R^6$, and $R^7$ are the same and are (C3-4)alkyl.

A molecular precursor compound of the MP2 family may be crystalline, or non-crystalline.

Examples of molecular precursor compounds of the MP2 family of this disclosure include compounds having any one of the formulas: ($^i$PrIn(S$^t$Bu)$_3$-Cu)(Cu—(S$^t$Bu)$_3$Ga$^i$Pr); ($^n$BuIn(S$^t$Bu)$_3$-Cu)(Cu—(S$^t$Bu)$_3$Ga$^n$Bu); ($^n$BuGa(Se$^t$Bu)$_3$-Cu)(Cu—(Se$^t$Bu)$_3$Tl$^n$Bu); ($^t$BuIn(S$^t$Bu)$_3$-Cu)(Cu—(S$^t$Bu)$_3$Ga$^t$Bu); ($^t$BuTl(Se$^t$Bu)$_3$-Cu)(Cu—(Se$^t$Bu)$_3$Ga$^t$Bu); ($^t$BuGa(S$^t$Bu)$_3$-Cu)(Cu—(S$^t$Bu)$_3$In$^t$Bu); ($^t$BuIn(Se$^t$Bu)$_3$-Cu)(Cu—(Se$^t$Bu)$_3$Ga$^t$Bu); and ($^i$PrIn(Se$^t$Bu)$_3$-Cu)(Cu—(Se$^t$Bu)$_3$Ga$^i$Pr).

Examples of molecular precursor compounds of the MP2 family of this disclosure include compounds having any one of the formulas: ((NEt$_2$)In(S$^t$Bu)$_3$-Cu)(Cu—(S$^t$Bu)$_3$Ga(NEt$_2$)); ((NEt$_2$)In(S$^t$Bu)$_3$-Cu)(Cu—(S$^t$Bu)$_3$Ga$^n$Bu); ((NEt$_2$)Ga(Se$^t$Bu)$_3$-Cu)(Cu—(Se$^t$Bu)$_3$Tl$^n$Bu); ((NEt$_2$)In(S$^t$Bu)$_3$-Cu)(Cu—(S$^t$Bu)$_3$Ga(NEt$_2$)); ((NEt$_2$)Tl(Se$^t$Bu)$_3$-Cu)(Cu—(Se$^t$Bu)$_3$Ga(NEt$_2$)); ((NiPr$_2$)Ga(S$^t$Bu)$_3$-Cu)(Cu—(S$^t$Bu)$_3$In(NiPr$_2$)); ((NiPr$_2$)In(Se$^t$Bu)$_3$-Cu)(Cu—(Se$^t$Bu)$_3$Ga(NiPr$_2$)); and ((NiPr$_2$)In(Se$^t$Bu)$_3$-Cu)(Cu—(Se$^t$Bu)$_3$Ga(NiPr$_2$)).

Examples of molecular precursor compounds of the MP2 family of this disclosure include compounds having any one of the formulas: ($^i$PrIn(S$^t$Bu)$_3$-Cu)(Ag—(S$^t$Bu)$_3$Ga$^i$Pr); ($^n$BuIn(S$^t$Bu)$_3$-Cu)(Au—(S$^t$Bu)$_3$Ga$^n$Bu); ($^n$BuGa(Se$^t$Bu)$_3$-Cu)(Ag—(Se$^t$Bu)$_3$Tl$^n$Bu); ($^t$BuIn(S$^t$Bu)$_3$-Cu)(Au—(S$^t$Bu)$_3$Ga$^t$Bu); ($^t$BuTl(Se$^t$Bu)$_3$-Cu)(Ag—(Se$^t$Bu)$_3$Ga$^t$Bu); ($^t$BuGa(S$^t$Bu)$_3$-Cu)(Au—(S$^t$Bu)$_3$In$^t$Bu); ($^t$BuIn(Se$^t$Bu)$_3$-Cu)(Ag—(Se$^t$Bu)$_3$Ga$^t$Bu); and ($^i$PrIn(Se$^t$Bu)$_3$-Cu)(Au—(Se$^t$Bu)$_3$Ga$^i$Pr).

Examples of molecular precursor compounds of the MP2 family of this disclosure include compounds having any one of the formulas: ($^i$PrGa(S$^t$Bu)$_3$-Au)(Au—(S$^t$Bu)$_3$In$^i$Pr); ($^n$BuGa(S$^t$Bu)$_3$-Ag)(Ag—(S$^t$Bu)$_3$In$^n$Bu); and ($^t$BuTl(Se$^t$Bu)$_3$-Hg)(Hg—(Se$^t$Bu)$_3$In$^t$Bu).

Examples of molecular precursor compounds of the MP2 family of this disclosure include compounds having any one of the formulas: ($^i$PrIn(S$^n$Bu)(S$^t$Bu)$_2$-Cu)(Cu—(S$^t$Bu)$_2$(S$^t$Bu)Ga$^i$Pr); ($^n$BuIn(S$^i$Pr)(S$^t$Bu)$_2$-Cu)(Cu—(S$^t$Bu)$_2$(S$^i$Pr)Ga$^n$Bu); ($^i$PrTl(Se$^i$Pr)(S$^t$Bu)$_2$-Cu)(Cu—(S$^t$Bu)$_2$(Se$^i$Pr)Ga$^i$Pr); ($^n$BuGa(Se$^i$Pr)(Te$^t$Bu)$_2$-Cu)(Cu-(Te$^t$Bu)$_2$(Se$^i$Pr)In$^n$Bu); ($^n$BuTl(Te$^i$Pr)(Se$^t$Bu)$_2$-Cu)(Cu—(Se$^t$Bu)$_2$(Te$^i$Pr)In$^n$Bu); and ($^t$BuGa(Te$^i$Pr)(S$^t$Bu)$_2$-Cu)(Cu—(S$^t$Bu)$_2$(Te$^i$Pr)In$^t$Bu).

Examples of molecular precursor compounds of the MP2 family of this disclosure include compounds having any one of the formulas: ($^i$PrIn(S$^n$Bu)(S$^i$Pr)(S$^t$Bu)—Cu)(Cu—(S$^t$Bu)(S$^i$Pr)(S$^n$Bu)Ga$^i$Pr); ($^n$BuIn(S$^n$Bu)(S$^i$Pr)(Se$^t$Bu)—Cu)(Cu—(Se$^t$Bu)(S$^i$Pr)(S$^n$Bu)Tl$^n$Bu); ($^t$BuGa(Te$^n$Bu)(S$^i$Pr)(Se$^t$Bu)—Cu)(Cu—(Se$^t$Bu)(S$^i$Pr)(Te$^n$Bu)In$^t$Bu); and ($^i$PrGa(Se$^n$Bu)(Se$^i$Pr)(Se$^n$Bu)—Cu)(Cu—(Se$^n$Bu)(Se$^i$Pr)(Se$^n$Bu)Tl$^i$Pr).

Examples of molecular precursor compounds of the MP2 family of this disclosure include compounds having any one of the formulas: ((n-octyl)In(S$^t$Bu)$_3$-Cu)(Cu—(S$^t$Bu)$_3$Ga(n-octyl)); ((n-dodecyl)In(S$^t$Bu)$_3$-Cu)(Cu—(S$^t$Bu)$_3$Ga(n-dodecyl)); ((branched-C18)Ga(Se$^t$Bu)$_3$-Cu)(Cu—(Se$^t$Bu)$_3$In(branched-C18)); ((branched-C22)In(S$^t$Bu)$_3$-Cu)(Cu—(S$^t$Bu)$_3$Tl(branched-C22)); ($^t$BuTl(Se(n-hexyl))$_3$-Cu)(Cu—(Se(n-hexyl))$_3$In$^t$Bu); and ($^t$BuGa(Se(n-octyl))$_3$-Cu)(Cu—(Se(n-octyl))$_3$Tl$^t$Bu).

Preparation of Molecular Precursors (MP2)

Embodiments of this invention provide a family MP2 of precursor molecules which can be synthesized from compounds containing an atom $M^B$ of Group 13 selected from Al, Ga, In, and Tl, and compounds containing a monovalent atom $M^A$ selected from Cu, Au, Ag, and Hg.

Advantageously facile routes for the synthesis and isolation of molecular precursor compounds of this invention are described below.

In some aspects, synthesis of a molecular precursor of the MP2 family begins with providing compounds having the formulas $R^1{}_2M^{B1}ER''$ and $R^8{}_2M^{B2}ER''$, where $M^{B1}$ and $M^{B2}$ are different Group 13 atoms.

Compounds having the formulas $R^1{}_2M^{B1}ER''$ and $R^8{}_2M^{B2}ER''$ can be prepared by reacting $M^{B1}R^1{}_3$ and $M^{B2}R^8{}_3$ with HER'', where $R^1$, $R^8$, and E are as defined above.

In other variations, a compound having the formula $R^1{}_2M^{B1}ER''$ can be prepared by reacting $R^1{}_2M^{B1}X$ with $M^CER''$, where X is halogen and $M^C$ is an alkali metal.

In additional variations, a compound having the formula $R^1{}_2M^{B1}ER''$ containing a Group 13 atom $M^B$ can be prepared by reacting $R^1{}_2M^{B1}X$ with $R^3ESi(CH_3)_3$, where $R^1$, $R^3$ and E are as defined above, and X is halogen.

To prepare a molecular precursor of the MP2 family, the compounds $R^1{}_2M^{B1}ER''$ and $R^8{}_2M^{B2}ER''$ may be reacted with a compound containing a monovalent atom $M^A$ defined above.

In some embodiments, the compounds $R^1{}_2M^{B1}ER''$ and $R^8{}_2M^{B2}ER''$ can be contacted with a chalcogen-containing compound $M^A(ER^4)$ in the presence of one equivalent of $HER^5$, where $R^4$ and $R^5$ are as defined above.

As shown in Reaction Scheme 2a, in some embodiments, $M^{B1}R^1{}_3$ and $M^{B2}R^8{}_3$ can be reacted with HER'' to form $R^1{}_2M^{B1}ER''$ and $R^8{}_2M^{B2}ER''$. The products $R^1{}_2M^{B1}ER''$ and $R^8{}_2M^{B2}ER''$ can be contacted with two equivalents of a compound $M^A(ER^4)$ in the presence of two equivalents of $HER^5$ to form a molecular precursor compound.

REACTION SCHEME 2a:

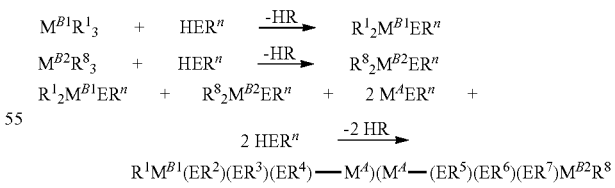

In the foregoing description, R'' represents a mixture of R groups, so that each group R'' can be independently different. The groups $R^1$, $R^2$, $R^3$, $R^4$, $R^5$, $R^6$, $R^7$, and $R^8$ are as defined above.

Reaction Scheme 2a may afford a mixture of compounds which can include compounds having one atom of $M^{B1}$ and one atom of $M^{B2}$, compounds having two atoms of $M^{B1}$ and zero atoms of $M^{B2}$, and compounds having zero atoms of $M^{B1}$ and two atoms of $M^{B2}$. These compounds have the formulas $(R^1M^{B1}(ER^2)(ER^3)(ER^4)\text{-}M^{A1})(M^{A2}\text{-}(ER^5)(ER^6)(ER^7)M^{B2}R^8)$, $(R^1M^{B1}(ER^2)(ER^3)(ER^4)\text{-}M^{A1})(M^{A2}\text{-}(ER^5)(ER^6)(ER^7)M^{B1}R^8)$, and $(R^1M^{B2}(ER^2)(ER^3)(ER^4)\text{-}M^{A1})(M^{A2}\text{-}(ER^5)(ER^6)(ER^7)M^{B2}R^8)$, respectively, wherein $M^{A1}$ and $M^{A2}$ are the same or different.

Compounds having the formula $(R^1M^{B1}(ER^2)(ER^3)(ER^4)\text{-}M^{A1})(M^{A2}\text{-}(ER^5)(ER^6)(ER^7)M^{B2}R^8)$ are MP2 molecular precursor compounds.

In certain variations, the starting compound $M^BR_3$ may be stabilized by a ligand such as diethylether.

Alternatively, as shown in Reaction Scheme 2b, in some embodiments, $M^{B1}R^1{}_3$ and $M^{B2}R^2{}_3$ can be reacted with two equivalents of a compound $M^AER^n$ in the presence of four equivalents of $HER^4$ to form a molecular precursor compound.

REACTION SCHEME 2b:

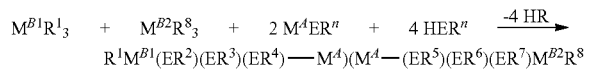

The product of Reaction Scheme 2b affords a mixture of compounds as described above for Reaction Scheme 2a. The mixture of compounds that is the product of Reaction Scheme 2a and 2b can be used directly to make molecular precursor compositions, as well as semiconductors and other materials.

In Reaction Schemes 2a and 2b, the atom $M^A$ of $M^AER^n$ may represent a mixture of atoms $M^{A1}$ and $M^{A2}$.

In further aspects, compounds $(NR^1{}_2)M^{B1}(R'')(ER'')$ and $(NR^8{}_2)M^{B1}(R'')(ER'')$ can be contacted with two equivalents of a chalcogen-containing compound $M^A(ER'')$ in the presence of four equivalents of $HER''$, where $M^A$, $M^{B1}$, $M^{B2}$, E, $R^1$, $R^8$, and $R''$ are as defined above, and $NR^1{}_2$ is amido.

As shown in Reaction Scheme 2c, $(NR^1{}_2)M^{B1}R^1{}_2$ and $(NR^8{}_2)M^{B2}R^8{}_2$ can be reacted with $M^A(ER'')$ in the presence of $HER''$ to form a molecular precursor compound.

REACTION SCHEME 2c:

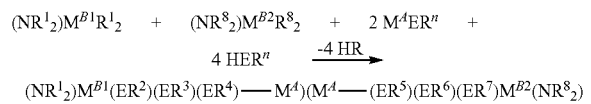

The reactions and manipulations of reagents can be carried out using known techniques under controlled inert atmosphere, such as dry nitrogen, and anaerobic conditions using a drybox and a Schlenk line system.

Molecular Precursors (MP3) for Semiconductors and Optoelectronics

In some embodiments, a molecular precursor compound of the family MP3 contains an atom $M^B$ of Group 13 selected from Al, Ga, In, and Tl, which is stabilized by having ligands attached. These molecular precursor compounds further contain a divalent metal atom $M^A$ which is stabilized by having chalcogen-containing ligands attached. Divalent metal atoms $M^A$ include Cu, Zn, Cd, Pt, Pd, Mo, W, Cr, Ni, Mn, Fe, Co, V, and Hg. Aside from interactions with chalcogen-containing ligands, the atom $M^A$ has no other ligands attached.

Figure 3:
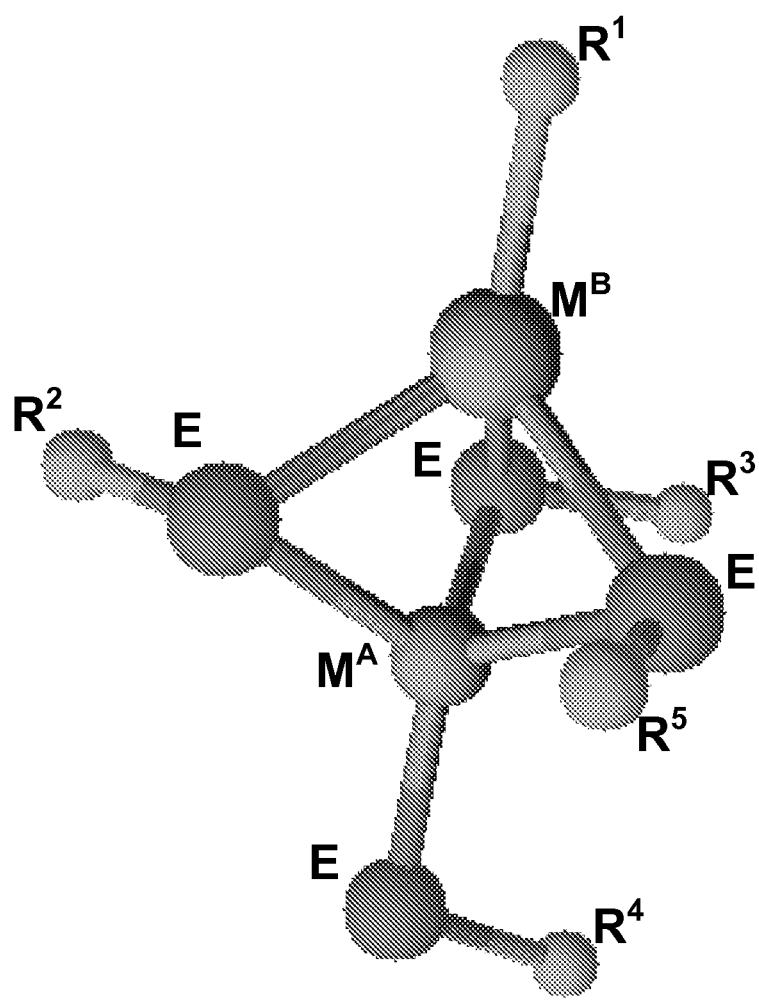
FIG. 3.

The general structure of a precursor molecule of the MP3 family can be represented by the formula $(R^4E)M^A(ER^3)(ER^5)(ER^2)M^BR^1$, as shown in FIG. 3.

The molecular structure of a precursor compound of the MP3 family is of a monomer.

As shown in FIG. 3, the local structure surrounding the atom $M^B$ is a tetrahedral arrangement of four atoms. At one apex of the $M^B$ tetrahedron is an atom of $R^1$ through which it is attached to $M^B$. The remainder of the tetrahedron is formed by the chalcogen atoms of three ligands $(ER^2)$, $(ER^3)$, and $(ER^5)$, each of which is attached through a chalcogen atom to $M^B$.

As shown in FIG. 3, the local structure surrounding the atom $M^A$ is a tetrahedral arrangement of four atoms. At one apex of the $M^A$ tetrahedron is a chalcogen atom of the ligand $(ER^4)$ through which it is attached to $M^A$. The remainder of the tetrahedron is formed by the chalcogen atoms of three ligands $(ER^2)$, $(ER^3)$, and $(ER^5)$, each attached through a chalcogen atom to $M^A$. The three ligands $(ER^2)$, $(ER^3)$, and $(ER^5)$ are chalcogen bridging ligands that are each shared through bonding of their chalcogen atom to $M^A$ and $M^B$. Aside from interactions with chalcogen atoms, the atom $M^A$ has no other ligands attached.

The portion $R''$, where n is 1, 2, 3, 4, or 5, of each of the ligands attached to the atoms $M^A$ and $M^B$ may be a good leaving group in relation to a transition of the molecular precursor compound at elevated temperatures or upon application of energy.

The arrangement of atoms in a molecular precursor compound of the MP3 family may be described by the formula $(R^4E)M^A(ER^3)(ER^5)(ER^2)M^BR^1$, wherein E is chalcogen, and $R^1$, $R^2$, $R^3$, $R^4$ and $R^5$ are the same or different and are groups attached through a carbon or non-carbon atom, including alkyl, aryl, heteroaryl, alkenyl, amido, silyl, and inorganic and organic ligands. In some embodiments, $R^1$, $R^2$, $R^3$, $R^4$ and $R^5$ are the same or different and are alkyl groups attached through a carbon atom.

In some embodiments, molecular precursor compounds of the MP3 family advantageously do not contain a phosphine ligand, or a ligand or attached compound containing phosphorus, arsenic, or antimony, or a halogen ligand.

Embodiments of this invention further provide a family MP3 of molecular precursor compounds in which the arrangement of atoms may be described by the formula $(R^4E)Cu(ER^3)(ER^5)(ER^2)(In,Ga)R^1$, wherein E is chalcogen, and $R^1$, $R^2$, $R^3$, $R^4$ and $R^5$ are the same or different and are groups attached through a carbon or non-carbon atom, including alkyl, aryl, heteroaryl, alkenyl, amido, silyl, and inorganic and organic ligands. In some embodiments, $R^1$, $R^2$, $R^3$, $R^4$ and $R^5$ are the same or different and are alkyl groups attached through a carbon atom.

In certain variations, a molecular precursor compound of the MP3 family contains an atom $M^B$, being In or Ga, which is stabilized by attached ligands. These molecular precursor compounds further contain an atom $M^A$, being Cu, which is stabilized by interactions with one or more chalcogen atoms.

In further embodiments, the groups $R^1$, $R^2$, $R^3$, $R^4$ and $R^5$ may independently be (C1-22)alkyl groups. In these embodiments, the alkyl group may be a (C1)alkyl(methyl), or a (C2)alkyl(ethyl), or a (C3)alkyl, or a (C4)alkyl, or a (C5)alkyl, or a (C6)alkyl, or a (C7)alkyl, or a (C8)alkyl, or a (C9)alkyl, or a (C10)alkyl, or a (C11)alkyl, or a (C12)alkyl, or a (C13)alkyl, or a (C14)alkyl, or a (C15)alkyl, or a (C16)alkyl, or a (C17)alkyl, or a (C18)alkyl, or a (C19)alkyl, or a (C20)alkyl, or a (C21)alkyl, or a (C22)alkyl.

In certain embodiments, the groups $R^1$, $R^2$, $R^3$, $R^4$ and $R^5$ may independently be (C1-12)alkyl groups. In these embodiments, the alkyl group may be a (C1)alkyl(methyl), or a (C2)alkyl(ethyl), or a (C3)alkyl, or a (C4)alkyl, or a (C5)

alkyl, or a (C6)alkyl, or a (C7)alkyl, or a (C8)alkyl, or a (C9)alkyl, or a (C10)alkyl, or a (C11)alkyl, or a (C12)alkyl.

In certain embodiments, the groups $R^1$, $R^2$, $R^3$, $R^4$ and $R^5$ may independently be (C1-6)alkyl groups. In these embodiments, the alkyl group may be a (C1)alkyl(methyl), or a (C2)alkyl(ethyl), or a (C3)alkyl, or a (C4)alkyl, or a (C5)alkyl, or a (C6)alkyl.

In further variations, $R^1$ is (C8)alkyl and $R^2$, $R^3$, $R^4$ and $R^5$ are the same and are (C3-4)alkyl.

In other forms, $R^1$ is (C6)alkyl and $R^2$, $R^3$, $R^4$ and $R^5$ are the same and are (C3-4)alkyl.

Figure 4:
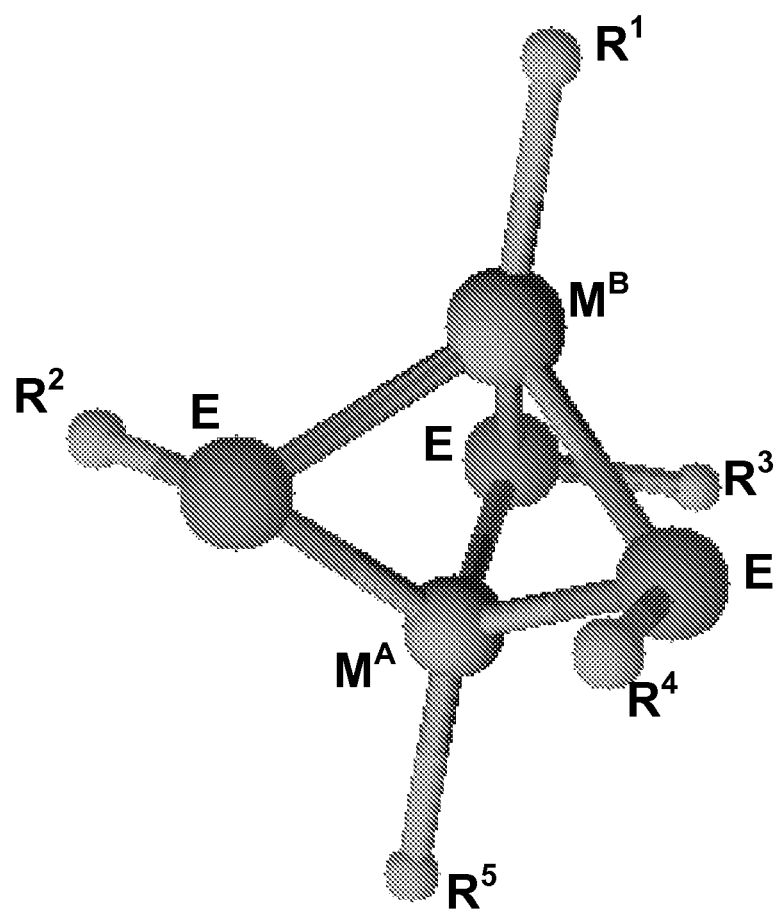
FIG. 4.

In further embodiments, a molecular precursor compound of the family MP3 may have the general structure represented by the formula $R^5 M^A(ER^4)(ER^3)(ER^2)M^B R^1$, as shown in FIG. 4. In these embodiments, a molecular precursor compound of the family MP3 contains an atom $M^B$ of Group 13 selected from Al, Ga, In, and Tl, which is stabilized by having ligands attached. These molecular precursor compounds further contain a divalent metal atom $M^A$ which is stabilized by having ligands attached. Divalent metal atoms $M^A$ include Cu, Zn, Cd, Pt, Pd, Mo, W, Cr, Ni, Mn, Fe, Co, V, and Hg.

The molecular structure of a precursor compound of the MP3 family having the general structure represented by the formula $R^5 M^A(ER^4)(ER^3)(ER^2)M^B R^1$ is of a monomer.

As shown in FIG. 4, the local structure surrounding the atom $M^B$ is a tetrahedral arrangement of four atoms. At one apex of the $M^B$ tetrahedron is a carbon atom of $R^1$ through which it is attached to $M^B$. The remainder of the tetrahedron is formed by the chalcogen atoms of three ligands $(ER^2)$, $(ER^3)$, and $(ER^4)$, each of which is attached through a chalcogen atom to $M^B$.

As shown in FIG. 4, the local structure surrounding the atom $M^A$ is a tetrahedral arrangement of four atoms. At one apex of the $M^A$ tetrahedron is a carbon atom of $R^5$ through which it is attached to $M^A$. The remainder of the tetrahedron is formed by the chalcogen atoms of three ligands $(ER^2)$, $(ER^3)$, and $(ER^4)$, each of which is attached through a chalcogen atom to $M^A$.

The arrangement of atoms in a molecular precursor compound of the MP3 family can be represented by the formula $R^5 M^A(ER^4)(ER^3)(ER^2)M^B R^1$, wherein E is chalcogen, and $R^1$, $R^2$, $R^3$, $R^4$ and $R^5$ are the same or different and are groups attached through a carbon or non-carbon atom, including alkyl, aryl, heteroaryl, alkenyl, amido, silyl, and inorganic and organic ligands. In some embodiments, $R^1$, $R^2$, $R^3$, $R^4$ and $R^5$ are the same or different and are alkyl groups attached through a carbon atom.

In some embodiments, molecular precursor compounds of the MP3 family advantageously do not contain a phosphine ligand, or a ligand or attached compound containing phosphorus, arsenic, or antimony, or a halogen ligand.

Embodiments of this invention further provide a family MP3 of molecular precursor compounds in which the arrangement of atoms may be described by the formula $R^5 Zn(ER^4)(ER^3)(ER^2)(In,Ga)R^1$, wherein E is chalcogen, and $R^1$, $R^2$, $R^3$, $R^4$ and $R^5$ are the same or different and are groups attached through a carbon or non-carbon atom, including alkyl, aryl, heteroaryl, alkenyl, amido, silyl, and inorganic and organic ligands. In some embodiments, $R^1$, $R^2$, $R^3$, $R^4$ and $R^5$ are the same or different and are alkyl groups attached through a carbon atom.

A molecular precursor compound of the MP3 family may be crystalline, or non-crystalline.

Examples of molecular precursor compounds of the MP3 family of this disclosure include compounds having any one of the formulas: ($^t$BuS)Cu(S$^t$Bu)$_3$In$^i$Pr; ($^t$BuS)Cu(S$^t$Bu)$_3$In″Bu; ($^t$BuSe)Cu(Se$^t$Bu)$_3$In″Bu; ($^t$BuS)Cu(S$^t$Bu)$_3$In$^t$Bu; ($^t$BuSe)Cu(Se$^t$Bu)$_3$Ga$^t$Bu; ($^t$BuS)Cu(S$^t$Bu)$_3$Ga$^t$Bu; ($^t$BuSe)Cu(Se$^t$Bu)$_3$In$^t$Bu; and ($^t$BuSe)Cu(Se$^t$Bu)$_3$In$^i$Pr.

Examples of molecular precursor compounds of the MP3 family of this disclosure include compounds having any one of the formulas: ($^t$BuS)Cu(S$^t$Bu)$_3$Ga$^i$Pr; ($^t$BuS)Cu(S$^t$Bu)$_3$Tl″Bu; ($^t$BuSe)Cu(Se$^t$Bu)$_3$Ga″Bu; ($^t$BuS)Cu(S$^t$Bu)$_3$Ga$^t$Bu; ($^t$BuSe)Cu(Se$^t$Bu)$_3$Tl$^t$Bu; and ($^t$BuSe)Cu(Se$^t$Bu)$_3$Ga$^i$Pr.

Examples of molecular precursor compounds of the MP3 family of this disclosure include compounds having any one of the formulas: ($^t$BuS)Cu(S$^t$Bu)$_3$Ga(NEt$_2$); ($^t$BuS)Cu(S$^t$Bu)$_3$Tl″(NEt$_2$); ($^t$BuSe)Cu(Se$^t$Bu)$_3$Ga(NEt$_2$); ($^t$BuS)Cu(S$^t$Bu)$_3$Ga(NEt$_2$); ($^t$BuSe)Cu(Se$^t$Bu)$_3$Tl$^t$(NEt$_2$); and ($^t$BuSe)Cu(Se$^t$Bu)$_3$Ga(NEt$_2$).

Examples of molecular precursor compounds of the MP3 family of this disclosure include compounds having any one of the formulas: ($^t$BuS)Cu(S$^t$Bu)$_3$In(NEt$_2$); ($^t$BuS)Cu(S$^t$Bu)$_3$In(NEt$_2$); ($^t$BuSe)Cu(Se$^t$Bu)$_3$In(N$^i$Pr$_2$); ($^t$BuS)Cu(S$^t$Bu)$_3$In(N$^i$Pr$_2$); ($^t$BuSe)Cu(Se$^t$Bu)$_3$Ga(N$^i$Pr$_2$); ($^t$BuS)Cu(S$^t$Bu)$_3$Ga(N$^i$Pr$_2$); ($^t$BuSe)Cu(Se$^t$Bu)$_3$In(N″Bu$_2$); and ($^t$BuSe)Cu(Se$^t$Bu)$_3$In(N$^s$Bu$_2$).

Examples of molecular precursor compounds of the MP3 family of this disclosure include compounds having any one of the formulas: ($^t$BuS)Zn(S$^t$Bu)$_3$In$^i$Pr; ($^t$BuS)Pt(S$^t$Bu)$_3$In″Bu; ($^t$BuSe)Pd(Se$^t$Bu)$_3$In″Bu; ($^t$BuS)Mo(S$^t$Bu)$_3$In$^t$Bu; ($^t$BuSe)W(Se$^t$Bu)$_3$Ga$^t$Bu; ($^t$BuS)Cr(S$^t$Bu)$_3$Ga$^t$Bu; ($^t$BuS)Ni(S$^t$Bu)$_3$In$^i$Pr; ($^t$BuS)Mn(S$^t$Bu)$_3$In″Bu; ($^t$BuSe)Fe(Se$^t$Bu)$_3$In″Bu; ($^t$BuS)Co(S$^t$Bu)$_3$In$^t$Bu; ($^t$BuSe)Hg(Se$^t$Bu)$_3$Ga$^t$Bu; ($^t$BuS)Cd(S$^t$Bu)$_3$In$^i$Pr; ($^t$BuS)V(S$^t$Bu)$_3$In″Bu; ($^t$BuS)Ru(S$^t$Bu)$_3$In$^i$Pr; ($^t$BuS)Rh(S$^t$Bu)$_3$In″Bu; ($^t$BuSe)Re(Se$^t$Bu)$_3$In″Bu; ($^t$BuS)Os(S$^t$Bu)$_3$In$^t$Bu; and ($^t$BuSe)Ir(Se$^t$Bu)$_3$Ga$^t$Bu.

Examples of molecular precursor compounds of the MP3 family of this disclosure include compounds having any one of the formulas: ($^t$BuS)Cu(S$^t$Bu)$_2$(S″Bu)In$^i$Pr; ($^t$BuS)Cu(S$^t$Bu)$_2$(S$^i$Pr)In″Bu; ($^t$BuS)Cu(S$^t$Bu)$_2$(Se$^i$Pr)In$^i$Pr; ($^t$BuTe)Cu(Te$^t$Bu)$_2$(Se$^i$Pr)In″Bu; ($^t$BuSe)Cu(Se$^t$Bu)$_2$(Te$^i$Pr)In″Bu; and ($^t$BuS)Cu(S$^t$Bu)$_2$(Te$^i$Pr)In$^t$Bu.

Examples of molecular precursor compounds of the MP3 family of this disclosure include compounds having any one of the formulas: (″BuS)Cu(S$^t$Bu)(S$^i$Pr)(S″Bu)In$^i$Pr; (″BuS)Cu(Se$^t$Bu)(S$^i$Pr)(S″Bu)In″Bu; ($^i$PrS)Cu(Se$^t$Bu)(S$^i$Pr)(Te″Bu)In$^t$Bu; and ($^i$PrSe)Cu(Se$^t$Bu)(Se$^i$Pr)(Se$^t$Bu)In$^i$Pr.

Examples of molecular precursor compounds of the MP3 family of this disclosure include compounds having any one of the formulas: ($^t$BuS)Cu(S$^t$Bu)$_3$In(n-octyl); ($^t$BuS)Cu(S$^t$Bu)$_3$In(n-dodecyl); ($^t$BuSe)Cu(Se$^t$Bu)$_3$In(branched-C18); ($^t$BuS)Cu(S$^t$Bu)$_3$In(branched-C22); ((n-hexyl)Se)Cu(Se(n-hexyl))$_3$Ga$^t$Bu; and ((n-octyl)S)Cu(S(n-octyl))$_3$Ga$^t$Bu.

Examples of molecular precursor compounds of the MP3 family of this disclosure include compounds having any one of the formulas: ($^t$BuS)Cu(S$^t$Bu)$_3$In$^i$Pr; (″BuS)Cu(S$^t$Bu)$_3$In″Bu; ($^i$PrSe)Cu(Se$^t$Bu)$_3$In″Bu; ($^i$PrS)Cu(S$^t$Bu)$_3$In$^t$Bu; (″BuSe)Cu(Se$^t$Bu)$_3$Ga$^t$Bu; ($^i$PrS)Cu(S$^t$Bu)$_3$Ga$^t$Bu; (″BuSe)Cu(Se$^t$Bu)$_3$In$^t$Bu; and ($^i$PrSe)Cu(Se$^t$Bu)$_3$In$^i$Pr.

Examples of molecular precursor compounds of the MP3 family of this disclosure include compounds having any one of the formulas: $^t$BuCu(S$^t$Bu)$_3$In$^i$Pr; $^t$BuZn(S$^t$Bu)$_3$In″Bu; $^t$BuZn(Se$^t$Bu)$_3$In″Bu; $^t$BuZn(S$^t$Bu)$_3$In$^t$Bu; $^t$BuZn(Se$^t$Bu)$_3$Ga$^t$Bu; $^t$BuZn(S$^t$Bu)$_3$Ga$^t$Bu; $^t$BuZn(Se$^t$Bu)$_3$In$^t$Bu; and $^t$BuCu(Se$^t$Bu)$_3$In$^i$Pr.

Examples of molecular precursor compounds of the MP3 family of this disclosure include compounds having any one of the formulas: $^t$BuZn(S$^t$Bu)$_3$In$^i$Pr.

Examples of molecular precursor compounds of the MP3 family of this disclosure include compounds having any one of the formulas: (NEt$_2$)Cu(S$^t$Bu)$_3$In(NEt$_2$); (N$^i$Pr$_2$)Cu(S$^t$Bu)$_3$In(N$^i$Pr$_2$); (N$^i$Pr$_2$)Cu(Se$^t$Bu)$_3$In(NEt$_2$); (NEt$_2$)Cu(S$^t$ Bu)$_3$In(N$^i$Pr$_2$); (NEt$_2$)Cu(Se$^t$Bu)$_3$Ga(N$^i$Pr$_2$); (N$^i$Pr$_2$)Cu(S$^t$Bu)$_3$Ga(N$^i$Pr$_2$); (N$^i$Pr$_2$)Cu(Se$^t$Bu)$_3$In(N$^n$Bu$_2$); and (N$^i$Pr$_2$)Cu(Se$^t$Bu)$_3$In(N$^s$Bu$_2$).

Preparation of Molecular Precursors (MP3)

Embodiments of this invention provide a family MP3 of precursor molecules which can be synthesized from a compound containing an atom M$^B$ of Group 13 selected from Al, Ga, In, and Tl, and a compound containing a divalent atom M$^A$. Divalent metal atoms M$^A$ include Cu, Zn, Cd, Pt, Pd, Mo, W, Cr, Ni, Mn, Fe, Co, V, and Hg.

Advantageously facile routes for the synthesis and isolation of molecular precursor compounds of this invention are described below.

In some aspects, synthesis of a molecular precursor of the MP3 family begins with providing a compound having the formula R$^1_2$M$^B$ER$^2$.

A compound having the formula R$^1_2$M$^B$ER$^2$ containing a Group 13 atom M$^B$ can be prepared by reacting M$^B$R$^1_3$ with HER$^2$, where R$^1$, R$^2$, and E are as defined above.

In other variations, a compound having the formula R$^1_2$M$^B$ER$^2$ containing a Group 13 atom M$^B$ can be prepared by reacting R$^1_2$M$^B$X with M$^C$ER$^2$, where R$^1$, R$^2$ and E are as defined above, X is halogen, and M$^C$ is an alkali metal.

In additional variations, a compound having the formula R$^1_2$M$^B$ER$^2$ containing a Group 13 atom M$^B$ can be prepared by reacting R$^1_2$M$^B$X with R$^2$ESi(CH$_3$)$_3$, where R$^1$, R$^2$ and E are as defined above, and X is halogen.

To prepare a molecular precursor of the MP3 family, the compound R$^1_2$M$^B$ER$^2$ may be reacted with a compound containing a divalent atom M$^A$ defined above.

In some embodiments, a compound R$^1_2$M$^B$ER$^2$ can be contacted with a chalcogen-containing compound M$^A$(ER$^3$)$_2$ or M$^A$(ER$^3$)(ER$^4$) in the presence of one equivalent of HER$^5$, where M$^A$, M$^B$, E, R$^1$R$^2$, R$^3$, R$^4$, and R$^5$ are as defined above.

As shown in Reaction Scheme 3a, in some embodiments, M$^B$R$^1_3$ can be reacted with HER$^2$ to form R$^1_2$M$^B$ER$^2$. The product R$^1_2$M$^B$ER$^2$ can be contacted with a compound M$^A$(ER$^3$)(ER$^4$) in the presence of one equivalent of HER$^5$ to form a molecular precursor compound having the formula (R$^4$E)M$^A$(ER$^3$)(ER$^5$)(ER$^2$)M$^B$R$^1$.

REACTION SCHEME 3a:

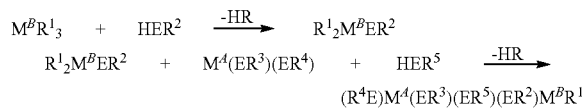

In Reaction Scheme 3a, for each occurrence, E may be S, Se, or Te. In certain variations, the starting compound M$^B$R$_3$ may be stabilized by a ligand such as diethylether.

Alternatively, in some embodiments, M$^B$R$^1_3$ can be reacted with a compound M$^A$(ER$^3$)(ER$^4$) in the presence of two equivalents of HER″ (HER$^2$ and HER$^5$ in Reaction Scheme 3b) to form a molecular precursor compound having the formula (R$^4$E)M$^A$(ER″)$_2$(ER$^3$)M$^B$R$^1$.

As shown in Reaction Scheme 3b, in some embodiments, M$^B$R$^1_3$ can be reacted with compounds M$^A$(ER$^3$)(ER$^4$), HER$^2$, and HER$^4$ to form a molecular precursor compound having the formula (R$^4$E)M$^A$(ER$^3$)(ER$^5$)(ER$^2$)M$^B$R$^1$.

REACTION SCHEME 3b:

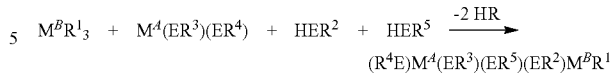

In Reaction Scheme 3b, each of the reagents HER$^2$ and HER$^5$ can itself be a mixture of compounds with different R″ groups, where n is 1, 2, 3, 4, or 5, so that each group R″ can be independently different. Further, some of the groups -ER″ may be exchanged with each other during the reaction. Thus, the order of appearance of the groups R″ in the formula (R$^4$E)M$^A$(ER$^3$)(ER$^5$)(ER$^2$)M$^B$R$^1$, can be different.

In further aspects, a compound (NR$^1_2$)M$^B$R$^2_2$ can be contacted with a chalcogen-containing compound M$^A$(ER$^3$)(ER$^4$) in the presence of two equivalents of HER$^5$, where M$^A$, M$^B$, E, R$^1$, R$^2$, R$^3$, R$^4$, and R$^5$ are as defined above, and NR$^1_2$ is amido.

As shown in Reaction Scheme 3c, (NR$^1_2$)M$^B$R$^2_2$ can be reacted with M$^A$(ER$^3$)(ER$^4$) in the presence of two equivalents of HER$^5$ to form a molecular precursor compound having the formula (R$^4$E)M$^A$(ER$^3$)(ER$^5$)$_2$M$^B$(NR$^1_2$).

REACTION SCHEME 3c:

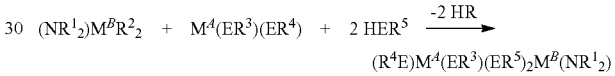

In further embodiments, to prepare a molecular precursor of the MP3 family, the compound R$^1_2$M$^B$ER$^2$ may be reacted with a compound containing a divalent atom M$^A$ defined above.

In some embodiments, a compound R$^1_2$M$^B$ER$^2$ can be contacted with a chalcogen-containing compound M$^A$(R$^5$)(ER$^4$) in the presence of one equivalent of HER$^5$, where M$^A$, M$^B$, E, R$^1$, R$^2$, R$^3$, R$^4$, and R$^5$ are as defined above.

As shown in Reaction Scheme 3d, in some embodiments, M$^B$R$^1_3$ can be reacted with HER$^2$ to form R$^1_2$M$^B$ER$^2$. The product R$^1_2$M$^B$ER$^2$ can be contacted with a compound M$^A$(R$^5$)(ER$^4$) in the presence of one equivalent of HER$^3$ to form a molecular precursor compound having the formula (R$^5$)M$^A$(ER$^4$)(ER$^3$)(ER$^2$)M$^B$R$^1$.

REACTION SCHEME 3d:

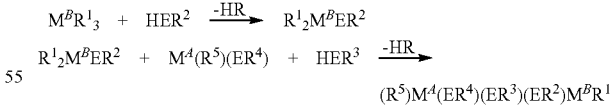

Alternatively, in some embodiments, M$^B$R$^1_3$ can be reacted with a compound M$^A$(R$^5$)(ER$^4$) in the presence of two equivalents of HER″ (HER$^2$ and HER$^3$ in Reaction Scheme 3e) to form a molecular precursor compound having the formula) (R$^5$)M$^A$(ER″)$_2$(ER$^3$)M$^B$R$^1$.

As shown in Reaction Scheme 3e, in some embodiments, M$^B$R$^1_3$ can be reacted with compounds M$^A$(R$^5$)(ER$^4$), HER$^2$, and HER$^3$ to form a molecular precursor compound having the formula (R$^5$)M$^A$(ER$^4$)(ER$^3$)(ER$^2$)M$^B$R$^1$.

REACTION SCHEME 3e:

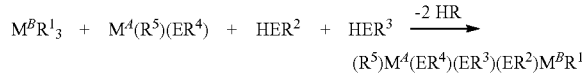

In further aspects, a compound $M^B R^1_3$ can be contacted with a chalcogen-containing compound $M^A(NR^5_2)(ER^4)$ in the presence of two equivalents of $HER^3$, where $M^A$, $M^B$, E, $R^1$, $R^2$, $R^3$, $R^4$, and $R^5$ are as defined above, and $NR^3_2$ is amido.

As shown in Reaction Scheme 3f, $M^B R^1_3$ can be reacted with $M^A(NR^5_2)(ER^4)$ in the presence of two equivalents of $HER^3$ to form a molecular precursor compound having the formula $(NR^5_2)M^A(ER^4)(ER^3)_2M^B R^1_2$.

REACTION SCHEME 3f:

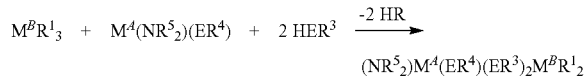

The reactions and manipulations of reagents can be carried out using known techniques under controlled inert atmosphere, such as dry nitrogen, and anaerobic conditions using a drybox and a Schlenk line system.

Molecular Precursors (MP4) for Semiconductors and Optoelectronics

In some embodiments, a molecular precursor compound of the MP4 family contains an atom $M^B$ of Group 13 selected from Al, Ga, In, and Tl, which is stabilized by having ligands attached. These molecular precursor compounds further contain a monovalent or divalent atom $M^A$ which is stabilized by having ligands attached.

Figure 5:
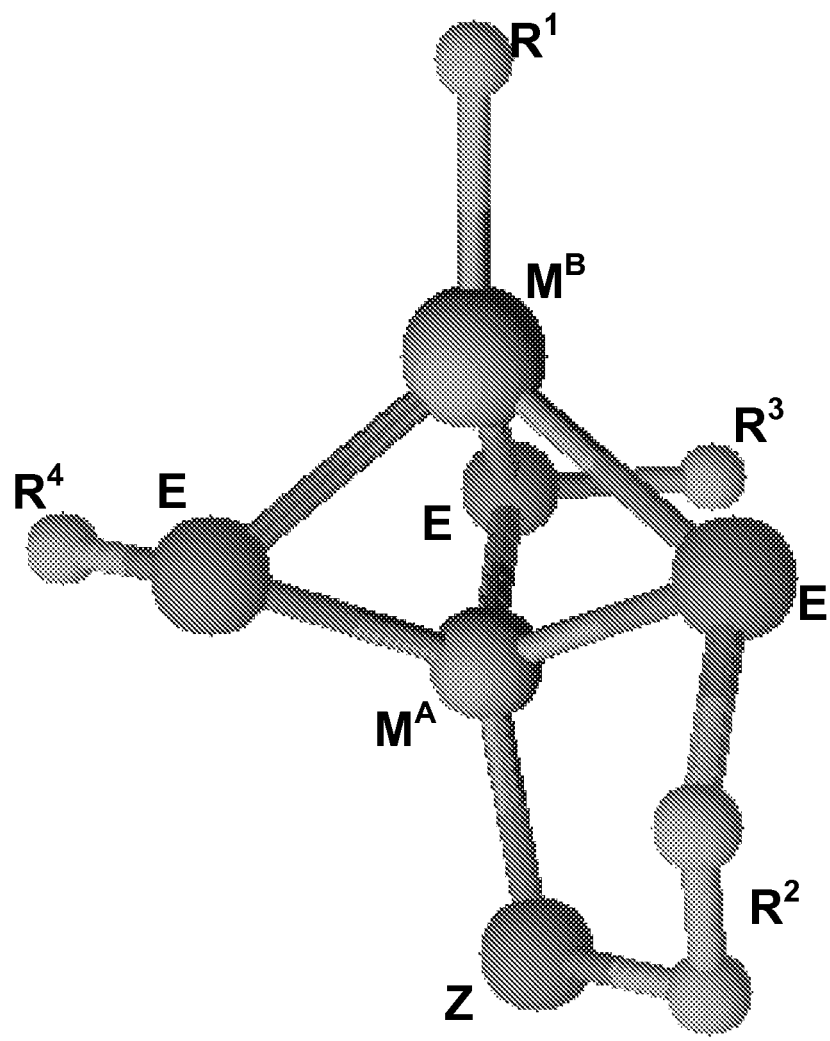
FIG. 5.

The structure of a family of precursor molecules MP4 is shown in FIG. 5 and may be represented by the formula $M^A(ER^2Z)(ER^3)(ER^4)M^B R^1$, where E is chalcogen, Z is a neutral or anionic moiety, or portion of a ligand, which may be capable of binding to a metal atom, and $R^1$, $R^2$, $R^3$ and $R^4$ are the same or different and are groups attached through one or more carbon or non-carbon atoms, including alkyl, aryl, heteroaryl, alkenyl, amido, silyl, and inorganic and organic ligands.

The general structure of a precursor molecule of the MP4 family can be represented by the formula $M^A(ER^2Z)(ER^3)(ER^4)M^B R^1$, as shown in FIG. 5.

As shown in FIG. 5, the local structure surrounding the atom $M^B$ is a tetrahedral arrangement of four atoms. At one apex of the $M^B$ tetrahedron is an atom of $R^1$ through which it is attached to $M^B$. The remainder of the tetrahedron is formed by the chalcogen atoms of three ligands $(ER^2Z)$, $(ER^3)$, and $(ER^4)$, each of which is attached through a chalcogen atom to an $M^B$.

As shown in FIG. 5, the local structure surrounding the atom $M^A$ is a tetrahedral arrangement of four atoms. At one apex of the $M^A$ tetrahedron is an atom of the moiety Z, through which it is attached to $M^A$. The remainder of the tetrahedron is formed by the chalcogen atoms of three ligands $(ER^2Z)$, $(ER^3)$, and $(ER^4)$, each of which is attached through a chalcogen atom to $M^A$. The three ligands $(ER^2Z)$, $(ER^3)$, and $(ER^4)$ are chalcogen bridging ligands that are each shared through bonding of their chalcogen atom to $M^A$ and $M^B$.

As shown in FIG. 5, the ligand $(ER^2Z)$ contains the moiety Z attached through the portion $R^2$. Thus, the ligand $(ER^2Z)$ is essentially a bidentate ligand that is attached to $M^A$ through both its chalcogen atom E, and through an atom of the moiety Z.

The portion $R^n$, where n=1-4, of each of the ligands attached to the atoms $M^A$ and $M^B$ may be a good leaving group in relation to a transition of the molecular precursor compound at elevated temperatures or upon application of energy.

The arrangement of atoms in a molecular precursor compound of the MP4 family may be described by the formula $M^A(ER^2Z)(ER^3)(ER^4)M^B R^1$, where E is chalcogen, and $R^1$, $R^2$, $R^3$, and $R^4$ are the same or different and are groups attached through a carbon or non-carbon atom, including alkyl, aryl, heteroaryl, alkenyl, amido, silyl, and inorganic and organic ligands. In some embodiments, $R^1$, $R^2$, $R^3$, and $R^4$ are the same or different and are alkyl groups attached through a carbon atom.

In some embodiments, Z is a neutral moiety such as —$NR_2$, —$PR_2$, —$AsR_2$, -ER, —SR, —OR, and —SeR. When Z is a neutral moiety, the ligand $(ER^2Z)$ is a bidentate ligand such as $ER^2NR_2$, $ER^2PR_2$, $ER^2AsR_2$, $ER^2SR$, and $ER^2SeR$, each of which can bond to $M^A$ through the atom E and a second atom such as N, P, As, S, Se, and oxygen. When Z is a neutral ligand, $M^A$ is a monovalent metal atom selected from Cu, Au, Ag, and Hg.

In some variations, Z is an anionic moiety such as —$NR^-$, -$E^-$, —$O^-$, —$R^-$, -$ERNR^-$, -$ERE^-$, and —$SiR_2^-$. When Z is an anionic moiety, the ligand $(ER^2Z)$ is a bidentate ligand such as $ER^2NR^-$, $ER^2PR^-$, $ER^2AsR^-$, $ER^2S^-$, $ER^2O^-$, and $ER^2Se^-$, each of which can bond to $M^A$ through E and a second atom such as N, P, As, S, Se, and O. When Z is an anionic moiety, $M^A$ is a divalent metal atom. Divalent metal atoms $M^A$ include Cu, Zn, Cd, Pt, Pd, Mo, W, Cr, Ni, Mn, Fe, Co, V, and Hg.

When Z is an anionic moiety and $M^A$ is a divalent metal atom, examples of the ligand $(ER^4Z)$ include —$SCH_2CH_2NR$—, —$SCH_2CH_2S$—, —$SCH_2CH_2Se$—, —$SeCH_2CH_2NR$—, —$SeCH_2CH_2S$—, —$SeCH_2CH_2Se$—, —$SeCH_2CH_2CH_2NR$—, and —$SeCH_2CH_2CH_2O$—.

Embodiments of this invention further provide a family MP4 of molecular precursor compounds in which the arrangement of atoms may be described by the formula $Cu(ER^2Z)(ER^3)(ER^4)(In,Ga)R^1$, wherein E is chalcogen, $R^1$, $R^2$, $R^3$ and $R^4$ are the same or different and are groups attached through one or more carbon or non-carbon atom, including alkyl, aryl, heteroaryl, alkenyl, amido, silyl, and inorganic and organic ligands. Z is as defined above.

In certain variations, a molecular precursor compound of the MP4 family has the arrangement of atoms described by the formula $Cu(ER^2Z)(ER^3)(ER^4)(In,Ga)R^1$, wherein E is S or Se, $R^1$, $R^3$, $R^4$ and Z are as defined above, and $R^2$ is —$(CH_2)_n$—. As used herein, the term alkyl includes the term alkylene or —$(CH_2)_n$—.

In certain variations, a molecular precursor compound of the MP4 family contains an atom $M^B$, being In or Ga, which is stabilized by attached ligands. These molecular precursor compounds further contain an atom $M^A$, being Cu, which is stabilized by interactions with one or more chalcogen atoms and the moiety Z as defined above.

In further embodiments, the groups $R^1$, $R^2$, $R^3$ and $R^4$ may independently be (C1-22)alkyl groups. In these embodiments, the alkyl group may be a (C1)alkyl(methyl), or a (C2)alkyl(ethyl), or a (C3)alkyl, or a (C4)alkyl, or a (C5)alkyl, or a (C6)alkyl, or a (C7)alkyl, or a (C8)alkyl, or a (C9)alkyl, or a (C10)alkyl, or a (C11)alkyl, or a (C12)alkyl, or a (C13)alkyl, or a (C14)alkyl, or a (C15)alkyl, or a (C16)alkyl, or a (C17)alkyl, or a (C18)alkyl, or a (C19)alkyl, or a (C20)alkyl, or a (C21)alkyl, or a (C22)alkyl.

In certain embodiments, the groups $R^1$, $R^2$, $R^3$ and $R^4$ may independently be (C1-12)alkyl groups. In these embodiments, the alkyl group may be a (C1)alkyl(methyl), or a (C2)alkyl(ethyl), or a (C3)alkyl, or a (C4)alkyl, or a (C5)alkyl, or a (C6)alkyl, or a (C7)alkyl, or a (C8)alkyl, or a (C9)alkyl, or a (C10)alkyl, or a (C11)alkyl, or a (C12)alkyl.

In certain embodiments, the groups $R^1$, $R^2$, $R^3$ and $R^4$ may independently be (C1-6)alkyl groups. In these embodiments, the alkyl group may be a (C1)alkyl(methyl), or a (C2)alkyl (ethyl), or a (C3)alkyl, or a (C4)alkyl, or a (C5)alkyl, or a (C6)alkyl.

In further variations, $R^1$ is (C8)alkyl and $R^2$, $R^3$ and $R^4$ are the same and are (C3-4)alkyl.

In other forms, $R^1$ is (C6)alkyl and $R^2$, $R^3$ and $R^4$ are the same and are (C3-4)alkyl.

A molecular precursor compound of the MP4 family may be crystalline, or non-crystalline.

Examples of molecular precursor compounds of the MP4 family of this disclosure include compounds having any one of the formulas: $Cu(S(CH_2)_2Se)(S^tBu)(S''Bu)In^iPr$; $Cu(S(CH_2)_2Se)(S^tBu)(S^tBu)In''Bu$; $Cu(Se(CH_2)_2NEt)(Se^tBu)(Se''Bu)In''Bu$; $Cu(Se(CH_2)_2NMe)(Se^tBu)(Se^tBu)In''Bu$; $Cu(Se(CH_2)_2N(Phenyl))(Se^tBu)(Se''Bu)Ga^tBu$; $Cu(Se(CH_2)_2N^tBu)(Se^tBu)_2Ga^tBu$; $Cu(Se(CH_2)_2Se)(Se^tBu)(Se''Bu)In^tBu$; and $Cu(Se(CH_2)_2Se)(Se^tBu)_2In^iPr$.

Examples of molecular precursor compounds of the MP4 family of this disclosure include compounds having any one of the formulas: $Cu(S(CH_2)_2N^tBu)(S^tBu)(S''Bu)Ga^iPr$; $Cu(S(CH_2)_2N^iPr)(S^tBu)(S''Bu)Tl''Bu$; $Cu(Se(CH_2)_2N^tBu)(S^tBu)(S''Bu)Ga''Bu$; $Cu(S(CH_2)_2N^iPr(S^tBu)(S''Bu)Tl^tBu$; $Cu(Se(CH_2)_2N^tBu)(S^tBu)(S''Bu)Tl^tBu$; and $Cu(Se(CH_2)_2N^iPr)(S^tBu)(S''Bu)Ga^iPr$.

Examples of molecular precursor compounds of the MP4 family of this disclosure include compounds having any one of the formulas: $Cu(Se(CH_2)_3^-)(S^tBu)_2In^tBu$ and $Cu(Se^iPr)(S^tBu)_2In^tBu$.

Examples of molecular precursor compounds of the MP4 family of this disclosure include compounds having any one of the formulas: $Zn(S(CH_2)_2N^tBu)(S^tBu)(S''Bu)In^iPr$; $Cd(S(CH_2)_2S)(S^tBu)(S''Bu)In''Bu$; and $Hg(S(CH_2)_2N^iPr)(S^tBu)(S''Bu)Ga^tBu$.

Examples of molecular precursor compounds of the MP4 family of this disclosure include compounds having any one of the formulas: $Cu(S(CH_2)_2N^tBu_2)_2(S''Bu)In^iPr$; $Cu(S(CH_2)_2N^tBu_2)_2(S^iPr)In''Bu$; $Cu(S(CH_2)_2SR)_2(Se^iPr)In^iPr$; $Cu(Te(CH_2)_2SeR)_2(Se^iPr)In''Bu$; $Cu(Se(CH_2)_2SeR)_2(Te^iPr)In''Bu$; and $Cu(S(CH_2)_2SeR)_2(Te^iPr)In^tBu$.

Examples of molecular precursor compounds of the MP4 family of this disclosure include compounds having any one of the formulas: $Au(S(CH_2)_2N^iPr_2)_2(S''Bu)In^iPr$; $Ag(S(CH_2)_2N^tBu_2)_2(S^iPr)In''Bu$; $Hg(S(CH_2)_2SR)_2(Se^iPr)In^iPr$; $Au(Te(CH_2)_2SeR)_2(Se^iPr)In''Bu$; $Cu(Se(CH_2)_2SeR)_2(Te^iPr)In''Bu$; and $Cu(S(CH_2)_2SeR)_2(Te^iPr)In^tBu$.

Examples of molecular precursor compounds of the MP4 family of this disclosure include compounds having any one of the formulas: $Cu(S(CH_2)_2N^tBu_2)(S^iPr)(S''Bu)In^iPr$; $Cu(Se(CH_2)_2SeR)(S^iPr)(S''Bu)In''Bu$; $Cu(Se(CH_2)_2SR)(S^iPr)(Te''Bu)In^tBu$; and $Cu(Se(CH_2)_2N^iPr_2)(Se^iPr)(Se''Bu)In^iPr$.

Examples of molecular precursor compounds of the MP4 family of this disclosure include compounds having any one of the formulas: $Cu(S(CH_2)_2N^tBu_2)_3In(n\text{-octyl})$; $Cu(S(CH_2)_2SeR)_3In(n\text{-dodecyl})$; $Cu(Se(CH_2)_2SeR)_3In(\text{branched-C18})$; and $Cu(S(CH_2)_2N^tBu_2)_3In(\text{branched-C22})$.

Preparation of Molecular Precursors (MP4)

Embodiments of this invention provide a family of MP4 precursor molecules which can be synthesized from a compound containing an atom $M^B$ of Group 13 selected from Al, Ga, In, and Tl, and a compound containing a monovalent or divalent atom $M^A$. Monovalent atoms $M^A$ include Cu, Au, Ag, and Hg. Divalent atoms $M^A$ include Cu, Zn, Cd, Pt, Pd, Mo, W, Cr, Ni, Mn, Fe, Co, V, and Hg.

Advantageously facile routes for the synthesis and isolation of molecular precursor compounds of this invention are described below.

In some aspects, synthesis of a molecular precursor of the MP4 family begins with providing a compound having the formula $R^1_2M^BER^2Z$.

A compound having the formula $R^1_2M^BER^2Z$ containing a Group 13 atom $M^B$ can be prepared by reacting $M^BR^1_3$ with $HER^2Z$, where $R^1$, $R^2$, $R^3$, E, and Z are as defined above.

In other variations, a compound having the formula $R^1_2M^BER^2Z$ containing a Group 13 atom $M^B$ can be prepared by reacting $R^1_2M^BX$ with $M^CER^2Z$, where $R^1$, $R^2$ and E are as defined above, X is halogen, and $M^C$ is an alkali metal.

To prepare a molecular precursor of the MP4 family with a monovalent atom $M^A$, the compound $R^1_2M^BER^2Z ER^2Z$ may be reacted with a compound containing a monovalent atom $M^A$ defined above.

In some embodiments, a compound $R^1_2M^BER^2Z$ can be contacted with a chalcogen-containing compound $M^A(ER^3)$ in the presence of $HER^4$, where $M^A$, $M^B$, E, $R^1$, $R^2$, $R^3$, and $R^4$ are as defined above.

As shown in Reaction Scheme 4a, in some embodiments, $M^BR^1_3$ can be reacted with $HER^2Z$ to form $R^1_2M^BER^2Z$. The product $R^1_2M^BER^2Z$ can be contacted with a compound $M^A(ER^3)$ in the presence of $HER^4$ to form a molecular precursor compound having the formula $M^A(ER^2Z)(ER^3)(ER^4)M^BR^1$. Z is a neutral moiety in Reaction Scheme 4a.

REACTION SCHEME 4a:

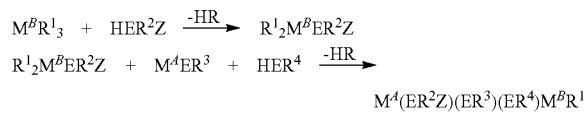

Alternatively, in some embodiments, as shown in Reaction Scheme 4b, $M^BR^1_3$ can be reacted with compounds $M^A(ER^3)$, $HER^2Z$, and $HER^4$ to form a molecular precursor compound having the formula $M^A(ER^2Z)(ER^3)(ER^4)M^BR^1$. Z is a neutral moiety in Reaction Scheme 4b.

REACTION SCHEME 4b:

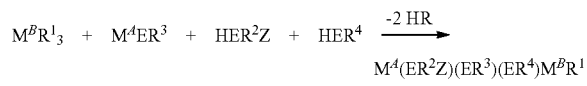

To prepare a molecular precursor of the MP4 family with a divalent atom $M^A$, the compound $M^AER^3Z$ may be reacted with a compound containing an atom $M^B$ defined above.

In some embodiments, a compound $R^1_2M^BER^2$ can be contacted with a chalcogen-containing compound $M^AER^3Z$ in the presence of one equivalent of $HER^4$, where $M^A$, $M^B$, E, $R^1$, $R^2$, $R^3$, and $R^4$ are as defined above.

As shown in Reaction Scheme 4c, in some embodiments, $M^BR^1_3$ can be reacted with $HER^2$ to form $R^1_2M^BER^2$. The product $R^1_2M^BER^2$ can be contacted with a compound $M^AER^3Z$ in the presence of $HER^4$ to form a molecular precursor compound having the formula $M^4(ER^3Z)(ER^2)(ER^4)M^BR^1$. Z is a anionic moiety in Reaction Scheme 4c.

REACTION SCHEME 4c:

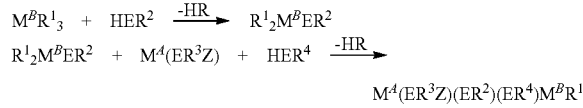

To prepare a molecular precursor of the MP4 family, in additional embodiments, the following Reaction Schemes 4d, 4e, and 4f may be used.

REACTION SCHEME 4d:

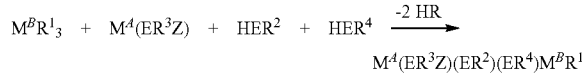

Z is an anionic moiety in Reaction Scheme 4d.

REACTION SCHEME 4e:

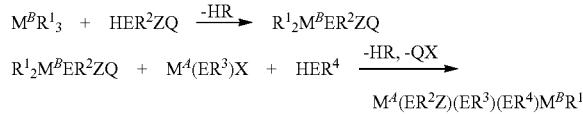

Q is a leaving group including $SiRN_3$, wherein R is alkyl. X in Reaction Schemes 4e and 4f is a leaving group including halogen.

REACTION SCHEME 4f:

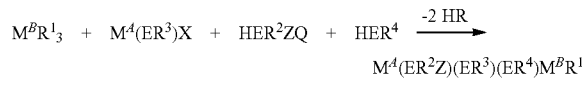

The reactions and manipulations of reagents can be carried out using known techniques under controlled inert atmosphere, such as dry nitrogen, and anaerobic conditions using a drybox and a Schlenk line system.

Molecular Precursors (MP1-Ag) for Semiconductors and Optoelectronics

In some embodiments, a molecular precursor compound of the family MP1-Ag contains an atom $M^B$ of Group 13 selected from Al, Ga, In, and Tl, which is stabilized by having ligands attached. These molecular precursor compounds further contain a monovalent silver (Ag) atom $M^4$, which is stabilized by interactions with one or more chalcogen atoms. The atom $M^4$ may further be stabilized by interacting with another $M^4$ atom. Aside from interactions with chalcogen atoms, the atom $M^4$ has no other ligands attached.

The structure of a family of MP1-Ag precursor molecules represented by the formula $M^4$-$(ER^2)(ER^3)(ER^4)M^BR^1$ is shown in FIG. 1.

The molecular structure of the family of compounds is of a dimer, represented by the formula $(M^4$-$(ER^2)(ER^3)(ER^4)M^BR^1)_2$.

The local structure surrounding the atom $M^B$ in a molecule of the MP1-Ag family is a tetrahedral arrangement of four atoms. At one apex of the $M^B$ tetrahedron is an atom of $R^1$ through which it is attached to $M^B$. The remainder of the tetrahedron is formed by the chalcogen atoms of three of the ligands $(ER^2)$, $(ER^3)$, and $(ER^4)$, each of which is attached through a chalcogen atom to $M^B$.

The local structure surrounding the atom $M^4$ includes bonding interactions with three chalcogen atoms that belong to three of the ligands $(ER^2)$, $(ER^3)$, and $(ER^4)$. The three ligands $(ER^2)$, $(ER^3)$, and $(ER^4)$, are chalcogen bridging ligands that are each shared through bonding of their chalcogen atom to an $M^4$ atom and an $M^B$ atom. The atom $M^4$ may further be stabilized by interacting with another $M^4$ atom. Aside from interactions with chalcogen atoms, the atom $M^4$ has no other ligands attached.

The portion $R^n$, where n is 1, 2, 3, or 4, of each of the ligands attached to the atoms $M^4$ and $M^B$ may be a good leaving group in relation to a transition of the molecular precursor compound at elevated temperatures or upon application of energy.

The arrangement of atoms in a molecular precursor compound of the MP1-Ag family may be described by the formula $M^4$-$(ER^2)(ER^3)(ER^4)M^BR^1$, wherein E is chalcogen, and $R^1$, $R^2$, $R^3$, and $R^4$ are the same or different and are groups attached through a carbon or non-carbon atom, including alkyl, aryl, heteroaryl, alkenyl, amido, silyl, and inorganic and organic ligands. In some embodiments, $R^1$, $R^2$, $R^3$, and $R^4$ are the same or different and are alkyl groups attached through a carbon atom.

In some embodiments, molecular precursor compounds of the MP1-Ag family advantageously do not contain a phosphine ligand, and do not contain a ligand or attached compound containing phosphorus, arsenic, or antimony, or a halogen ligand.

Embodiments of this invention further provide a family MP1-Ag of molecular precursor compounds in which the arrangement of atoms may be described by the formula Ag-$(ER^2)(ER^3)(ER^4)(In,Ga)R^1$, wherein E is chalcogen, and $R^1$, $R^2$, $R^3$, and $R^4$ are the same or different and are groups attached through a carbon or non-carbon atom, including alkyl, aryl, heteroaryl, alkenyl, amido, silyl, and inorganic and organic ligands. In some embodiments, $R^1$, $R^2$, $R^3$, and $R^4$ are the same or different and are alkyl groups attached through a carbon atom.

In certain variations, a molecular precursor compound of the MP1-Ag family contains an atom $M^B$, being In or Ga, which is stabilized by attached ligands. These molecular precursor compounds further contain an atom $M^4$, being Ag, which is stabilized by interactions with one or more chalcogen atoms. The atom $M^4$ may further be stabilized by interacting with another $M^4$ atom. Aside from interactions with chalcogen atoms, the atom $M^4$ has no other ligands attached.

In additional aspects, a molecular precursor compound may have the formula $(M^{41}$-$(ER^1)(ER^2)(ER^3)M^BR^4)(M^{42}$-$(ER^1)(ER^2)(ER^3)M^BR^4)$, wherein $M^{41}$ is Ag and $M^{42}$ is Cu, Au or a mixture thereof.

In further embodiments, the groups $R^1$, $R^2$, $R^3$, and $R^4$ may independently be (C1-22)alkyl groups. In these embodiments, the alkyl group may be a (C1)alkyl(methyl), or a (C2)alkyl(ethyl), or a (C3)alkyl, or a (C4)alkyl, or a (C5)alkyl, or a (C6)alkyl, or a (C7)alkyl, or a (C8)alkyl, or a (C9)alkyl, or a (C10)alkyl, or a (C11)alkyl, or a (C12)alkyl, or a (C13)alkyl, or a (C14)alkyl, or a (C15)alkyl, or a (C16)alkyl, or a (C17)alkyl, or a (C18)alkyl, or a (C19)alkyl, or a (C20)alkyl, or a (C21)alkyl, or a (C22)alkyl.

In certain embodiments, the groups $R^1$, $R^2$, $R^3$, and $R^4$ may independently be (C1-12)alkyl groups. In these embodiments, the alkyl group may be a (C1)alkyl(methyl), or a (C2)alkyl(ethyl), or a (C3)alkyl, or a (C4)alkyl, or a (C5) alkyl, or a (C6)alkyl, or a (C7)alkyl, or a (C8)alkyl, or a (C9)alkyl, or a (C10)alkyl, or a (C11)alkyl, or a (C12)alkyl.

In certain embodiments, the groups $R^1$, $R^2$, $R^3$, and $R^4$ may independently be (C1-6)alkyl groups. In these embodiments, the alkyl group may be a (C1)alkyl(methyl), or a (C2)alkyl (ethyl), or a (C3)alkyl, or a (C4)alkyl, or a (C5)alkyl, or a (C6)alkyl.

In further variations, $R^1$ is (C8)alkyl and $R^2$, $R^3$, and $R^4$ are the same and are (C3-4)alkyl.

In other forms, $R^1$ is (C6)alkyl and $R^2$, $R^3$, and $R^4$ are the same and are (C3-4)alkyl.

In some aspects, a molecular precursor compound can be represented by the formula $(M^A\text{-}(ER^2)(ER^3)(ER^4)M^BR^1)_2$, referred to as a dimer, wherein $M^A$ is Ag, which is stabilized by interactions with one or more chalcogen atoms. The atom $M^A$ may further be stabilized by interacting with another $M^A$ atom. Aside from interactions with chalcogen atoms, the atom $M^A$ has no other ligands attached. $M^B$ is an atom of Ga or In, each E is independently S or Se, and $R^1$, $R^2$, $R^3$, and $R^4$ are as defined above.

A molecular precursor compound of the MP1-Ag family may be crystalline, or non-crystalline.

Examples of molecular precursor compounds of the MP1-Ag family of this disclosure include compounds having any one of the formulas: Ag—$(S^tBu)_3In^iPr$; Ag—$(S^tBu)_3In^nBu$; Ag—$(Se^tBu)_3In^nBu$; Ag—$(S^tBu)_3In^tBu$; Ag—$(Se^tBu)_3Ga^nBu$; Ag—$(Se^tBu)_3Ga^sBu$; Ag—$(Se^tBu)_3Ga^tBu$; Ag—$(S^tBu)_3Ga^tBu$; Ag—$(Se^tBu)_3In^tBu$; Ag—$(Se^tBu)_3In^iPr$; Ag—$(Se^tBu)_3In^sBu$; Ag—$(Se^tBu)_3Ga^iPr$; Ag—$(S^tBu)_3Ga^iPr$; and a dimer of any of the foregoing.

Examples of molecular precursor compounds of the MP1-Ag family of this disclosure include compounds having any one of the formulas: Ag—$(S^tBu)_3Tl^iPr$; Ag—$(S^tBu)_3Tl^nBu$; Ag—$(Se^tBu)_3Tl^nBu$; Ag—$(S^tBu)_3Tl^tBu$; Ag—$(Se^tBu)_3Tl^tBu$; Ag—$(Se^tBu)_3Tl^iPr$; and a dimer of any of the foregoing.

Examples of molecular precursor compounds of the MP1-Ag family of this disclosure include compounds having any one of the formulas: Ag—$(S^nBu)_2(S^tBu)In^nBu$; Ag—$(S^tBu)_2(S^nBu)In^iPr$; Ag—$(S^tBu)_2(S^iPr)In^nBu$; Ag—$(S^tBu)_2(Se^iPr)In^iPr$; Ag-$(Te^tBu)_2(Se^iPr)In^nBu$; Ag—$(Se^tBu)_2(Te^iPr)In^nBu$; Ag—$(S^tBu)_2(Te^iPr)In^tBu$; and a dimer of any of the foregoing.

Examples of molecular precursor compounds of the MP1-Ag family of this disclosure include compounds having any one of the formulas: Ag—$(S^tBu)(S^iPr)(S^nBu)In^iPr$; Ag—$(Se^tBu)(S^iPr)(S^nBu)In^nBu$; Ag—$(Se^tBu)(S^iPr)(Te^nBu)In^nBu$; Ag—$(Se^tBu)(Se^iPr)(Se^nBu)In^iPr$; and a dimer of any of the foregoing.

Examples of molecular precursor compounds of the MP1-Ag family of this disclosure include compounds having any one of the formulas: Ag—$(S^tBu)_3In(n\text{-}octyl)$; Ag—$(S^tBu)_3In(n\text{-}dodecyl)$; Ag—$(Se^tBu)_3In(branched\text{-}C18)$; Ag—$(S^tBu)_3In(branched\text{-}C22)$; Ag—$(Se(n\text{-}hexyl))_3Ga^tBu$; Ag—$(S(n\text{-}octyl))_3Ga^tBu$; and a dimer of any of the foregoing.

As used herein, the term dimer refers to a molecule composed of two moieties having the same empirical formula. For example, $(Ag—(S^tBu)_3In^iPr)_2$ is a dimer of Ag—$(S^tBu)_3In^iPr$.

Preparation of Molecular Precursors (MP1-Ag)

Embodiments of this invention provide a family MP1-Ag of precursor molecules which can be synthesized from a compound containing an atom $M^B$ of Group 13 selected from Al, Ga, In, and Tl, and a compound containing a monovalent silver (Ag) atom $M^A$.

Advantageously facile routes for the synthesis and isolation of molecular precursor compounds of this invention have been discovered, as described below.

In some aspects, synthesis of a molecular precursor of the MP1-Ag family begins with providing a compound having the formula $R^1{}_2M^BER^2$.

A compound having the formula $R^1{}_2M^BER^2$ containing a Group 13 atom $M^B$ can be prepared by reacting $M^BR^1{}_3$ with $HER^2$, where $R^1$, $R^2$, and E are as defined above.

In other variations, a compound having the formula $R^1{}_2M^BER^2$ containing a Group 13 atom $M^B$ can be prepared by reacting $R^1{}_2M^BX$ with $M^CER^2$, where $R^1$, $R^2$ and E are as defined above, X is halogen, and $M^C$ is an alkali metal.

In additional variations, a compound having the formula $R^1{}_2M^BER^2$ containing a Group 13 atom $M^B$ can be prepared by reacting $R^1{}_2M^BX$ with $R^2ESi(CH_3)_3$, where $R^1$, $R^2$ and E are as defined above, and X is halogen.

To prepare a molecular precursor of the MP1-Ag family, the compound $R^1{}_2M^BER^2$ may be reacted with a compound containing a monovalent silver (Ag) atom $M^A$.

In some embodiments, a compound $R^1{}_2M^BER^2$ can be contacted with a chalcogen-containing compound $M^A(ER^3)$ in the presence of one equivalent of $HER^4$, where $M^A$, $M^B$, E, $R^1$, $R^2$, $R^3$, and $R^4$ are as defined above. As shown in Reaction Scheme 5a, $M^BR^1{}_3$ can be reacted with $HER^2$ to form $R^1{}_2M^BER^2$. The product $R^1{}_2M^BER^2$ can be contacted with a compound $M^A(ER^3)$ in the presence of one equivalent of $HER^4$ to form a molecular precursor compound having the formula $M^A\text{-}(ER^2)(ER^3)(ER^4)M^BR^1$.

REACTION SCHEME 5a:

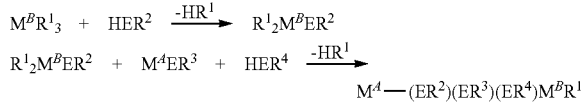

In Reaction Scheme 5a, for each occurrence, E may be S, Se, or Te.

In certain variations, the starting compound $M^BR^1{}_3$ may be stabilized as an adduct, for example, as the diethylether adduct, and the diethyl ether may be removed.

Alternatively, in some embodiments, $M^BR^1{}_3$ can be reacted with a compound $M^A(ER^3)$ in the presence of two equivalents of $HER^2$ to form a molecular precursor compound having the formula $M^A\text{-}(ER^2)_2(ER^3)M^BR^1$. As shown in Reaction Scheme 5b, $M^BR^1{}_3$ can be reacted with compounds $M^A(ER^3)$, $HER^2$, and $HER^4$ to form a molecular precursor compound having the formula $M^A\text{-}(ER^2)(ER^3)(ER^4)M^BR^1$.

REACTION SCHEME 5b:

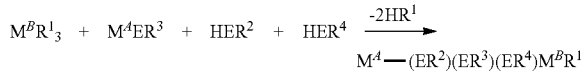

In further aspects, a compound $(NR^1{}_2)M^B(R^2)(ER^3)$ may be contacted with a chalcogen-containing compound $M^A(ER^4)$ in the presence of one equivalent of $HER^5$, where $M^A$, $M^B$, E, $R^1$, $R^2$, $R^3$, and $R^4$ are as defined above, $R^5$ is defined the same as $R^1$, $R^2$, $R^3$, and $R^4$, and $NR^1{}_2$ is amido. As shown in Reaction Scheme 5c, $(NR^1{}_2)M^BR^2{}_2$ may be reacted with $HER^3$ to form $(NR^1{}_2)M^B(R^2)(ER^3)$. The product $(NR^1{}_2)M^B(R^2)(ER^3)$ may be contacted with a compound $M^A(ER^4)$ in the presence of one equivalent of $HER^5$ to form a molecular precursor compound having the formula $M^4\text{-}(ER^3)(ER^4)(ER^5)M^B(NR^1{}_2)$.

REACTION SCHEME 5c:

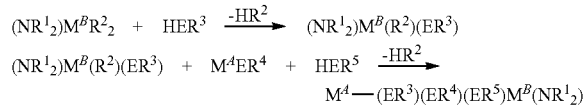

In Reaction Scheme 5c, the ligand $(NR^1{}_2)$ corresponds to the $R^1$ of Reaction Scheme 5a.

In additional variations, a compound $R^1{}_2M^BX_2$ can be contacted with a chalcogen-containing compound $M^4(ER^2)$ in the presence of one equivalent of $R^3ESi(CH_3)_3$ and one equivalent of $R^4ESi(CH_3)_3$, where $M^4$, $M^B$, E, $R^1$, $R^2$, $R^3$, and $R^4$ are as defined above. As shown in Reaction Scheme 5d, $R^1M^BX_2$ can be reacted with $M^4(ER^2)$, $R^3ESi(CH_3)_3$, and $R^4ESi(CH_3)_3$ to form a molecular precursor compound having the formula $M^4\text{-}(ER^2)(ER^3)(ER^4)M^BR^1$.

REACTION SCHEME 5d:

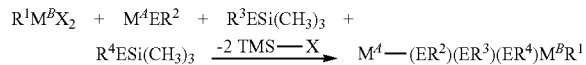

The reactions and manipulations of reagents can be carried out using known techniques under controlled inert atmosphere, such as dry nitrogen, and anaerobic conditions using a drybox and a Schlenk line system.

In certain examples, a molecular precursor of the MP1-Ag family can be synthesized by the following procedure. A Schlenk tube can be charged with $R^1{}_2M^B(ER^2)$ and an equimolar amount of $M^4(ER^2)$ in a glovebox in an inert, anaerobic atmosphere. To this mixture can be added dry solvent via cannula on a Schlenk line. The mixture can optionally be heated to dissolve or disperse the components. An equimolar amount of $HER^2$ can be added by use of a syringe and the Schlenk tube sealed under $N_2$. The mixture can be heated, optionally for about 12 hours at a temperature from about 30° C. to about 120° C. The solution can then be cooled, optionally for several hours at a temperature from about −80° C. to about 15° C. A solid or crystalline product can be isolated.

Among other things, in some embodiments, certain starting compounds were made in order to synthesize molecular precursor molecules of this disclosure. The starting compounds include certain compounds having one of the formulas $M^4ER$ and $R^1{}_2M^BER^2$, where $M^B$ is Ga or In, E is S or Se, and $R^1$ and $R^2$ are alkyl. Examples of the starting compounds that were prepared include $AgSe^tBu$, $^nBu_2In(Se^tBu)$, $^tBu_2Ga(Se^tBu)$, and $^iPr_2In(Se^tBu)$.

In one example, $^tBuSeH$ (5.8 mmol) and $Et_3N$ (1.1 mL) were slowly added to a solution of $AgNO_3$ (1.0 g, 5.8 mmol) in $CH_3CN$ (20 mL) at 0° C. A colorless solution with light yellow precipitate formed rapidly. The reaction mixture was allowed to warm to 25° C. and stirred for 12 h. The excess $^tBuSeH$ was removed under dynamic vacuum and a grey solid was recovered. The solid was washed with $CH_3CN$ (2×100 mL) to afford a grey solid, $AgSe^tBu$ (1.23 g, 87%).

Ligands

As used herein, the term ligand refers to any atom or chemical moiety that can donate electron density in bonding or coordination.

A ligand can be monodentate, bidentate or multidentate.

As used herein, the term ligand includes Lewis base ligands.

As used herein, the term organic ligand refers to an organic chemical group composed of atoms of carbon and hydrogen, having from 1 to 22 carbon atoms, and optionally containing oxygen, nitrogen, sulfur or other atoms, which can bind to another atom or molecule through a carbon atom. An organic ligand can be branched or unbranched, substituted or unsubstituted.

As used herein, the term inorganic ligand refers to an inorganic chemical group which can bind to another atom or molecule through a non-carbon atom.

Examples of ligands include halogens, water, alcohols, ethers, hydroxyls, amides, carboxylates, chalcogenylates, thiocarboxylates, selenocarboxylates, tellurocarboxylates, carbonates, nitrates, phosphates, sulfates, perchlorates, oxalates, and amines.

As used herein, the term chalcogenylate refers to thiocarboxylate, selenocarboxylate, and tellurocarboxylate, having the formula $RCE_2{}^-$, where E is S, Se, or Te.

As used herein, the term chalcocarbamate refers to thiocarbamate, selenocarbamate, and tellurocarbamate, having the formula $R^1R^2NCE_2{}^-$, where E is S, Se, or Te, and $R^1$ and $R^2$ are the same or different and are hydrogen, alkyl, aryl, or an organic ligand.

Examples of ligands include F, $Cl^-$, $H_2O$, ROH, $R_2O$, $OH^-$, $RO^-$, $NR_2{}^-$, $RCO_2{}^-$, $RCE_2{}^-$, $CO_3{}^{2-}$, $NO_3{}^-$, $PO_4{}^{3-}$, $SO_4{}^{2-}$, $ClO_4{}^-$, $C_2O_4{}^{2-}$, $NH_3$, $NR_3$, $R_2NH$, and $RNH_2$, where R is alkyl, and E is chalcogen.

Examples of ligands include azides, heteroaryls, thiocyanates, arylamines, arylalkylamines, nitrites, and sulfites.

Examples of ligands include $Br^-$, $N_3{}^-$, pyridine, [SCN—]$^-$, $ArNH_2$, $NO_2{}^-$, and $SO_3{}^{2-}$ where Ar is aryl.

Examples of ligands include cyanides or nitriles, isocyanides or isonitriles, alkylcyanides, alkylnitriles, alkylisocyanides, alkylisonitriles, arylcyanides, arylnitriles, arylisocyanides, and arylisonitriles.

Examples of ligands include hydrides, carbenes, carbon monoxide, isocyanates, isonitriles, thiolates, alkylthiolates, dialkylthiolates, thioethers, thiocarbamates, phosphines, alkylphosphines, arylphosphines, arylalkylphosphines, arsenines, alkylarsenines, arylarsenines, arylalkylarsenines, stilbines, alkylstilbines, arylstilbines, and arylalkylstilbines.

Examples of ligands include $I^-$, $H^-$, $R^-$, —$CN^-$, —CO, RNC, RSH, $R_2S$, $RS^-$, —$SCN^-$, $R_3P$, $R_3As$, $R_3Sb$, alkenes, and aryls, where each R is independently alkyl, aryl, or heteroaryl.

Examples of ligands include trioctylphosphine, trimethylvinylsilane and hexafluoroacetylacetonate.

Examples of ligands include nitric oxide, silyls, alkylgermyls, arylgermyls, arylalkylgermyls, alkylstannyls, arylstannyls, arylalkylstannyls, selenocyanates, selenolates, alkylselenolates, dialkylselenolates, selenoethers, selenocarbamates, tellurocyanates, tellurolates, alkyltellurolates, dialkyltellurolates, telluroethers, and tellurocarbamates.

Examples of ligands include chalcogenates, thiothiolates, selenothiolates, thioselenolates, selenoselenolates, alkyl thiothiolates, alkyl selenothiolates, alkyl thioselenolates, alkyl selenoselenolates, aryl thiothiolates, aryl selenothiolates, aryl thioselenolates, aryl selenoselenolates, arylalkyl thiothiolates, arylalkyl selenothiolates, arylalkyl thioselenolates, and arylalkyl selenoselenolates.

Examples of ligands include selenoethers and telluroethers.

Examples of ligands include NO, $O^{2-}$, $NH_nR_{3-n}$, $PH_nR_{3-n}$, $SiR_3^-$, $GeR_3^-$, $SnR_3^-$, —SR, $^-$SeR, $^-$TeR, $^-$SSR, $^-$SeSR, $^-$SSeR, $^-$SeSeR, and RCN, where n is from 1 to 3, and each R is independently alkyl or aryl.

As used herein, the term transition metals refers to atoms of Groups 3 though 12 of the Periodic Table of the elements recommended by the Commission on the Nomenclature of Inorganic Chemistry and published in *IUPAC Nomenclature of Inorganic Chemistry, Recommendations* 2005.

Photovoltaic Absorber Layer Compositions

A molecular precursor may be used to prepare a material for use in developing semiconductor products.

A molecular precursor may be used to prepare an absorber material for a solar cell product.

In some aspects, one or more molecular precursors may be used to prepare a CIS or CIGS material as a photovoltaic layer.

In some variations, one or more molecular precursors may be used to prepare a chemically and physically uniform semiconductor CIS or CIGS layer on a variety of substrates, including flexible substrates.

The CIS or CIGS layer may be used with various junction partners to produce a solar cell. Examples of junction partner layers are known in the art and include CdS, ZnS, ZnSe, and CdZnS. See, for example, Martin Green, *Solar Cells: Operating Principles, Technology and System Applications* (1986); Richard H. Bube, *Photovoltaic Materials* (1998); Antonio Luque and Steven Hegedus, *Handbook of Photovoltaic Science and Engineering* (2003).

In some aspects, the thickness of an absorber layer may be from about 0.001 to about 100 micrometers, or from about 0.001 to about 20 micrometers, or from about 0.01 to about 10 micrometers, or from about 0.05 to about 5 micrometers, or from about 0.1 to about 4 micrometers, or from about 0.1 to about 3.5 micrometers, or from about 0.1 to about 3 micrometers, or from about 0.1 to about 2.5 micrometers.

Substrates

The molecular precursors of this invention can be used to form a layer on a substrate. The substrate can be made of any substance, and can have any shape. Substrate layers of molecular precursors can be used to create a photovoltaic layer or device.

Examples of substrates on which a molecular precursor of this disclosure can be deposited or printed include semiconductors, doped semiconductors, silicon, gallium arsenide, insulators, glass, silicon dioxide, titanium dioxide, zinc oxide, silicon nitride, and combinations thereof.

A substrate may be coated with molybdenum or a molybdenum-containing compound.

In some embodiments, a substrate may be pre-treated with a molybdenum-containing compound, or one or more compounds containing molybdenum and selenium.

Examples of substrates on which a molecular precursor of this disclosure can be deposited or printed include metals, metal foils, molybdenum, aluminum, beryllium, cadmium, cerium, chromium, cobalt, copper, gallium, gold, lead, manganese, nickel, palladium, platinum, rhenium, rhodium, silver, stainless steel, steel, iron, strontium, tin, titanium, tungsten, zinc, zirconium, metal alloys, metal silicides, metal carbides, and combinations thereof.

Examples of substrates on which a molecular precursor of this disclosure can be deposited or printed include polymers, plastics, conductive polymers, copolymers, polymer blends, polyethylene terephthalates, polycarbonates, polyesters, polyester films, mylars, polyvinyl fluorides, polyvinylidene fluoride, polyethylenes, polyetherimides, polyethersulfones, polyetherketones, polyimides, polyvinylchlorides, acrylonitrile butadiene styrene polymers, silicones, epoxys, and combinations thereof.

Examples of substrates on which a molecular precursor of this disclosure can be deposited or printed include papers and coated papers.

A substrate of this disclosure can be of any shape. Examples of substrates on which a precursor of this disclosure can be deposited include a shaped substrate including a tube, a cylinder, a roller, a rod, a pin, a shaft, a plate, a blade, a vane, or a spheroid.

A substrate may be layered with an adhesion promoter before the deposition, coating or printing of a layer of a molecular precursor of this invention.

Examples of adhesion promoters include a glass layer, a metal layer, a titanium-containing layer, a tungsten-containing layer, a tantalum-containing layer, tungsten nitride, tantalum nitride, titanium nitride, titanium nitride silicide, tantalum nitride silicide, a chromium-containing layer, a vanadium-containing layer, a nitride layer, an oxide layer, a carbide layer, and combinations thereof.

Examples of adhesion promoters include organic adhesion promoters such as organofunctional silane coupling agents, silanes, hexamethyldisilazanes, glycol ether acetates, ethylene glycol bis-thioglycolates, acrylates, acrylics, mercaptans, thiols, selenols, tellurols, carboxylic acids, organic phosphoric acids, triazoles, and mixtures thereof.

Substrates may be layered with a barrier layer before the deposition of printing of a layer of a molecular precursor of this invention.

Examples of a barrier layer include a glass layer, a metal layer, a titanium-containing layer, a tungsten-containing layer, a tantalum-containing layer, tungsten nitride, tantalum nitride, titanium nitride, titanium nitride silicide, tantalum nitride silicide, and combinations thereof.

A substrate can be of any thickness, and can be from about 20 micrometers to about 20,000 micrometers or more in thickness.

Ink Compositions

Embodiments of this invention further provide ink compositions which contain one or more molecular precursor compounds. The molecular precursors of this invention may be used to make photovoltaic materials by printing an ink onto a substrate.

An ink of this disclosure advantageously allows precise control of the stoichiometric ratios of certain atoms in the ink because the ink can be composed of a mixture of molecular precursors.

Inks of this disclosure can be made by any methods known in the art.

In some embodiments, an ink can be made by mixing a molecular precursor with one or more carriers. The ink may be a suspension of the molecular precursors in an organic carrier. In some variations, the ink is a solution of the molecular precursors in an organic carrier. The carrier can be an organic liquid, or an organic solvent with an aqueous component.

An ink can be made by providing one or more molecular precursor compounds and solubilizing, dissolving, solvating, or dispersing the compounds with one or more carriers. The compounds dispersed in a carrier may be nanocrystalline, nanoparticles, microparticles, amorphous, or dissolved molecules.

The concentration of the molecular precursors in an ink of this disclosure can be from about 0.001% to about 99% (w/w), or from about 0.001% to about 90%, or from about 0.1% to about 90%.

A molecular precursor may exist in a liquid phase under the temperature and conditions used for deposition, coating or printing.

In some variations of this invention, molecular precursors that are partially soluble, or are insoluble in a particular carrier can be dispersed in the carrier by high shear mixing.

As used herein, the term dispersing encompasses the terms solubilizing, dissolving, and solvating.

The carrier for an ink of this disclosure may be an organic liquid or solvent. Examples of a carrier for an ink of this disclosure include one or more organic solvents, which may contain an aqueous component.

Embodiments of this invention further provide molecular precursor compounds having enhanced solubility in one or more carriers for preparing inks The solubility of a molecular precursor compound can be selected by variation of the nature and molecular size and weight of one or more organic ligands attached to the molecule.

Ink compositions of this disclosure can be made by methods known in the art, as well as methods disclosed herein.

Examples of a carrier for an ink of this disclosure include water, alcohol, methanol, ethanol, isopropyl alcohol, thiols, butanol, butanediol, glycerols, alkoxyalcohols, glycols, 1-methoxy-2-propanol, acetone, ethylene glycol, propylene glycol, propylene glycol laurate, ethylene glycol ethers, diethylene glycol, triethylene glycol monobutylether, propylene glycol monomethylether, 1,2-hexanediol, ethers, diethyl ether, aliphatic hydrocarbons, aromatic hydrocarbons, pentane, hexane, heptane, octane, isooctane, decane, cyclohexane, p-xylene, benzene, toluene, xylene, tetrahydofuran, siloxanes, cyclosiloxanes, silicone fluids, halogenated hydrocarbons, dibromomethane, dichloromethane, dichloroethane, trichloroethane chloroform, methylene chloride, acetonitrile, esters, acetates, ethyl acetate, butyl acetate, acrylates, isobornyl acrylate, 1,6-hexanediol diacrylate, polyethylene glycol diacrylate, ketones, acetone, methyl ethyl ketone, cyclohexanone, butyl carbitol, cyclopentanone, cyclohexanone, lactams, N-methyl pyrrolidone, N-(2-hydroxyethyl)-pyrrolidone, cyclic acetals, cyclic ketals, aldehydes, amides, dimethylformamide, methyl lactate, oils, natural oils, terpenes, and mixtures thereof.

An ink of this disclosure may further include components such as a surfactant, a dispersant, an emulsifier, an antifoaming agent, a dryer, a filler, a resin binder, a thickener, a viscosity modifier, an anti-oxidant, a flow agent, a plasticizer, a conductivity agent, a crystallization promoter, an extender, a film conditioner, an adhesion promoter, and a dye. Each of these components may be used in an ink of this disclosure at a level of from about 0.001% to about 10% or more of the ink composition.

Examples of surfactants include siloxanes, polyalkyleneoxide siloxanes, polyalkyleneoxide polydimethylsiloxanes, polyester polydimethylsiloxanes, ethoxylated nonylphenols, nonylphenoxy polyethyleneoxyethanol, fluorocarbon esters, fluoroaliphatic polymeric esters, fluorinated esters, alkylphenoxy alkyleneoxides, cetyl trimethyl ammonium chloride, carboxymethylamylose, ethoxylated acetylene glycols, betaines, N-n-dodecyl-N,N-dimethylbetaine, dialkyl sulfosuccinate salts, alkylnaphthalenesulfonate salts, fatty acid salts, polyoxyethylene alkylethers, polyoxyethylene alkylallylethers, polyoxyethylene-polyoxypropylene block copolymers, alkylamine salts, quaternary ammonium salts, and mixtures thereof.

Examples of surfactants include anionic, cationic, amphoteric, and nonionic surfactants. Examples of surfactants include SURFYNOL, DYNOL, ZONYL, FLUORAD, and SILWET surfactants.

A surfactant may be used in an ink of this disclosure at a level of from about 0.001% to about 2% of the ink composition.

Examples of a dispersant include a polymer dispersant, a surfactant, hydrophilic-hydrophobic block copolymers, acrylic block copolymers, acrylate block copolymers, graft polymers, and mixtures thereof.

Examples of an emulsifier include a fatty acid derivative, an ethylene stearamide, an oxidized polyethylene wax, mineral oils, a polyoxyethylene alkyl phenol ether, a polyoxyethylene glycol ether block copolymer, a polyoxyethylene sorbitan fatty acid ester, a sorbitan, an alkyl siloxane polyether polymer, polyoxyethylene monostearates, polyoxyethylene monolaurates, polyoxyethylene monooleates, and mixtures thereof.

Examples of an anti-foaming agent include polysiloxanes, dimethylpolysiloxanes, dimethyl siloxanes, silicones, polyethers, octyl alcohol, organic esters, ethyleneoxide propyleneoxide copolymers, and mixtures thereof.

Examples of a dryer include aromatic sulfonic acids, aromatic carboxylic acids, phthalic acid, hydroxyisophthalic acid, N-phthaloylglycine, 2-Pyrrolidone 5-carboxylic acid, and mixtures thereof.

Examples of a filler include metallic fillers, silver powder, silver flake, metal coated glass spheres, graphite powder, carbon black, conductive metal oxides, ethylene vinyl acetate polymers, and mixtures thereof.

Examples of a resin binder include acrylic resins, alkyd resins, vinyl resins, polyvinyl pyrrolidone, phenolic resins, ketone resins, aldehyde resins, polyvinyl butyral resin, amide resins, amino resins, acrylonitrile resins, cellulose resins, nitrocellulose resins, rubbers, fatty acids, epoxy resins, ethylene acrylic copolymers, fluoropolymers, gels, glycols, hydrocarbons, maleic resins, urea resins, natural rubbers, natural gums, phenolic resins, cresols, polyamides, polybutadienes, polyesters, polyolefins, polyurethanes, isocynates, polyols, thermoplastics, silicates, silicones, polystyrenes, and mixtures thereof.

Examples of thickeners and viscosity modifiers include conducting polymers, celluloses, urethanes, polyurethanes, styrene maleic anhydride copolymers, polyacrylates, polycarboxylic acids, carboxymethylcelluoses, hydroxyethylcelluloses, methylcelluloses, methyl hydroxyethyl celluloses, methyl hydroxypropyl celluloses, silicas, gellants, aluminates, titanates, gums, clays, waxes, polysaccharides, starches, and mixtures thereof.

Examples of anti-oxidants include phenolics, phosphites, phosphonites, thioesters, stearic acids, ascorbic acids, catechins, cholines, and mixtures thereof.

Examples of flow agents include waxes, celluloses, butyrates, surfactants, polyacrylates, and silicones.

Examples of a plasticizer include alkyl benzyl phthalates, butyl benzyl phthalates, dioctyl phthalates, diethyl phthalates, dimethyl phthalates, di-2-ethylhexy-adipates, diisobutyl phthalates, diisobutyl adipates, dicyclohexyl phthalates, glycerol tribenzoates, sucrose benzoates, polypropylene glycol dibenzoates, neopentyl glycol dibenzoates, dimethyl isophthalates, dibutyl phthalates, dibutyl sebacates, tri-n-hexyltrimellitates, and mixtures thereof.

Examples of a conductivity agent include lithium salts, lithium trifluoromethanesulfonates, lithium nitrates, dimethylamine hydrochlorides, diethylamine hydrochlorides, hydroxylamine hydrochlorides, and mixtures thereof.

Examples of a crystallization promoter include alkali metal salts, alkaline earth metal salts, sodium chalcogenates, cadmium salts, cadmium sulfates, cadmium sulfides, cadmium selenides, cadmium tellurides, indium sulfides, indium selenides, indium tellurides, gallium sulfides, gallium selenides, gallium tellurides, molybdenum, molybdenum sulfides, molybdenum selenides, molybdenum tellurides, molybdenum-containing compounds, and mixtures thereof.

An ink may contain one or more components selected from the group of a conducting polymer, copper metal, indium metal, gallium metal, zinc metal, alkali metals, alkali metal salts, alkaline earth metal salts, sodium chalcogenates, calcium chalcogenates, cadmium sulfide, cadmium selenide, cadmium telluride, indium sulfide, indium selenide, indium telluride, gallium sulfide, gallium selenide, gallium telluride, zinc sulfide, zinc selenide, zinc telluride, copper sulfide, copper selenide, copper telluride, molybdenum sulfide, molybdenum selenide, molybdenum telluride, and mixtures of any of the foregoing.

An ink of this disclosure may contain particles of a metal, a conductive metal, or an oxide. Examples of metal and oxide particles include silica, alumina, titania, copper, iron, steel, aluminum and mixtures thereof.

In certain variations, an ink may contain a biocide, a sequestering agent, a chelator, a humectant, a coalescent, or a viscosity modifier.

In certain aspects, an ink of this disclosure may be formed as a solution, a suspension, a slurry, or a semisolid gel or paste. An ink may include one or more molecular precursors solubilized in a carrier, or may be a solution of the molecular precursors. In certain variations, a molecular precursor may include particles or nanoparticles that can be suspended in a carrier, and may be a suspension or paint of the molecular precursors. In certain embodiments, a molecular precursor can be mixed with a minimal amount of a carrier, and may be a slurry or semisolid gel or paste of the molecular precursor.

The viscosity of an ink of this disclosure can be from about 0.5 centipoises (cP) to about 50 cP, or from about 0.6 to about 30 cP, or from about 1 to about 15 cP, or from about 2 to about 12 cP.

The viscosity of an ink of this disclosure can be from about 20 cP to about $2\times10^6$ cP, or greater. The viscosity of an ink of this disclosure can be from about 20 cP to about $1\times10^6$ cP, or from about 200 cP to about 200,000 cP, or from about 200 cP to about 100,000 cP, or from about 200 cP to about 40,000 cP, or from about 200 cP to about 20,000 cP.

The viscosity of an ink of this disclosure can be about 1 cP, or about 2 cP, or about 5 cP, or about 20 cP, or about 100 cP, or about 500 cP, or about 1,000 cP, or about 5,000 cP, or about 10,000 cP, or about 20,000 cP, or about 30,000 cP, or about 40,000 cP.

An ink may be composed of one or more molecular precursor compounds and one or more carriers. The ink may be a suspension or solution of the compounds in an organic carrier. An ink may further contain an additional indium-containing compound, such as $In(SeR)_3$, wherein R is alkyl or aryl. An ink may further contain an additional indium-containing compound, such as $In(SeR)_3$, and an additional gallium-containing compound, such as $Ga(SeR)_3$, wherein R is alkyl or aryl. For example, an ink may further contain $In(Se''Bu)_3$ and $Ga(Se''Bu)_3$. In some embodiments, an ink may contain one or more components from the group of a surfactant, a dispersant, an emulsifier, an anti-foaming agent, a dryer, a filler, a resin binder, a thickener, a viscosity modifier, an anti-oxidant, a flow agent, a plasticizer, a conductivity agent, a crystallization promoter, an extender, a film conditioner, an adhesion promoter, and a dye. In certain variations, an ink may contain one or more compounds from the group of cadmium sulfide, cadmium selenide, cadmium telluride, zinc sulfide, zinc selenide, zinc telluride, copper sulfide, copper selenide, and copper telluride. In some aspects, an ink may contain particles of a metal, a conductive metal, or an oxide.

An ink may be made by dispersing one or more molecular precursor compounds of this disclosure in one or more carriers to form a dispersion or solution.

A molecular precursor ink composition can be prepared by dispersing one or more molecular precursors in a solvent, and heating the solvent to dissolve or disperse the molecular precursors. The molecular precursors may have a concentration of from about 0.001% to about 99% (w/w), or from about 0.001% to about 90%, or from about 0.1% to about 90%, or from about 0.1% to about 50%, or from about 0.1% to about 40%, or from about 0.1% to about 30%, or from about 0.1% to about 20%, or from about 0.1% to about 10% in the solution or dispersion. To the solution or dispersion can also be added sources of a Group 13 compound or a chalcogen compound. For example, an ink may contain either one or both of $In(ER)_3$ and $Ga(ER)_3$, where each R is the same or different alkyl or aryl, in a total amount representing 0.1 atom-equivalents of indium plus gallium relative to the amount of copper in the molecular precursors. To this solution or dispersion can be added a binder, for example, polyvinyl pyrrolidone, and a thickener, for example, methylcelluose. Other components may be added as described above.

Processes for Films of Molecular Precursors on Substrates

The molecular precursors of this invention can be used to make photovoltaic materials by depositing a layer onto a substrate, where the layer contains one or more molecular precursors. The deposited layer may be a film or a thin film. Substrates are described above.

As used herein, the terms "deposit," "depositing," and "deposition" refer to any method for placing a compound or composition onto a surface or substrate, including spraying, coating, and printing.

As used herein, the term "thin film" refers to a layer of atoms or molecules, or a composition layer on a substrate having a thickness of less than about 300 micrometers.

A deposited layer of this disclosure advantageously allows precise control of the stoichiometric ratios of certain atoms in the layer because the layer can be composed of a mixture of molecular precursors.

The molecular precursors of this invention, and compositions containing molecular precursors, can be deposited onto a substrate using methods known in the art, as well as methods disclosed herein.

Examples of methods for depositing a molecular precursor onto a surface or substrate include all forms of spraying, coating, and printing.

Solar cell layers can be made by depositing one or more molecular precursors of this disclosure on a flexible substrate in a high throughput roll process. The depositing of molecular precursors in a high throughput roll process can be done by spraying or coating a composition containing one or more molecular precursors, or by printing an ink containing one or more molecular precursors of this disclosure.

Examples of methods for depositing a molecular precursor onto a surface or substrate include spraying, spray coating, spray deposition, spray pyrolysis, and combinations thereof.

Examples of methods for printing using an ink of this disclosure include screen printing, inkjet printing, aerosol jet printing, ink printing, jet printing, stamp/pad printing, transfer printing, pad printing, flexographic printing, gravure printing, contact printing, reverse printing, thermal printing, lithography, electrophotographic printing, and combinations thereof.

Examples of methods for depositing a molecular precursor onto a surface or substrate include electrodepositing, electroplating, electroless plating, bath deposition, coating, dip coating, wet coating, spin coating, knife coating, roller coating, rod coating, slot die coating, meyerbar coating, lip direct coating, capillary coating, liquid deposition, solution deposition, layer-by-layer deposition, spin casting, solution casting, chemical vapor deposition, aerosol chemical vapor deposition, metal-organic chemical vapor deposition, organometallic chemical vapor deposition, plasma enhanced chemical vapor deposition, and combinations thereof.

Examples of methods for depositing a molecular precursor onto a surface or substrate include atomic layer deposition, plasma-enhanced atomic layer deposition, vacuum chamber deposition, sputtering, RF sputtering, DC sputtering, magnetron sputtering, evaporation, electron beam evaporation, laser ablation, gas-source molecular beam epitaxy, vapor phase epitaxy, liquid phase epitaxy, and combinations thereof.

In certain embodiments, a first molecular precursor may be deposited onto a substrate, and subsequently a second molecular precursor may be deposited onto the substrate. In certain embodiments, several different molecular precursors may be deposited onto the substrate to create a layer.

In certain variations, different molecular precursors may be deposited onto a substrate simultaneously, or sequentially, whether by spraying, coating, printing, or by other methods. The different molecular precursors may be contacted or mixed before the depositing step, during the depositing step, or after the depositing step. The molecular precursors can be contacted before, during, or after the step of transporting the molecular precursors to the substrate surface.

The depositing of molecular precursors, including by spraying, coating, and printing, can be done in a controlled or inert atmosphere, such as in dry nitrogen and other inert gas atmospheres, as well as in a vacuum atmosphere.

Processes for depositing, spraying, coating, or printing molecular precursors can be done at various temperatures including from about $-20°$ C. to about $650°$ C., or from about $-20°$ C. to about $600°$ C., or from about $-20°$ C. to about $400°$ C., or from about $20°$ C. to about $360°$ C., or from about $20°$ C. to about $300°$ C., or from about $20°$ C. to about $250°$ C.

Processes for making a solar cell involving a step of transforming a molecular precursor compound into a material or semiconductor can be performed at various temperatures including from about $100°$ C. to about $650°$ C., or from about $150°$ C. to about $650°$ C., or from about $250°$ C. to about $650°$ C., or from about $300°$ C. to about $650°$ C., or from about $400°$ C. to about $650°$ C.

In certain aspects, depositing of molecular precursors on a substrate can be done while the substrate is heated. In these variations, a thin-film material may be deposited or formed on the substrate.

In some embodiments, a step of converting a precursor to a material and a step of annealing can be done simultaneously. In general, a step of heating a precursor can be done before, during or after any step of depositing the precursor.

In some variations, a substrate can be cooled after a step of heating. In certain embodiments, a substrate can be cooled before, during, or after a step of depositing a precursor. A substrate may be cooled to return the substrate to a lower temperature, or to room temperature, or to an operating temperature of a deposition unit. Various coolants or cooling methods can be applied to cool a substrate.

The depositing of molecular precursors on a substrate may be done with various apparatuses and devices known in art, as well as devices described herein.

In some variations, the depositing of molecular precursors can be performed using a spray nozzle with adjustable nozzle dimensions to provide a uniform spray composition and distribution.

Embodiments of this disclosure further contemplate articles made by depositing a layer onto a substrate, where the layer contains one or more molecular precursors. The article may be a substrate having a layer of a film, or a thin film, which is deposited, sprayed, coated, or printed onto the substrate. In certain variations, an article may have a substrate printed with a molecular precursor ink, where the ink is printed in a pattern on the substrate.

Photovoltaic Devices

The molecular precursors of this invention can be used to make photovoltaic materials and solar cells of high efficiency.

Figure 6:
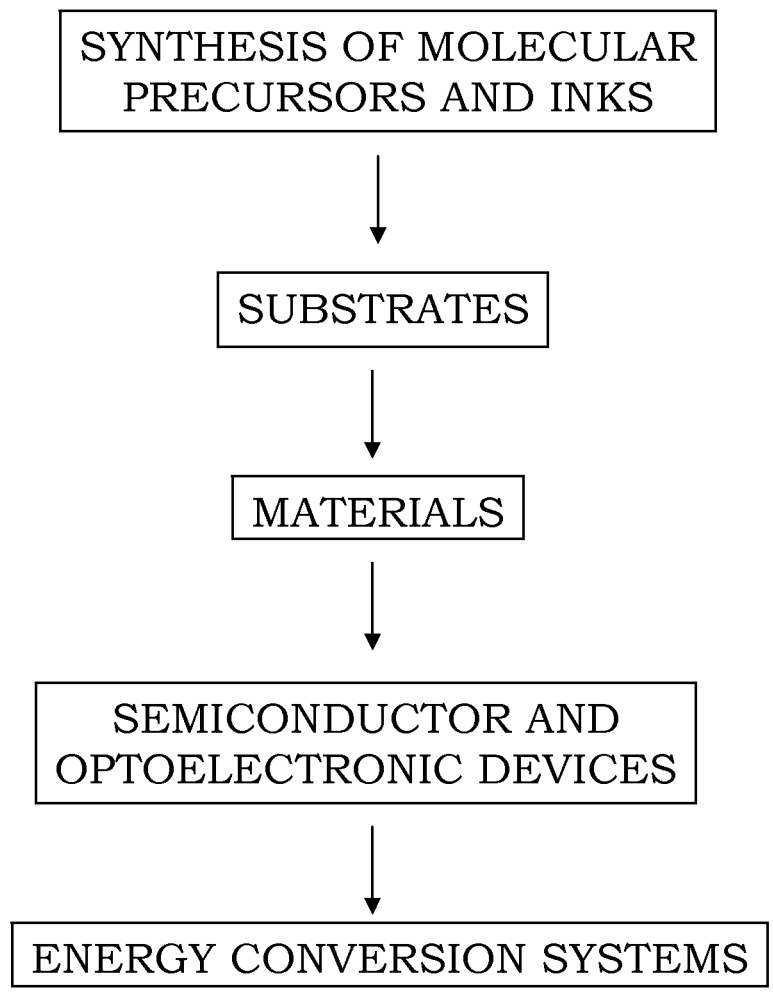
FIG. 6: Schematic representation of embodiments of this invention in which molecular precursors and ink compositions are deposited onto particular substrates by methods including spraying, coating, and printing, and are used to make semiconductor and optoelectronic materials and devices, as well as energy conversion systems.

As shown in FIG. 6, embodiments of this invention may further provide optoelectronic devices and energy conversion systems. Following the synthesis of molecular precursor compounds, the compounds can be sprayed, deposited, or printed onto substrates and formed into absorber materials and semiconductor layers. Absorber materials can be the basis for optoelectronic devices and energy conversion systems.

In some embodiments, the solar cell is a thin layer solar cell having a CIS or CIGS absorber layer deposited or printed on a substrate. Some methods for solar cells are disclosed in U.S. Pat. Nos. 5,441,897, 5,976,614, 6,518,086, 5,436,204, 7,179,677, and PCT International Application Publication Nos. WO2008057119 and WO2008063190.

In some embodiments, a solar cell of this disclosure is a heterojunction device made with a CIS or CIGS cell. The CIS or CIGS layer may be used as a junction partner with a layer of, for example, cadmium sulfide, cadmium selenide, cadmium telluride, zinc sulfide, zinc selenide, or zinc telluride. The absorber layer may be adjacent to a layer of MgS, MgSe, MgTe, HgS, HgSe, HgTe, AlN, AlP, AlAs, AlSb, GaN, GaP, GaAs, GaSb, InN, InP, InAs, InSb, or combinations thereof.

In certain variations, a solar cell of this disclosure is a multijunction device made with one or more stacked solar cells.

Figure 7:
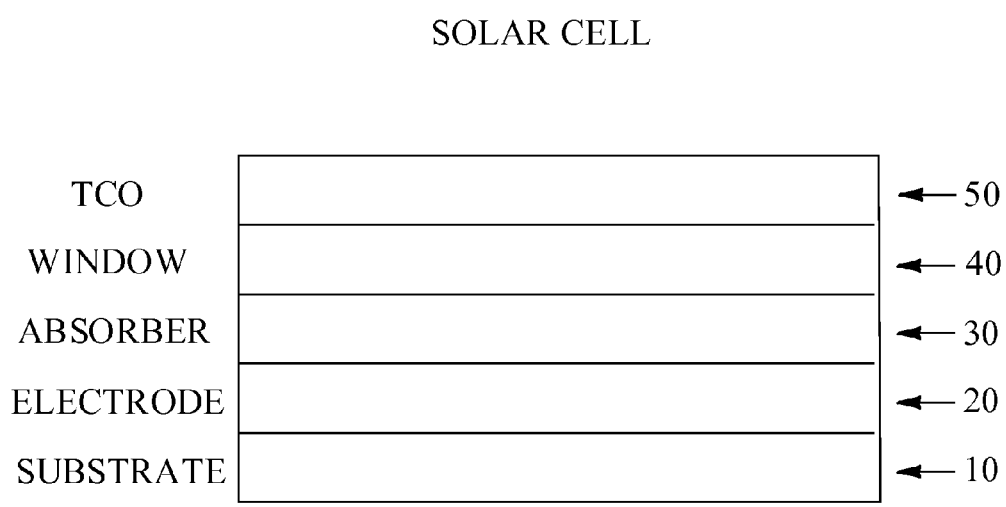
FIG. 7: Schematic representation of a solar cell embodiment of this invention.

As shown in FIG. 7, a solar cell device of this disclosure may have a substrate 10, an electrode layer 20, an absorber layer 30, a window layer 40, and a transparent conductive layer (TCO) 50. The substrate 10 may be metal, plastic, glass, or ceramic. The electrode layer 20 can be a molybdenum-containing layer. The absorber layer 30 may be a CIS or CIGS layer. The window layer 40 may be a cadmium sulfide layer. The transparent conductive layer 50 can be an indium tin oxide layer or a doped zinc oxide layer.

A solar cell device of this disclosure may have a substrate, an electrode layer, an absorber layer, a window layer, an adhesion promoting layer, a junction partner layer, a transparent layer, a transparent electrode layer, a transparent conductive oxide layer, a transparent conductive polymer layer, a doped conductive polymer layer, an encapsulating layer, an anti-reflective layer, a protective layer, or a protective polymer layer. In certain variations, an absorber layer includes a plurality of absorber layers.

In certain variations, solar cells may be made by processes using molecular precursor compounds and compositions of this invention that advantageously avoid additional sulfurization or selenization steps.

In certain variations, a solar cell device may have a molybdenum-containing layer, or an interfacial molybdenum-containing layer.

Examples of a protective polymer include silicon rubbers, butyryl plastics, ethylene vinyl acetates, and combinations thereof.

Substrates can be made of a flexible material which can be handled in a roll. The electrode layer may be a thin foil.

Absorber layers of this disclosure can be made by depositing or printing a composition containing nanoparticles onto a substrate, where the nanoparticles can be made with molecular precursor compounds of this invention. In some processes, nanoparticles can be made with molecular precursor compounds and deposited on a substrate. Deposited nanoparticles can subsequently be transformed by the application of heat or energy.

Sources of Metals

Sources of copper include copper metal, Cu(I), Cu(II), copper halides, copper chlorides, copper acetates, copper alkoxides, copper alkyls, copper diketonates, copper 2,2,6,6,-tetramethyl-3,5,-heptanedionate, copper 2,4-pentanedionate, copper hexafluoroacetylacetonate, copper acetylacetonate, copper dimethylaminoethoxide, copper ketoesters, and mixtures thereof.

Sources of indium include indium metal, trialkylindium, trisdialkylamineindium, indium halides, indium chlorides, dimethylindium chlorides, trimethylindium, indium acetylacetonates, indium hexafluoropentanedionates, indium methoxyethoxides, indium methyltrimethylacetylacetates, indium trifluoropentanedionates, and mixtures thereof.

Sources of gallium include gallium metal, trialkylgallium, trisdialkylamine gallium, gallium halides, gallium fluorides, gallium chlorides, gallium iodides, diethylgallium chlorides, gallium acetate, gallium 2,4-pentanedionate, gallium ethoxide, gallium 2,2,6,6,-tetramethylheptanedionate, trisdimethylaminogallium, and mixtures thereof.

Some sources of gallium and indium are described in International Patent Publication No. WO2008057119.

In various processes of this disclosure, a composition or material may optionally be subjected to a step of sulfurization or selenization.

Sulfurization with $H_2S$ or selenization with $H_2Se$ may be carried out by using pure $H_2S$ or $H_2Se$, respectively, or may be done by dilution in hydrogen or in nitrogen. Selenization can also be carried out with Se vapor, or other source of elemental selenium.

A sulfurization or selenization step can be done at any temperature from about 200° C. to about 600° C., or at temperatures below 200° C. One or more steps of sulfurization and selenization may be performed concurrently, or sequentially.

Examples of sulfurizing agents include hydrogen sulfide, hydrogen sulfide diluted with hydrogen, elemental sulfur, sulfur powder, carbon disulfide, alkyl polysulfides, dimethyl sulfide, dimethyl disulfide, and mixtures thereof.

A sulfurization or selenization step can also be done with co-deposition of another metal such as copper, indium, or gallium.

Chemical Definitions

As used herein, the term (A,B) when referring to compounds or atoms indicates that either A or B, or a combination thereof may be found in the formula. For example, (S,Se) indicates that atoms of either sulfur or selenium, or a combination thereof may be found.

The atoms S, Se, and Te of Group 16 are referred to as chalcogens.

As used herein, the term "chalcogenide" refers to a compound containing one or more chalcogen atoms bonded to one or more metal atoms.

The term "alkyl" as used herein refers to a hydrocarbyl radical of a saturated aliphatic group, which can be a branched or unbranched, substituted or unsubstituted aliphatic group containing from 1 to 22 carbon atoms. This definition applies to the alkyl portion of other groups such as, for example, cycloalkyl, alkoxy, alkanoyl, aralkyl, and other groups defined below. The term "cycloalkyl" as used herein refers to a saturated, substituted or unsubstituted cyclic alkyl ring containing from 3 to 12 carbon atoms. As used herein, the term "C(1-5)alkyl" includes C(1)alkyl, C(2)alkyl, C(3)alkyl, C(4)alkyl, and C(5)alkyl. Likewise, the term "C(3-22)alkyl" includes C(1)alkyl, C(2)alkyl, C(3)alkyl, C(4)alkyl, C(5)alkyl, C(6)alkyl, C(7)alkyl, C(8)alkyl, C(9)alkyl, C(10)alkyl, C(11)alkyl, C(12)alkyl, C(13)alkyl, C(14)alkyl, C(15)alkyl, C(16)alkyl, C(17)alkyl, C(18)alkyl, C(19)alkyl, C(20)alkyl, C(21)alkyl, and C(22)alkyl.

The term "alkenyl" as used herein refers to an unsaturated, branched or unbranched, substituted or unsubstituted alkyl or cycloalkyl having 2 to 22 carbon atoms and at least one carbon-carbon double bond. The term "alkynyl" as used herein refers to an unsaturated, branched or unbranched, substituted or unsubstituted alkyl or cycloalkyl having 2 to 22 carbon atoms and at least one carbon-carbon triple bond.

The term "alkoxy" as used herein refers to an alkyl, cycloalkyl, alkenyl, or alkynyl group covalently bonded to an oxygen atom. The term "alkanoyl" as used herein refers to —C(=O)-alkyl, which may alternatively be referred to as "acyl." The term "alkanoyloxy" as used herein refers to —O—C(=O)-alkyl groups. The term "alkylamino" as used herein refers to the group —NRR', where R and R' are each either hydrogen or alkyl, and at least one of R and R' is alkyl. Alkylamino includes groups such as piperidino wherein R and R' form a ring. The term "alkylaminoalkyl" refers to -alkyl-NRR'.

The term "aryl" as used herein refers to any stable monocyclic, bicyclic, or polycyclic carbon ring system of from 4 to 12 atoms in each ring, wherein at least one ring is aromatic. Some examples of an aryl include phenyl, naphthyl, tetrahydro-naphthyl, indanyl, and biphenyl. Where an aryl substituent is bicyclic and one ring is non-aromatic, it is understood that attachment is to the aromatic ring. An aryl may be substituted or unsubstituted.

The term "heteroaryl" as used herein refers to any stable monocyclic, bicyclic, or polycyclic carbon ring system of from 4 to 12 atoms in each ring, wherein at least one ring is aromatic and contains from 1 to 4 heteroatoms selected from oxygen, nitrogen and sulfur. Phosphorous and selenium may be a heteroatom. Some examples of a heteroaryl include acridinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, pyrazinyl, pyridazinyl, pyridinyl, pyrimidinyl, pyrrolyl, and tetrahydroquinolinyl. A heteroaryl includes the N-oxide derivative of a nitrogen-containing heteroaryl.

The term "heterocycle" or "heterocyclyl" as used herein refers to an aromatic or nonaromatic ring system of from five to twenty-two atoms, wherein from 1 to 4 of the ring atoms are heteroatoms selected from oxygen, nitrogen, and sulfur. Phosphorous and selenium may be a heteroatom. Thus, a heterocycle may be a heteroaryl or a dihydro or tetrahydro version thereof.

The term "aroyl" as used herein refers to an aryl radical derived from an aromatic carboxylic acid, such as a substituted benzoic acid. The term "aralkyl" as used herein refers to an aryl group bonded to an alkyl group, for example, a benzyl group.

The term "carboxyl" as used herein represents a group of the formula $-C(=O)OH$ or $-C(=O)O^-$. The terms "carbonyl" and "acyl" as used herein refer to a group in which an oxygen atom is double-bonded to a carbon atom $>C=O$. The term "hydroxyl" as used herein refers to $-OH$ or $-O^-$. The term "nitrile" or "cyano" as used herein refers to $-CN$. The term "halogen" or "halo" refers to fluoro (—F), chloro (—Cl), bromo (—Br), and iodo (—I).

The term "substituted" as used herein refers to an atom having one or more substitutions or substituents which can be the same or different and may include a hydrogen substituent. Thus, the terms alkyl, cycloalkyl, alkenyl, alkynyl, alkoxy, alkanoyl, alkanoyloxy, alkylamino, alkylaminoalkyl, aryl, heteroaryl, heterocycle, aroyl, and aralkyl as used herein refer to groups which include substituted variations. Substituted variations include linear, branched, and cyclic variations, and groups having a substituent or substituents replacing one or more hydrogens attached to any carbon atom of the group. Substituents that may be attached to a carbon atom of the group include alkyl, cycloalkyl, alkenyl, alkynyl, alkoxy, alkanoyl, alkanoyloxy, alkylamino, alkylaminoalkyl, aryl, heteroaryl, heterocycle, aroyl, aralkyl, acyl, hydroxyl, cyano, halo, haloalkyl, amino, aminoacyl, alkylaminoacyl, acyloxy, aryloxy, aryloxyalkyl, mercapto, nitro, carbamyl, carbamoyl, and heterocycle. For example, the term ethyl includes without limitation $-CH_2CH_3$, $-CHFCH_3$, $-CF_2CH_3$, $-CHFCH_2F$, $-CHFCHF_2$, $-CHFCF_3$, $-CF_2CH_2F$, $-CF_2CHF_2$, $-CF_2CF_3$, and other variations as described above. In general, a substituent may itself be further substituted with any atom or group of atoms.

Some examples of a substituent for a substituted alkyl include halogen, hydroxyl, carbonyl, carboxyl, ester, aldehyde, carboxylate, formyl, ketone, thiocarbonyl, thioester, thioacetate, thioformate, selenocarbonyl, selenoester, selenoacetate, selenoformate, alkoxyl, phosphoryl, phosphonate, phosphinate, amino, amido, amidine, imino, cyano, nitro, azido, carbamato, sulfhydryl, alkylthio, sulfate, sulfonate, sulfamoyl, sulfonamido, sulfonyl, silyl, heterocyclyl, aryl, aralkyl, aromatic, and heteroaryl.

It will be understood that "substitution" or "substituted with" refers to such substitution that is in accordance with permitted valence of the substituted atom and the substituent. As used herein, the term "substituted" includes all permissible substituents.

In general, a compound may contain one or more chiral centers. Compounds containing one or more chiral centers may include those described as an "isomer," a "stereoisomer," a "diastereomer," an "enantiomer," an "optical isomer," or as a "racemic mixture." Conventions for stereochemical nomenclature, for example the stereoisomer naming rules of Cahn, Ingold and Prelog, as well as methods for the determination of stereochemistry and the separation of stereoisomers are known in the art. See, for example, Michael B. Smith and Jerry March, *March's Advanced Organic Chemistry*, 5th edition, 2001. The compounds and structures of this disclosure are meant to encompass all possible isomers, stereoisomers, diastereomers, enantiomers, and/or optical isomers that would be understood to exist for the specified compound or structure, including any mixture, racemic or otherwise, thereof.

This invention encompasses any and all tautomeric, solvated or unsolvated, hydrated or unhydrated forms, as well as any atom isotope forms of the compounds and compositions disclosed herein.

This invention encompasses any and all crystalline polymorphs or different crystalline forms of the compounds and compositions disclosed herein.

Additional Embodiments

All publications, references, patents, patent publications and patent applications cited herein are each hereby specifically incorporated by reference in their entirety for all purposes.

While this invention has been described in relation to certain embodiments, aspects, or variations, and many details have been set forth for purposes of illustration, it will be apparent to those skilled in the art that this invention includes additional embodiments, aspects, or variations, and that some of the details described herein may be varied considerably without departing from this invention. This invention includes such additional embodiments, aspects, and variations, and any modifications and equivalents thereof. In particular, this invention includes any combination of the features, terms, or elements of the various illustrative components and examples.

The use herein of the terms "a," "an," "the" and similar terms in describing the invention, and in the claims, are to be construed to include both the singular and the plural.

The terms "comprising," "having," "include," "including" and "containing" are to be construed as open-ended terms which mean, for example, "including, but not limited to." Thus, terms such as "comprising," "having," "include," "including" and "containing" are to be construed as being inclusive, not exclusive.

Recitation of a range of values herein refers individually to each and any separate value falling within the range as if it were individually recited herein, whether or not some of the values within the range are expressly recited. For example, the range "4 to 12" includes without limitation any whole, integer, fractional, or rational value greater than or equal to 4 and less than or equal to 12, as would be understood by those skilled in the art. Specific values employed herein will be understood as exemplary and not to limit the scope of the invention.

Recitation of a range of a number of atoms herein refers individually to each and any separate value falling within the range as if it were individually recited herein, whether or not some of the values within the range are expressly recited. For example, the term "C1-8" includes without limitation the species C1, C2, C3, C4, C5, C6, C7, and C8.

Definitions of technical terms provided herein should be construed to include without recitation those meanings associated with these terms known to those skilled in the art, and are not intended to limit the scope of the invention. Definitions of technical terms provided herein shall be construed to dominate over alternative definitions in the art or definitions which become incorporated herein by reference to the extent that the alternative definitions conflict with the definition provided herein.

The examples given herein, and the exemplary language used herein are solely for the purpose of illustration, and are not intended to limit the scope of the invention. All examples and lists of examples are understood to be non-limiting.

When a list of examples is given, such as a list of compounds, molecules or compositions suitable for this invention, it will be apparent to those skilled in the art that mixtures of the listed compounds, molecules or compositions may also be suitable.

EXAMPLES

Thermogravimetric analysis (TGA) was performed using a Q50 Thermogravimetric Analyzer (TA Instruments, New Castle, Del.). NMR data were recorded using a Varian 400 MHz spectrometer.

Example 1

Molecular Precursor Compounds

An MP1 molecular precursor represented by the formula Cu—(S$^t$Bu)$_3$In$^i$Pr was synthesized using the following procedure. A 100 mL Schlenk tube was charged with $^i$Pr$_2$In(S$^t$Bu) (1.68 g, 6.1 mmol) and Cu(S$^t$Bu) (0.93 g, 6.1 mmol) in an inert atmosphere glovebox. To this mixture was added 20 mL of dry toluene via cannula transfer using a Schlenk line. The mixture was heated until it became homogeneous. One equivalent of HS$^t$Bu (0.7 mL, 6.1 mmol) was added via syringe and the Schlenk tube was kept under static N$_2$. The mixture was heated for about 12-14 h at 60° C. with stirring. The solution was then filtered warm and crystals began to form at room temperature. The solution was cooled at −60° C. for 16 hours. Yellow crystalline solid was isolated, 1.4 g, yield 47%. Elemental analysis: C, 36.2, H, 6.7, Cu, 13.0, In, 23.9, S, 18.0. NMR: (1H) 1.66 (br s 34H); (13C) 23.15 (s); 26.64 (s); 37.68 (s); 47.44 (s). Solubility: pentane, nil; diethyl ether, ss, benzene, s heat; toluene, vs heat; THF, s; CHCl$_3$, s.

The TGA for this MP1 molecular precursor showed a single transition having a midpoint at 220° C., ending at 227° C. The yield for the transition was 50.4% (w/w), as compared to a theoretical yield for the formula CuInS$_2$ of 49.5% (w/w). Thus, the TGA showed that this MP1 molecular precursor can be used to prepare CuInS$_2$ layers and materials, and can be used as a component to prepare other semiconductor layers, crystals, and materials.

The structure of this crystalline MP1 precursor molecule was determined by single crystal X-ray diffraction. The molecular structure of the compound was of a dimer, represented by the formula (Cu—(S$^t$Bu)$_3$In$^i$Pr)$_2$.

The local structure surrounding the indium atom was a tetrahedral arrangement of four atoms. At one apex of the indium tetrahedron was the methine carbon atom of the $^i$Pr group. The remainder of the tetrahedron was formed by the sulfur atoms of three (S$^t$Bu) ligands, each attached through a sulfur atom to indium.

The local structure surrounding the copper atom was bonding of the copper atom to three sulfur atoms of three S$^t$Bu ligands. The three S$^t$Bu ligands were bridging ligands that were each shared through bonding of their sulfur atom to a copper atom and an indium atom.

Example 2

An MP1 molecular precursor represented by the formula Cu—(S$^t$Bu)$_3$In$^n$Bu was synthesized using the following procedure. A 100 mL Schlenk tube was charged with $^n$Bu$_2$In(S$^t$Bu) (1.8 g, 5.8 mmol) and Cu(S$^t$Bu) (0.89 g, 5.8 mmol) in an inert atmosphere glovebox. To this mixture was added 20 mL of dry toluene via cannula transfer using a Schlenk line. The mixture was heated until it became homogeneous. One equivalent of HS$^t$Bu (0.65 mL, 5.8 mmol) was added via syringe and the Schlenk tube was kept under static N$_2$. The mixture was heated for about 12-14 hours at 100° C. with stirring. The solution was then allowed to cool to room temperature and filtered. The solvent was removed under vacuum, and the product was extracted with pentane. The pentane extract was concentrated and cooled for about 12-14 hours at −60° C. to yield pale yellow crystals. Yield, 1.4 g, 48%. NMR: (1H) 1.006 (m, 3H); 1.44 (m, 2H) 1.56 (m, 2H), 1.68 (br s, 27H); 1.998 (m, 2H); (13C) 13.86 (s); 23.13 (s); 28.54 (s); 30.51 (s); 37.23 (s); 47.47(s). Solubility: pentane, s; diethyl ether, vs, benzene, vs; toluene, vs; THF, vs; CHCl$_3$, vs.

Figure 8:
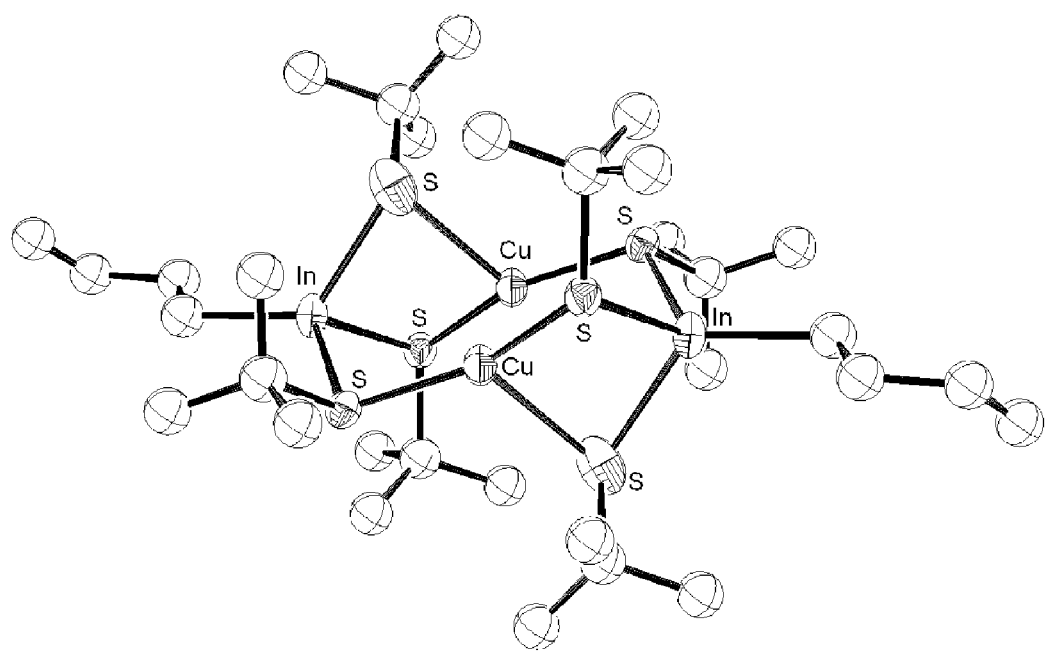
FIG. 8.

In FIG. 8 is shown the structure of this crystalline MP1 precursor molecule as determined by single crystal X-ray diffraction. The molecular structure of the compound was of a dimer, represented by the formula (Cu—(S$^t$Bu)$_3$In$^n$Bu)$_2$.

As shown in FIG. 8, the local structure of this molecular precursor compound regarding the indium atom in the crystalline compound was a tetrahedral arrangement of four atoms. At one apex of the indium tetrahedron was the terminal methylene carbon atom of the $^n$Bu group. The remainder of the tetrahedron was formed by the sulfur atoms of three (S$^t$Bu) ligands, each attached through a sulfur atom to indium.

As shown in FIG. 8, the local structure surrounding the copper atom was bonding of the copper atom to three sulfur atoms of three S$^t$Bu ligands. The three S$^t$Bu ligands were bridging ligands that were each shared through bonding of their sulfur atom to a copper atom and an indium atom.

The TGA for this MP1 molecular precursor compound showed a single transition having a midpoint at 235° C., ending at 248° C. The yield for the transition was 50.4% (w/w), as compared to a theoretical yield for the formula CuInS$_2$ of 48.1% (w/w). Thus, the TGA showed that this MP1 molecular precursor can be used to prepare CuInS$_2$ layers and materials, and can be used as a component to prepare other semiconductor layers, crystals, and materials.

Example 3

An MP1 molecular precursor represented by the formula Cu—(Se$^t$Bu)$_3$In$^n$Bu was synthesized using the following procedure. $^t$BuSeH (8.8 mmol) was slowly added to a pentane solution (30 mL) of $^n$Bu$_3$In (1.67 g, 5.8 mmol). The mixture was stirred at 25° C. for 12 h, and the solvent and excess $^t$BuSeH were removed under dynamic vacuum. A colorless oil of $^n$Bu$_2$In(Se$^t$Bu) was obtained and was then combined with CuSe$^t$Bu (1.17 g, 5.8 mmol) with 40 mL of toluene. $^t$BuSeH (2.10 g, 5.8 mmol) was slowly added to the reaction mixture, and the reaction mixture was stirred at 60° C. for about 12-14 hours. A deep red solution was formed. The solvent was removed under dynamic vacuum and the remaining solid was extracted with pentane (60 mL) and filtered. Concentration of the filtrate to 20 mL and storage at −60° C. in a freezer afforded 2.02 g (54%) of yellow crystals. NMR: (1H) 1.00 (t, 3H, $^3J_{HH}$=7.6), 1.54 (m, 2H), 1.80 (s, 29H), 2.01 (m, 2H) in C6D6; (13C) 13.9, 21.6, 28.4, 30.7, 37.9 in C6D6; (77Se) 154.0 in C6D6. Solubility: pentane, s; diethyl ether, vs, benzene, vs; toluene, vs; THF, vs; CHCl$_3$, vs.

The TGA for this MP1 molecular precursor showed a single transition having a midpoint at 174° C., ending at 196° C. The yield for the transition was 48.5% (w/w), as compared to a theoretical yield for the formula CuInSe$_2$ of 52.3% (w/w). Thus, the TGA data showed that this MP1 molecular precursor can be used to prepare CuInSe$_2$ layers and materials, and can be used as a component to prepare other semiconductor layers, crystals, and materials.

Example 4

An MP1 molecular precursor represented by the formula Cu—(S$^t$Bu)$_3$In$^t$Bu was synthesized using the following procedure. A 100 mL Schlenk tube was charged with $^t$Bu$_2$In(S$^t$Bu) (1.5 g, 5.2 mmol) and Cu(S$^t$Bu) (0.80 g, 5.2 mmol) in an inert atmosphere glovebox. To this mixture was added 30 mL of dry benzene via cannula transfer using a Schlenk line. The mixture was heated until it became homogeneous, then filtered and allowed to cool to room temperature. One equivalent of HS$^t$Bu (0.6 mL, 5.2 mmol) was added via syringe and the Schlenk tube was kept under static N$_2$. The mixture was stirred for about 12-14 hours, and a pale yellow precipitate was formed. The solution was filtered and the remaining solid was washed with benzene at room temperature. The solid product was dried under vacuum. Yield 2.15 g (83%). The physical state of the molecular precursor Cu—(S$^t$Bu)$_3$In$^t$Bu was a pale yellow solid at room temperature. Elemental analysis: C, 38.3, H, 7.2, Cu, 13.1; In, 21.8; S, 18.5. NMR: C6D6: 1.627 (s, 9H); 1.69 (s, 27H); CDCl3: 1.45 (s, 9H); 1.56 (s, 27H). Solubility: pentane, nil; diethyl ether, nil, benzene, ss heat; toluene, s heat; THF, ss; CHCl$_3$, s.

Figure 9:
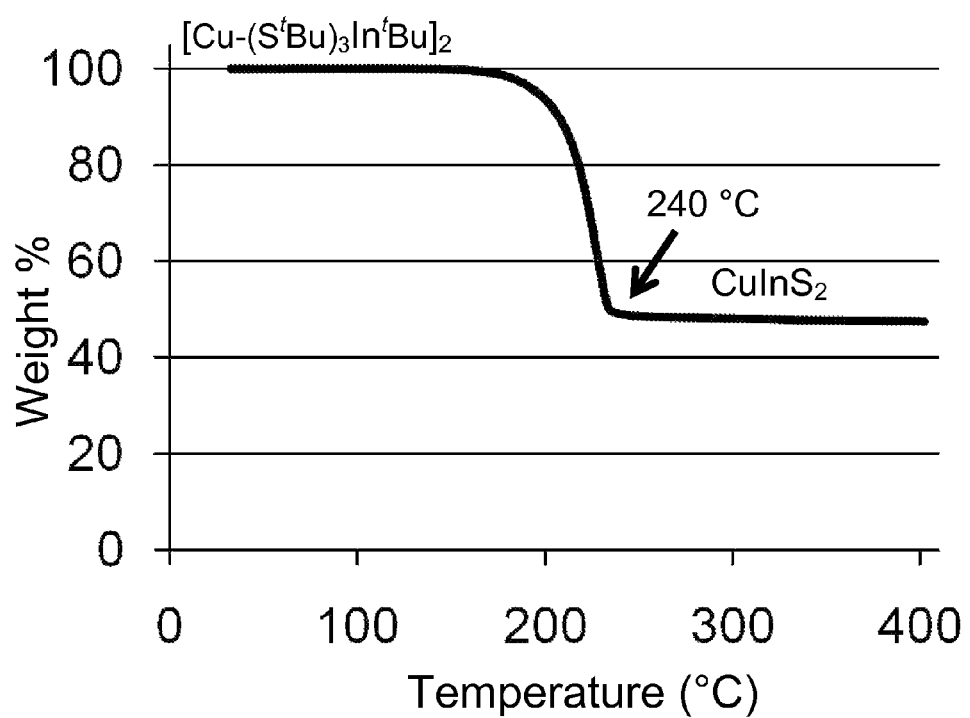
FIG. 9.

In FIG. 9 is shown the TGA for this MP1 molecular precursor. The TGA showed a single sharp transition ending at about 240° C. The yield for the transition was 48.1% (w/w), as compared to a theoretical yield for the formula CuInS$_2$ of 48.1% (w/w). Thus, the TGA showed that this MP1 molecular precursor can be used to prepare CuInS$_2$ layers and materials, and can be used as a component to prepare other semiconductor layers, crystals, and materials.

The structure of this crystalline MP1 precursor molecule was determined by single crystal X-ray diffraction. The molecular structure of the compound was of a dimer, represented by the formula (Cu—(S$^t$Bu)$_3$In$^t$Bu)$_2$.

Example 5

An MP1 molecular precursor represented by the formula Cu—(Se$^t$Bu)$_3$Ga$^t$Bu was synthesized using the following procedure. $^t$BuSeH (8.7 mmol) was slowly added to a pentane solution (30 mL) of $^t$Bu$_3$Ga (2.1 g, 8.7 mmol). The mixture was stirred at 25° C. for 30 min., and the solvent was removed under dynamic vacuum. Solid $^t$Bu$_2$Ga(Se$^t$Bu) (0.68 g, 2.1 mmol) was combined with CuSe$^t$Bu (0.42 g, 2.1 mmol) with 40 mL of toluene. $^t$BuSeH (0.76 g, 2.1 mmol) was slowly added to the reaction mixture, and the reaction mixture was stirred at 90° C. for about 24 h. A deep red solution was formed with a light brown solid precipitate. The light brown solid was collected and washed with toluene at 25° C., then dried under vacuum to yield 0.65 g. (Yield, 52%) NMR: (1H) 1.62 (s, 9H), 1.80 (s, 27H) in C6D6. Solubility: pentane, nil; diethyl ether, nil, benzene, ss heat; toluene, s heat.

Figure 10:
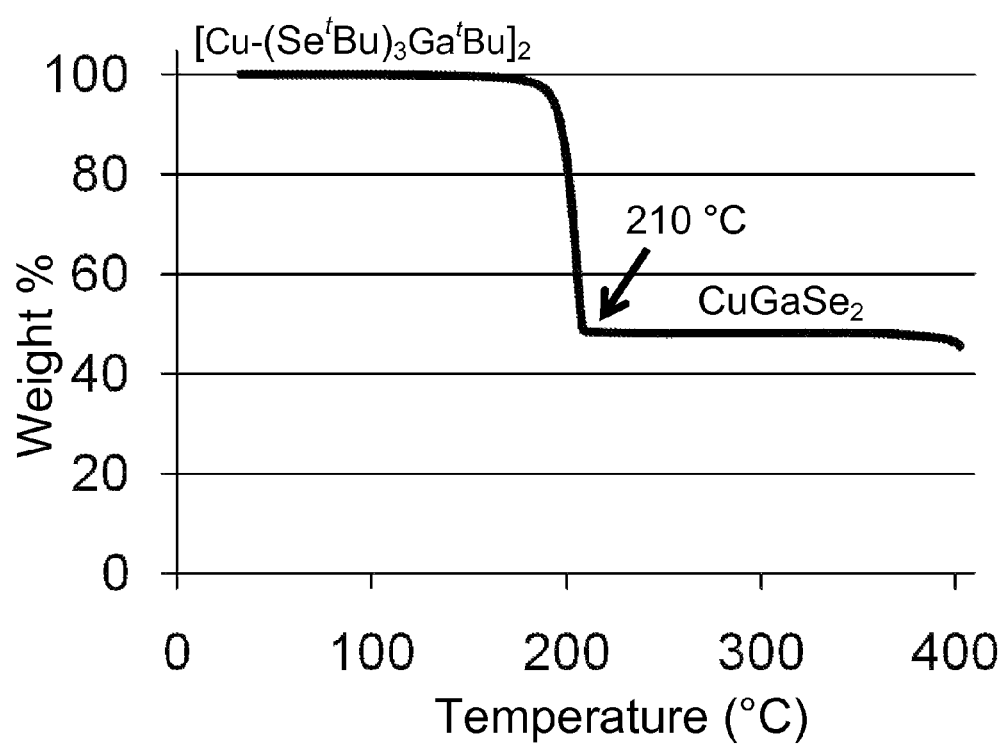
FIG. 10.

In FIG. 10 is shown the TGA for this MP1 molecular precursor. The TGA showed a single sharp transition ending at about 210° C. The yield for the transition was 48.3% (w/w), as compared to a theoretical yield for the formula CuGaSe$_2$ of 48.7% (w/w). Thus, the TGA showed that this MP1 molecular precursor can be used to prepare CuGaSe$_2$ layers and materials, and can be used as a component to prepare other semiconductor layers, crystals, and materials.

The structure of this crystalline MP1 precursor molecule was determined by single crystal X-ray diffraction. The molecular structure of the compound was of a dimer, represented by the formula (Cu—(Se$^t$Bu)$_3$Ga$^t$Bu)$_2$.

Example 6

An MP1 molecular precursor represented by the formula Cu—(S$^t$Bu)$_3$Ga$^t$Bu was synthesized using the following procedure.

Benzene (ca. 30 mL) was added to a solid mixture of CuSt$^t$Bu (0.97 g, 6.3 mmol) and $^t$Bu$_2$GaS$^t$Bu (1.73 g, 6.3 mmol) and the resulting mixture was stirred briefly at about 85° C. to produce a homogeneous solution. Tert-butylthiol (0.72 mL, 6.4 mmol) was added and the mixture was heated for about 12-14 hours at 85-90° C. to produce a pale yellow precipitate. The precipitate was isolated by filtration, washed with benzene (1×10 mL) and dried under vacuum to give 2.6 g (Yield, 90%). Elemental analysis: C, 41.4, H, 8.0, Cu, 14.3; Ga, 15.8; S, 18.8. NMR: (1H) 1.58 (9H), 1.69 (27H) in C6D6. Solubility: pentane, nil; diethyl ether, nil, benzene, ss heat; toluene, s heat.

Figure 11:
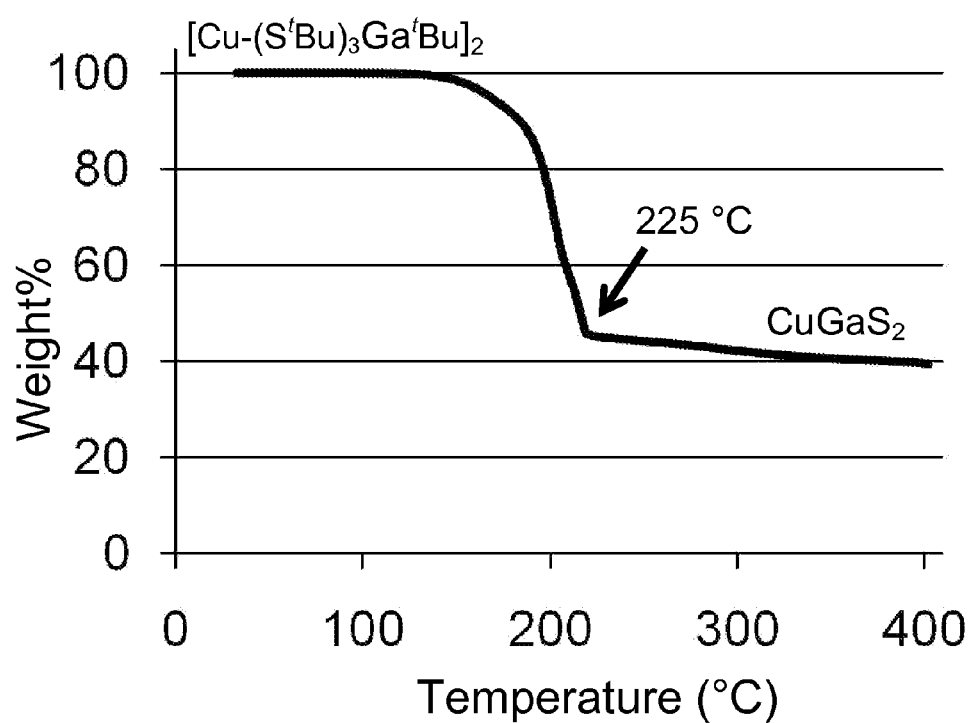
FIG. 11.

In FIG. 11 is shown the TGA for this MP1 molecular precursor. The TGA showed a single sharp transition ending at about 225° C. The yield for the transition was 45.7% (w/w), as compared to a theoretical yield for the formula CuGaS$_2$ of 43.1% (w/w). Thus, the TGA showed that this MP1 molecular precursor can be used to prepare CuGaS$_2$ layers and materials, and can be used as a component to prepare other semiconductor layers, crystals, and materials.

Example 7

An MP1 molecular precursor represented by the formula Cu—(Se$^t$Bu)$_3$In$^t$Bu was synthesized using the following procedure. Solid $^t$Bu$_2$In(Se$^t$Bu) (0.71 g, 1.9 mmol) was combined with CuSe$^t$Bu (0.31 g, 1.6 mmol) with 40 mL of toluene. $^t$BuSeH (1.9 mmol) was slowly added to the reaction mixture, and the reaction mixture was stirred at 60° C. for about 12-14 h. A pale yellow solid was formed during the reaction. This solid was collected, washed with toluene at room temperature and dried under vacuum to yield 0.55 g (Yield, 53%). Elemental analysis: C, 30.0, H, 5.4, Cu, 10.7, In, 18.9, Se, 37.2. NMR: (1H) 1.62 (s, 9H), 1.80 (s, 27H) in C6D6; 1.42 (s, 9H), 1.68 (s, 27H) in CDCl3; (13C) 32.2, 38.2 in CDCl3. Solubility: pentane, nil; diethyl ether, nil, benzene, ss heat; toluene, s heat; THF, ss; CHCl$_3$, s.

Figure 12:
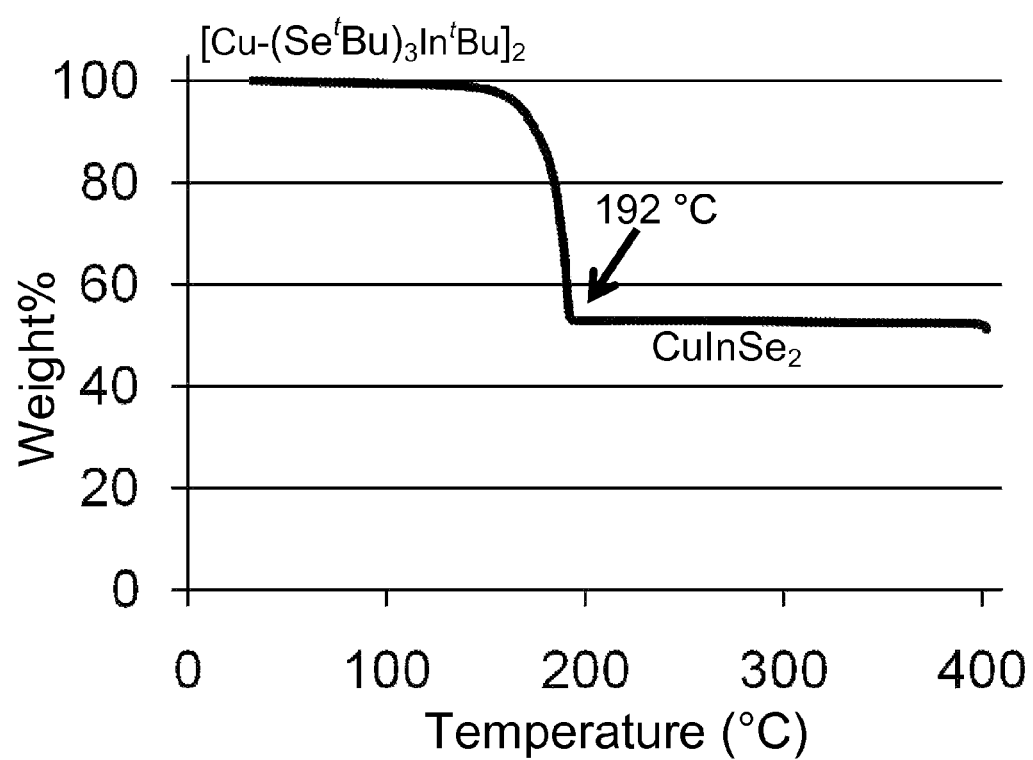
FIG. 12.

In FIG. 12 is shown the TGA for this MP1 molecular precursor. The TGA showed a single sharp transition ending at about 192° C. The yield for the transition was 53.1% (w/w), as compared to a theoretical yield for the formula CuInSe$_2$ of 52.3% (w/w). Thus, the TGA showed that this MP1 molecular precursor can be used to prepare CuInSe$_2$ layers and materials, and can be used as a component to prepare other semiconductor layers, crystals, and materials.

Example 8

An MP1 molecular precursor represented by the formula Cu—(Se$^t$Bu)$_3$In$^i$Pr was synthesized using the following procedure. $^t$BuSeH (5.9 mmol) was slowly added to a pentane solution (30 mL) of $^i$Pr$_3$In (3.9 mmol). The mixture was stirred at 25° C. for 12 h, and the solvent and excess $^t$BuSeH were removed under dynamic vacuum. Oily $^i$Pr$_2$In(Se$^t$Bu) was obtained and was combined with CuSe$^t$Bu (0.77 g, 3.9 mmol) with 40 mL of toluene. $^t$BuSeH (3.9 mmol) was slowly added to the reaction mixture, and the reaction mixture was stirred at 60° C. for about 12-14 hours. A deep red solution with suspended yellow solid was formed. The yellow solid was collected and the filtrate was concentrated to 20 mL. The yellow solid was washed with 60 mL pentane, and dried under vacuum to yield 0.6 g. Storage of the filtrate at −60° C. in a freezer afforded another 0.35 g of yellow crystals. Combined yield 35%. Elemental analysis: C, 29.1, H, 5.3, Cu, 16.5, In, 18.9, Se, 37.4. NMR: (1H) 1.52 (b, 7H, $^3J_{HH}$=7.6), 1.67 (s, 27H) in CDCl3; (13C) 23.2, 32.5, 38.0, 45.8 in CDCl3. Solubility: pentane, nil; diethyl ether, ss, benzene, s heat; toluene, vs heat; THF, s; CHCl$_3$, s.

The TGA for this MP1 molecular precursor showed a single transition having a midpoint at 192° C., ending at 199°

C. The yield for the transition was 52.1% (w/w), as compared to a theoretical yield for the formula CuInSe$_2$ of 53.4% (w/w). Thus, the TGA showed that this MP1 molecular precursor can be used to prepare CuInSe$_2$ layers and materials, and can be used as a component to prepare other semiconductor layers, crystals, and materials.

The structure of this crystalline MP1 precursor molecule was determined by single crystal X-ray diffraction. The molecular structure of the compound was of a dimer, represented by the formula (Cu—(Se$^t$Bu)$_3$In$^i$Pr)$_2$.

Example 9

An MP1 molecular precursor represented by the formula Cu—(S$^n$Bu)$_2$(S$^t$Bu)In$^t$Bu was synthesized using the following procedure. To a suspension of CuS$^t$Bu (0.43 g, 2.8 mmol) and HS$^n$Bu (0.3 mL, 5.6 mmol) in 5 mL toluene was added a solution of freshly prepared $^t$Bu$_2$InS$^n$Bu (2.8 mmol) in 5 mL toluene. The reaction mixture was heated at 80° C. for about 12-14 hours. The solvent was removed under vacuum, and the crude product was extracted with pentane. The solvent was removed under vacuum, leaving a pale yellow sticky foam (Yield, 0.40 g, 28%). NMR: (1H) 0.94 (br s, 3H); 1.50 (br s, 2H); 1.75 (s, 9H); 1.95 (br s, 2H); 3.19 (br s, 2H); (13C) 14.04 (s); 22.58 (s); 31.50 (s); 37.19 (s); 47.10 (s).

The TGA for this MP1 molecular precursor showed a single transition having a midpoint at 235° C., ending at 295° C. The yield for the transition was 47.9% (w/w), as compared to a theoretical yield for the formula CuInS$_2$ of 48.1% (w/w). Thus, the TGA showed that this MP1 molecular precursor can be used to prepare CuInS$_2$ layers and materials, and can be used as a component to prepare other semiconductor layers, crystals, and materials.

Example 10

A 75:25 molar mixture of MP1 molecular precursors represented by the formulas (Cu—(Se$^t$Bu)$_3$In$^t$Bu)$_2$ (0.190 g) and (Cu—(Se$^t$Bu)$_3$Ga$^t$Bu)$_2$ (0.060 g) was made and ground to a fine powder.

Figure 13:
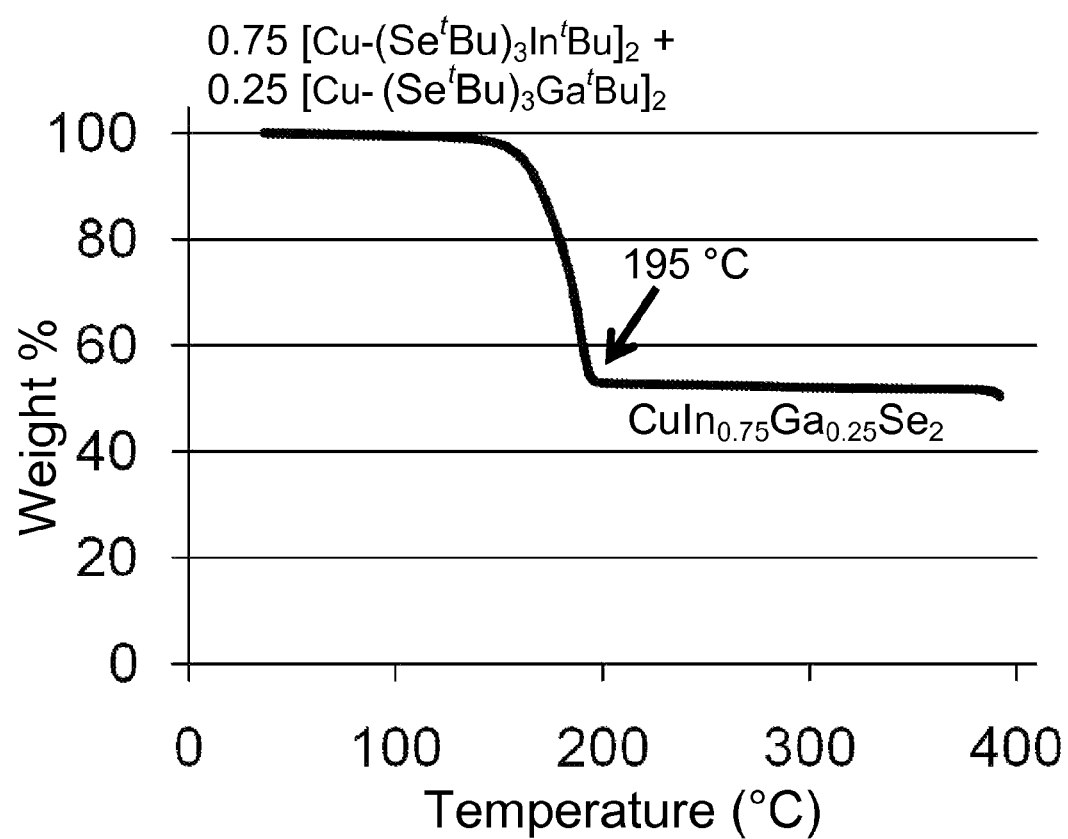
FIG. 13.

FIG. 13 shows the TGA for this mixture of MP1 molecular precursors. The TGA showed a single sharp transition ending at about 195° C. The yield for the transition was 52.9% (w/w), as compared to a theoretical yield for the formula CuIn$_{0.75}$Ga$_{0.25}$Se$_2$ of 51.4% (w/w). Thus, the TGA showed that this mixture of MP1 molecular precursors can be used to prepare CuIn$_{0.75}$Ga$_{0.25}$Se$_2$ layers and materials, and can be used as a component to prepare other semiconductor layers, crystals, and materials.

Example 11

A 50:50 molar mixture of MP1 molecular precursors represented by the formulas (Cu—(Se$^t$Bu)$_3$In$^t$Bu)$_2$ (0.100 g) and (Cu—(Se$^t$Bu)$_3$Ga$^t$Bu)$_2$ (0.093 g) was made and ground to a fine powder.

The TGA for this mixture of MP1 molecular precursors showed a single sharp transition ending at about 195° C. The yield for the transition was 51.3% (w/w), as compared to a theoretical yield for the formula CuIn$_{0.50}$Ga$_{0.50}$Se$_2$ of 50.5% (w/w). Thus, the TGA showed that this mixture of MP1 molecular precursors can be used to prepare CuIn$_{0.50}$Ga$_{0.50}$Se$_2$ layers and materials, and can be used as a component to prepare other semiconductor layers, crystals, and materials.

Example 12

An MP1 molecular precursor represented by the formula Cu—(S$^t$Bu)$_3$Ga$^i$Pr was synthesized using the following procedure. $^t$BuSH (1.0 mL, 8.8 mmol) was added to a solution of $^i$Pr$_3$Ga—OEt$_2$ (1.21 g, 4.4 mmol) in benzene (ca. 10 mL) and the resulting mixture was stirred for 1 h at about 60° C. The solvent was removed under reduced pressure giving $^i$Pr$_2$GaS$^t$Bu. CuS$^t$Bu (0.68 g, 4.4 mmol), $^t$BuSH (0.5 mL, 4.4 mmol) and benzene (ca. 15 mL) were added to the flask containing $^i$Pr$_2$GaS$^t$Bu and the mixture was heated for about 12-14 h at 85° C. to produce a pale yellow precipitate. The precipitate was isolated by filtration and dried under vacuum to give 1.6 g (Yield, 82%). NMR: (1H, C6D6) 1.61 (d, 6H), 1.66 (s, 27H).

The TGA for this MP1 molecular precursor showed a single transition ending at 220° C. The yield for the transition was 46.0% (w/w), as compared to a theoretical yield for the formula CuGaS$_2$ of 44.5% (w/w).

Example 13

An MP1 molecular precursor represented by the formula Cu—(Se$^t$Bu)$_3$Ga$^i$Pr was synthesized using the following procedure. $^t$BuSeH (1.71 mL of 3.4 M solution in Et$_2$O, 5.9 mmol) was added to a solution of $^i$Pr$_3$Ga—OEt$_2$ (1.60 g, 5.9 mmol) in benzene (ca. 10 mL) and the resulting mixture was stirred for 1 h at about 60° C. The solvent was removed under reduced pressure giving $^i$Pr$_2$GaSe$^t$Bu. CuSe$^t$Bu (1.17 g, 5.9 mmol), $^t$BuSeH (1.71 mL of 3.4 M solution in Et$_2$O, 5.9 mmol) and benzene (ca. 30 mL) were added to the flask containing $^i$Pr$_2$GaSe$^t$Bu, and the mixture was heated for about 12-14 hours at about 85° C. A tan precipitate was isolated by filtration, washed with pentane (1×30 mL) and dried under vacuum to give 2.6 g (Yield, 77%). NMR: (1H, C6D6) 1.60 (d, 6H), 1.77 (s, 27H).

Example 14

An MP1 molecular precursor represented by the formula Cu—(Se$^t$Bu)$_3$In$^s$Bu was synthesized using the following procedure. $^t$BuSeH (6.82 mmol) was slowly added to a pentane solution (30 mL) of $^s$Bu$_3$In (1.5 g, 5.2 mmol). The solution was stirred at 25° C. for 12 h. The solvent and excess $^t$BuSeH were then removed under dynamic vacuum. Oily $^s$Bu$_2$In(Se$^t$Bu) was obtained and combined with CuSe$^t$Bu (1.00 g, 5.0 mmol) and 40 mL of toluene. $^t$BuSeH (5.2 mmol) was slowly added to the reaction mixture via cannula using a Schlenk line, and the reaction mixture was stirred at 60° C. for about 12 h to afford a deep red solution. Upon cooling of the reaction mixture to 25° C., 1.32 g of pale yellow crystals were obtained. Concentration and storage of the solution at −60° C. afforded an additional 0.41 g. (Yield, 52%) NMR: (1H, C6D6) 1.25 (m, 1H), 1.67 (d, 3H, 3J$_{HH}$=6.8 Hz), 1.74 (m, 2H), 1.80 (s, 27H), 1.96 (m, 3H); (13C, C6D6) 15.5, 20.1, 30.8, 38.2, 45.7.

The TGA for this MP1 molecular precursor showed a single transition having a midpoint at 191° C., ending at 204° C. The yield for the transition was 52.3% (w/w), as compared to a theoretical yield for the formula CuInSe$_2$ of 52.3% (w/w).

Example 15

Molecular Precursor Ink Compositions

A molecular precursor ink composition is prepared in a glovebox in an inert atmosphere by dissolving an MP1 molecular precursor represented by the formula Cu—(S$^t$Bu)$_3$In$^n$Bu in toluene to a concentration of 5% (w/w). To this solution is added In(S$^n$Bu)$_3$, in an amount representing 0.1 atom-equivalents of indium relative to copper in the MP1 molecular precursor. To this solution is added 0.3% (w/w) polyurethane. Viscosity of the molecular precursor ink is determined with a SVM 3000 Viscometer (Anton Paar, Graz, Austria).

Example 16

A molecular precursor ink composition is prepared in a glovebox in an inert atmosphere by dissolving an MP1 molecular precursor represented by the formula Cu—($S^t$Bu)$_3$In$^n$Bu in decane, and heating the decane to dissolve the molecular precursor to a concentration of 5% (w/w). To this solution is added In($S^n$Bu)$_3$, in an amount representing 0.1 atom-equivalents of indium relative to copper in the MP1 molecular precursor.

Example 17

A molecular precursor ink composition is prepared in a glovebox in an inert atmosphere by dissolving two MP1 molecular precursors represented by the formulas Cu—(Se$^t$Bu)$_3$In$^n$Bu and Cu—(Se$^t$Bu)$_3$Ga$^n$Bu in acetonitrile to a total concentration of 1% (w/w). 0.75 indium-atom-equivalents of Cu—(Se$^t$Bu)$_3$In$^n$Bu are added to 0.25 gallium-atom-equivalents of Cu—(Se$^t$Bu)$_3$Ga$^t$Bu, relative to the total amount of copper.

Example 18

Molecular Precursor Compounds

A molecular precursor compound having the formula ($^i$PrIn(S$^t$Bu)$_3$-Cu)(Cu—(S$^t$Bu)$_3$Ga$^i$Pr) is prepared in an inert atmosphere using a glovebox and a Schlenk line system by reacting 0.75 equivalents of In$^i$Pr$_3$ and 0.25 equivalents of Ga$^i$Pr$_3$ with HS$^t$Bu to form $^i$Pr$_2$InS$^t$Bu and $^i$Pr$_2$GaS$^t$Bu. The products $^i$Pr$_2$InS$^t$Bu and $^i$Pr$_2$GaS$^t$Bu are contacted with a compound Cu(S$^t$Bu) in the presence of one equivalent of HS$^t$Bu to form a mixture of the MP2 molecular precursor compound ($^i$PrIn(S$^t$Bu)$_3$-Cu)(Cu—(S$^t$Bu)$_3$Ga$^i$Pr) along with other compounds.

Example 19

A molecular precursor compound having the formula ($^i$PrIn(Se$^t$Bu)$_3$-Cu)(Cu—(Se$^t$Bu)$_3$Ga$^n$Bu) is prepared in an inert atmosphere using a glovebox and a Schlenk line system by reacting 0.5 equivalents of In$^i$Pr$_3$ and 0.5 equivalents of Ga$^n$Bu$_3$ with one equivalent of HSe$^t$Bu to form $^i$Pr$_2$InSe$^t$Bu and $^n$Bu$_2$GaSe$^t$Bu. The products $^i$Pr$_2$InSe$^t$Bu and $^n$Bu$_2$GaSe$^t$Bu are contacted with one equivalent of Cu(Se$^t$Bu) in the presence of one equivalent of HSe$^t$Bu to form the MP2 molecular precursor compound ($^i$PrIn(Se$^t$Bu)$_3$-Cu)(Cu—(Se$^t$Bu)$_3$Ga$^n$Bu).

Example 20

Molecular Precursor Compounds

A molecular precursor compound having the formula ($^t$BuSe)Cu(Se$^t$Bu)$_3$In$^i$Pr is prepared in an inert atmosphere using a glovebox and a Schlenk line system by reacting In$^i$Pr$_3$ with HSe$^t$Bu to form $^i$Pr$_2$InSe$^t$Bu. The product $^i$Pr$_2$InSe$^t$Bu is contacted with a compound Cu(Se$^t$Bu)$_2$ in the presence of HSe$^t$Bu to form a molecular precursor compound.

Example 21

A molecular precursor compound having the formula ($^t$BuSe)Cu(Se$^t$Bu)$_3$Ga$^t$Bu is prepared in an inert atmosphere using a glovebox and a Schlenk line system by reacting Ga$^t$Bu$_3$ with HSe$^t$Bu to form $^t$Bu$_2$GaSe$^t$Bu. The product $^t$Bu$_2$GaSe$^t$Bu is contacted with a compound Cu(Se$^t$Bu)$_2$ in the presence of HSe$^t$Bu to form a molecular precursor compound.

Example 22

Molecular Precursor Compounds

A molecular precursor compound having the formula Cu(Se(CH$_2$)$_2$Se)(Se$^t$Bu)(Se$^t$Bu)Ga$^i$Pr is prepared in an inert atmosphere using a glovebox and a Schlenk line system by reacting Ga$^i$Pr$_3$ with (CH$_3$)$_3$SiSe(CH$_2$)$_2$SeH to form $^i$Pr$_2$GaSe(CH$_2$)$_2$SeSi(CH$_3$)$_3$. The product $^i$Pr$_2$GaSe(CH$_2$)$_2$SeSi(CH$_3$)$_3$ is contacted with a compound Cu(Se$^t$Bu)Cl in the presence of HSe$^n$Bu to form a molecular precursor compound.

Example 23

A molecular precursor compound having the formula Cu(Se(CH$_2$)$_2$SeCH$_3$)(Se$^t$Bu)$_2$In$^t$Bu is prepared in an inert atmosphere using a glovebox and a Schlenk line system by reacting In$^t$Bu$_3$ with HSe(CH$_2$)$_2$SeCH$_3$ to form $^t$Bu$_2$InSe(CH$_2$)$_2$SeCH$_3$. The product $^t$Bu$_2$InSe(CH$_2$)$_2$SeCH$_3$ is contacted with a compound Cu(Se$^t$Bu)$_2$ in the presence of one equivalent of HSe$^t$Bu to form a molecular precursor compound.

Example 24

Molecular Precursor Compounds

An MP1-Ag molecular precursor represented by the formula Ag—(Se$^t$Bu)$_3$In$^n$Bu was synthesized using the following procedure. $^t$BuSeH (4.2 mmol) was slowly added to a pentane solution (30 mL) of $^n$Bu$_3$In (1.00 g, 3.5 mmol). The reaction mixture was stirred at 25° C. for 12 h, and the solvent and excess $^t$BuSeH were removed under dynamic vacuum. A colorless oil, $^n$Bu$_2$In(Se$^t$Bu), was obtained and combined with AgSe$^t$Bu (0.76 g, 3.1 mmol) in toluene (40 mL). $^t$BuSeH (3.5 mmol) was slowly added to the reaction mixture, and the reaction mixture was stirred at 60° C. for 12-14 h. A brown solution with a small amount of black precipitate formed. This solution was filtered (black precipitate discarded), and the solvent was removed under dynamic vacuum. The remaining solid was washed with pentane (2×30 mL) and dried under dynamic vacuum. 1.26 g (52%) of white solid was obtained.

Elemental analysis: C, 28.11, H, 5.27, Ag, 15.56, In, 18.78, Se, 34.18. NMR: (1H) 0.94 (t, 3H, 3JHH=7.2 Hz), 1.34 (m, 2H), 1.47 (m, 2H), 1.67 (s, 27H), 1.75-1.81 (m, 2H) in CDCl$_3$; (13C) 13.8, 21.5, 28.0, 30.5, 38.5 and 45.2 in CDCl$_3$; (77Se) 193.4.

Figure 14:
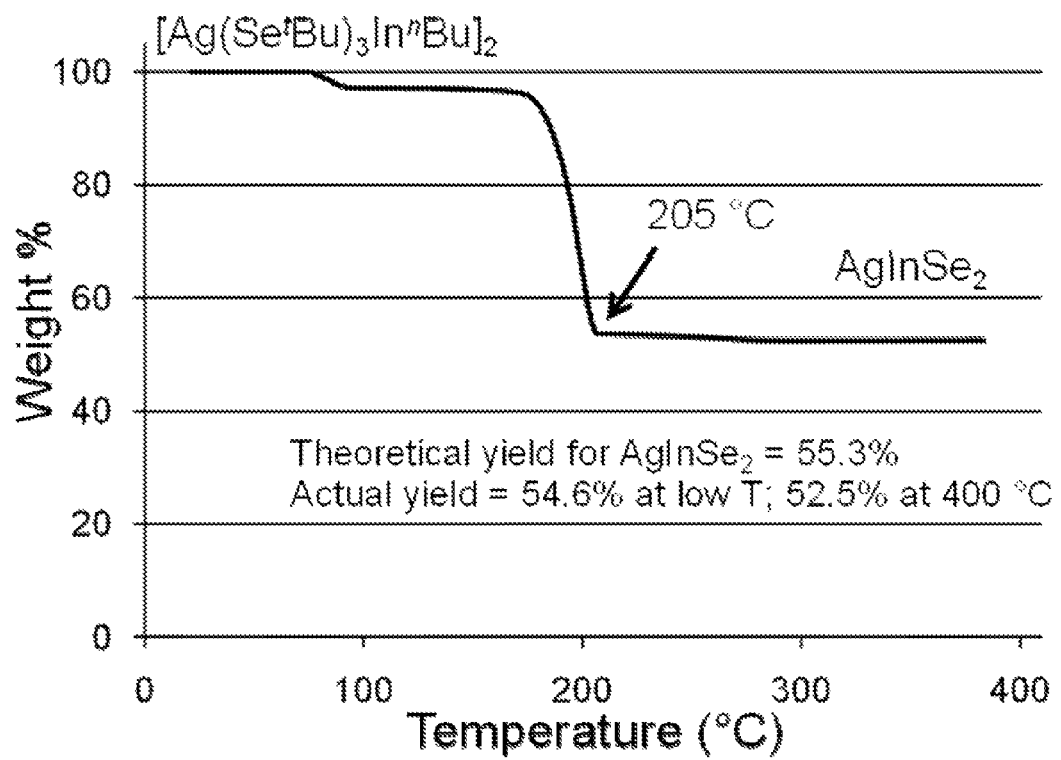
FIG. 14.

In FIG. 14 is shown the TGA for this MP1-Ag molecular precursor. The TGA for this MP1-Ag molecular precursor showed a transition ending at about 205° C. The total yield for the TGA transition was 54.6% (w/w) at about 205° C. and 52.5% at 400° C., as compared to a theoretical yield for the formula AgInSe$_2$ of 55.3% (w/w). Thus, the TGA showed that this MP1-Ag molecular precursor can be used to prepare AgInSe$_2$ layers and materials, and can be used as a component to prepare other semiconductor layers, crystals, and materials.

The unit cell of this crystalline MP1-Ag precursor molecule was determined by single crystal X-ray diffraction.

Example 25

An MP1-Ag molecular precursor represented by the formula Ag—(Se$^t$Bu)$_3$Ga$^n$Bu was synthesized using the following procedure. $^t$BuSeH (3.5 mmol) was slowly added to a pentane solution (20 mL) of $^n$Bu$_3$Ga (0.70 g, 2.9 mmol). The reaction mixture was stirred at 25° C. for 12 h, and the solvent and excess $^t$BuSeH were removed under dynamic vacuum. A colorless oil, $^n$Bu$_2$Ga(Se$^t$Bu), was obtained and combined with AgSe$^t$Bu (0.64 g, 2.6 mmol) in toluene (40 mL). $^t$BuSeH (2.9 mmol) was slowly added to the reaction mixture, and the reaction mixture was stirred at 60° C. for 12-14 h. A brown solution with a small amount of black precipitate formed. This solution was filtered (black precipitate discarded), and the solvent was removed under dynamic vacuum. The remaining solid was washed with pentane (2×30 mL) and dried under dynamic vacuum. 1.29 g (69%) of grey solid was obtained.

Elemental analysis: C, 30.42, H, 5.71, Ag, 15.84, Ga, 10.81, Se, 37.35. NMR: (1H) 0.94 (t, 3H, 3JHH=7.6 Hz), 1.18 (m, 2H), 1.43 (m, 2H), 1.65 (s, 27H), 1.86-2.18 (m, 3H) in CDCl$_3$; (13C) 13.9, 21.9, 27.5, 29.4, 37.8 and 46.1 in CDCl$_3$; (77Se) 230.4.

Figure 15:
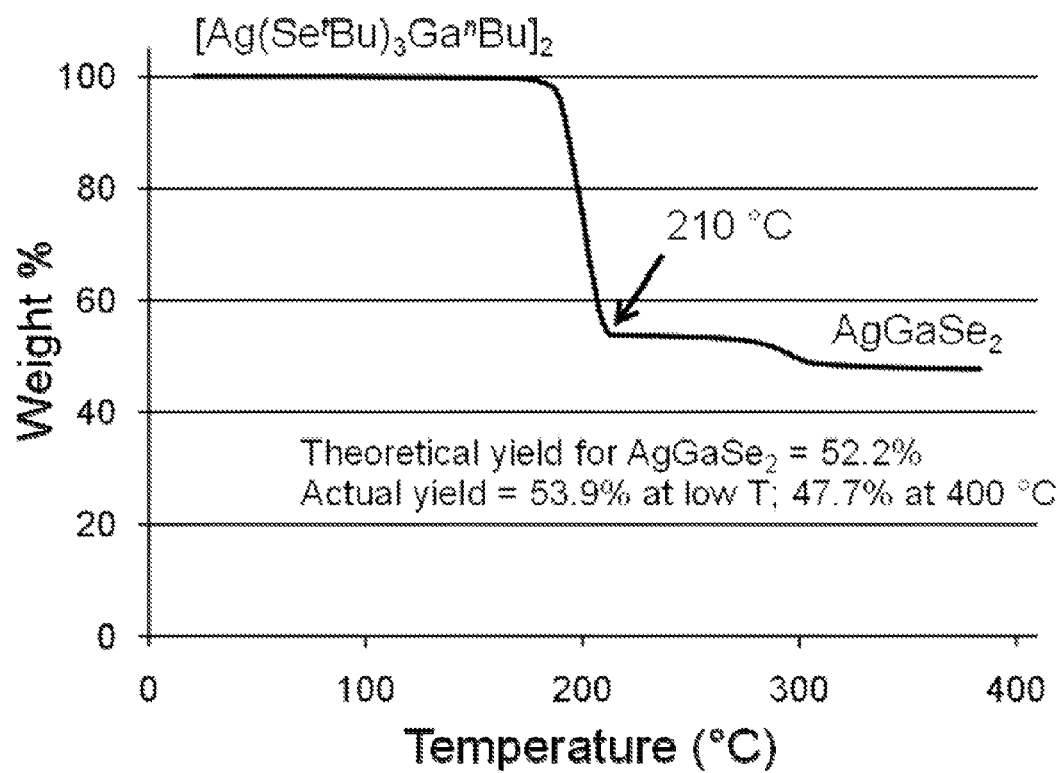
FIG. 15.

In FIG. 15 is shown the TGA for this MP1-Ag molecular precursor. The TGA for this MP1-Ag molecular precursor compound showed a transition ending at about 210° C. The yield for the transition was 53.9% (w/w) at about 210° C. and 47.7% (w/w) at about 400° C., as compared to a theoretical yield for the formula AgGaSe$_2$ of 52.2% (w/w). Thus, the TGA showed that this MP1-Ag molecular precursor can be used to prepare AgGaSe$_2$ layers and materials, and can be used as a component to prepare other semiconductor layers, crystals, and materials.

The unit cell of this crystalline MP1-Ag precursor molecule was determined by single crystal X-ray diffraction.

Example 26

An MP1-Ag molecular precursor represented by the formula Ag—(Se$^t$Bu)$_3$In$^s$Bu was synthesized using the following procedure: $^t$BuSeH (4.2 mmol) was slowly added to a pentane solution (30 mL) of $^s$Bu$_3$In (1.00 g, 3.5 mmol). The reaction mixture was stirred at 25° C. for 12 h, and the solvent and excess $^t$BuSeH were removed under dynamic vacuum. A colorless oil, $^s$Bu$_2$In(Se$^t$Bu), was obtained and part of this oil (0.5 g, 1.4 mmol) was combined with AgSe$^t$Bu (0.33 g, 1.4 mmol) in toluene (40 mL). $^t$BuSeH (1.4 mmol) was slowly added to the reaction mixture, and the reaction mixture was stirred at 60° C. for 12-14 h. A brown solution with a small amount of black precipitate formed. This solution was filtered (black precipitate discarded), and the solvent was removed under dynamic vacuum. The remaining solid was washed with pentane (2×30 mL) and dried under dynamic vacuum. 0.64 g (66%) of pale yellow solid was obtained.

Elemental analysis: C, 28.78, H, 5.30, Ag, 14.57, In, 17.67, Se, 33.28. NMR: (1H) 1.15 (t, 3H, 3JHH=7.2 Hz), 1.50 (d, 3H, 3JHH=7.2 Hz), 1.66 (s, 27H), 1.82-2.15 (m, 3H) in CDCl$_3$; (13C) 14.2, 17.2, 28.1, 30.2, 38.0 and 46.5 in CDCl$_3$; (77Se) 233.3.

Figure 16:
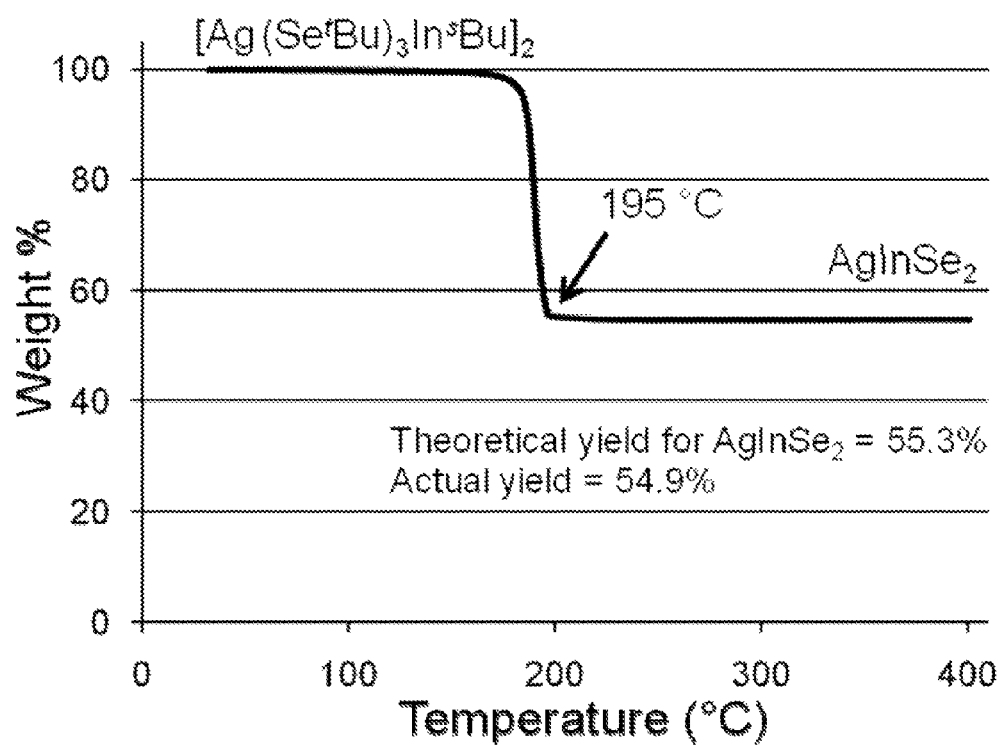
FIG. 16.

In FIG. 16 is shown the TGA for this MP1-Ag molecular precursor. The TGA for this MP1-Ag molecular precursor showed a transition ending at about 195° C. The yield for the transition was 54.9% (w/w), as compared to a theoretical yield for the formula AgInSe$_2$ of 55.3% (w/w). Thus, the TGA data showed that this MP1-Ag molecular precursor can be used to prepare AgInSe$_2$ layers and materials, and can be used as a component to prepare other semiconductor layers, crystals, and materials.

The unit cell of this crystalline MP1-Ag precursor molecule was determined by single crystal X-ray diffraction.

Example 27

An MP1-Ag molecular precursor represented by the formula Ag—(Se$^t$Bu)$_3$Ga$^s$Bu was synthesized using the following procedure: $^t$BuSeH (3.6 mmol) was slowly added to a pentane solution (20 mL) of $^s$Bu$_3$Ga (0.68 g, 2.8 mmol). The reaction mixture was stirred at 25° C. for 12 h, and the solvent and excess $^t$BuSeH were removed under dynamic vacuum. A colorless oil, $^s$Bu$_2$Ga(Se$^t$Bu), was obtained and combined with AgSe$^t$Bu (0.69 g, 2.8 mmol) in toluene (40 mL). $^t$BuSeH (2.8 mmol) was slowly added to the reaction mixture, and the reaction mixture was stirred at 60° C. for 12-14 h. A brown solution with a small amount of black precipitate formed. This solution was filtered (black precipitate discarded), and the solvent was removed under dynamic vacuum. The remaining solid was washed with pentane (2×30 mL) and dried under dynamic vacuum. 0.53 g (29%) of pale yellow solid was obtained.

Elemental analysis: C, 30.31, H, 5.71, Ag, 16.02; Ga, 10.83; Se, 35.96. NMR: (1H) 1.07 (t, 3H, 3JHH=7.2 Hz), 1.38 (d, 2H, 3JHH=6.8 Hz), 1.66 (s, 27H), 2.04-2.15 (m, 3H) in CDCl$_3$; (13C) 14.8, 17.2, 28.1, 30.2, 38.0 and 46.5 in CDCl$_3$; (77Se) 233.3.

Figure 17:
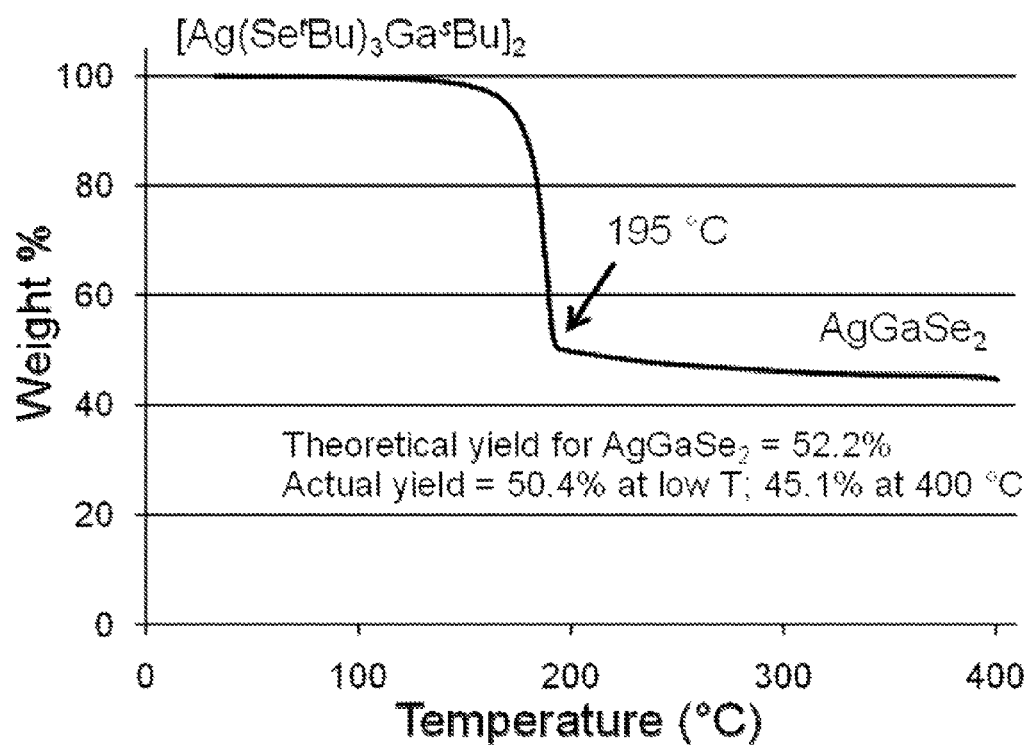
FIG. 17.

In FIG. 17 is shown the TGA for this MP1-Ag molecular precursor. The TGA showed a transition ending at about 195° C. The yield for the transition was 50.4% (w/w) at about 195° C. and 45.1% (w/w) at about 400° C., as compared to a theoretical yield for the formula AgGaSe$_2$ of 52.2% (w/w). Thus, the TGA showed that this MP1-Ag molecular precursor can be used to prepare AgGaSe$_2$ layers and materials, and can be used as a component to prepare other semiconductor layers, crystals, and materials.

The unit cell of this crystalline MP1-Ag precursor molecule was determined by single crystal X-ray diffraction.

Example 28

An MP1-Ag molecular precursor represented by the formula Ag—(Se$^t$Bu)$_3$In$^i$Pr was synthesized using the following procedure: $^t$BuSeH (4.0 mmol) was slowly added to a pentane solution (30 mL) of $^i$Pr$_3$In (0.80 g, 3.3 mmol). The reaction mixture was stirred at 25° C. for 12 h, and the solvent and excess $^t$BuSeH were removed under dynamic vacuum. 1.00 g of a colorless oil, $^i$Pr$_2$In(Se$^t$Bu), was obtained and combined with AgSe$^t$Bu (0.72 g, 3.0 mmol) in toluene (40 mL). $^t$BuSeH (3.0 mmol) was slowly added to the reaction mixture, and the reaction mixture was stirred at 60° C. for 12-14 h. A brown solution with a small amount of black precipitate formed. This solution was filtered (black precipitate discarded), and the solvent was removed under dynamic vacuum. The remaining solid was washed with pentane (2×30 mL) and dried under dynamic vacuum. 1.02 g (46%) of grey solid was obtained.

Elemental analysis: C, 26.83, H, 5.21, Ag, 14.06; In, 16.48; Se, 31.00. NMR: (1H) 1.51 (d, 6H, 3JHH=7.2 Hz), 1.67 (s, 27H), 1.74-1.83 (m, 1H) in CDCl$_3$; (13C) 23.3, 25.8, 38.7 and 45.0 in CDCl$_3$; (77Se) 193.3.

In FIG. 18 is shown the TGA for this MP1-Ag molecular precursor. The TGA showed a transition ending at about 205° C. The yield for the transition was 56.2% (w/w), as compared to a theoretical yield for the formula AgInSe$_2$ of 56.5% (w/w). Thus, the TGA showed that this MP1-Ag molecular precursor can be used to prepare AgInSe$_2$ layers and materials, and can be used as a component to prepare other semiconductor layers, crystals, and materials.

The unit cell of this crystalline MP1-Ag precursor molecule was determined by single crystal X-ray diffraction.

Example 29

Molecular Precursor Ink Compositions

A molecular precursor ink composition is prepared in a glovebox in an inert atmosphere by dissolving an MP1-Ag molecular precursor represented by the formula Ag—(Se$^t$Bu)$_3$In$^n$Bu in toluene to a concentration of 1% (w/w).

Example 30

A molecular precursor ink composition is prepared in a glovebox in an inert atmosphere by dissolving an MP1-Ag molecular precursor represented by the formula Ag—(Se$^t$Bu)$_3$In$^n$Bu in decane, and heating the decane to dissolve the molecular precursor to a concentration of 5% (w/w). To this solution is added In(Se$^n$Bu)$_3$, in an amount representing 0.1 atom-equivalents of indium relative to silver in the MP1-Ag molecular precursor.

Example 31

A molecular precursor ink composition is prepared in a glovebox in an inert atmosphere by dissolving two MP1-Ag molecular precursors represented by the formulas Ag—(Se$^t$Bu)$_3$In$^s$Bu and Ag—(Se$^t$Bu)$_3$Ga$^s$Bu in xylene to a total concentration of 10% (w/w). 0.25 indium-atom-equivalents of Ag—(Se$^t$Bu)$_3$In$^s$Bu are added to 0.75 gallium-atom-equivalents of Ag—(Se$^t$Bu)$_3$Ga$^s$Bu, relative to the total amount of silver.

Example 32

A molecular precursor ink composition is prepared in a glovebox in an inert atmosphere by slurrying an MP1-Ag molecular precursor represented by the formula Ag—(Se$^t$Bu)$_3$Ga$^t$Bu in toluene to a concentration of 8% (w/w). To this slurry is added 0.3% (w/w) polyurethane and 0.1 mol % of sodium as NaSe$^n$Bu relative to silver.

Example 33

A molecular precursor ink composition is prepared in a glovebox in an inert atmosphere by slurrying equimolar amounts of two MP1-Ag molecular precursors represented by the formulas Ag—(Se$^t$Bu)$_3$Ga$^t$Bu and Ag—(Se$^t$Bu)$_3$In$^t$Bu in heated xylene to a total concentration of 50% (w/w). To this slurry is added In(Se$^n$Bu)$_3$ and Ga(Se$^n$Bu)$_3$, in an amount representing 0.1 atom-equivalents of indium and 0.1 atom-equivalents of gallium, respectively, relative to total silver.

Example 34

A molecular precursor ink composition is prepared in a glovebox in an inert atmosphere by dissolving MP1-Ag molecular precursors Ag—(Se$^t$Bu)$_3$In$^s$Bu and Ag—(Se$^t$Bu)$_3$Ga$^s$Bu in a molar equivalent ratio of 1:3, respectively, in heated toluene to a total concentration of 10% (w/w). To this solution is added Ga(Se$^s$Bu)$_3$ in an amount representing 0.111 molar equivalents of indium relative to total copper in the slurry, so that the final ratio of the elements is Ag/Ga/In=0.90/0.77/0.23. To this solution is added 0.1 mol % of sodium as NaIn(Se$^s$Bu)$_4$ relative to silver.

Example 35

A molecular precursor ink composition is prepared in a glovebox in an inert atmosphere by mixing together MP1-Ag molecular precursors Ag—(Se$^t$Bu)$_3$In$^i$Pr and Ag—(Se$^t$Bu)$_3$Ga$^n$Bu in a molar equivalent ratio of 3:1, respectively. The mixture is dissolved in heated xylene to a total concentration of 5% (w/w). To this mixture is added In(Se$^n$Bu)$_3$ in an amount representing 0.176 molar equivalents of indium relative to total silver in the slurry, so that the final ratio of the elements is Ag/In/Ga=0.85/0.79/0.21.

Example 36

Spin Casting Deposition of a Molecular Precursor Compound

A molecular precursor ink composition is prepared according to Example 31. The molecular precursor ink is filtered with a 0.45 micron polyvinylidene difluoride (PVDF) filter. The ink is deposited onto a Mo-coated glass substrate using a spin casting unit in a glovebox in inert argon atmosphere. The substrate is spin coated with the molecular precursor ink to a film thickness of about 0.1 to 5 microns, with a SCS 6800 Spin Coater (Specialty Coating Sys., Indianapolis, Ind.).

The substrate is removed and is heated at a temperature of 400° C. in an inert atmosphere. A thin film material is produced which is a photovoltaic absorber layer.

Example 37

A molecular precursor ink composition is prepared according to Example 30. The ink is deposited onto a Mo-coated glass substrate using a spin casting unit in a glovebox in inert atmosphere. The substrate is spin coated with the molecular precursor ink to a film thickness of about 0.1 to 5 microns, with a SCS 6800 Spin Coater.

The substrate is removed and is heated at a temperature of 450° C. in an inert atmosphere. A thin film material is produced which is a photovoltaic absorber layer.

Example 38

Rod Coating a Molecular Precursor Ink Composition

A molecular precursor ink composition is prepared according to Example 34. The ink is rod coated onto a Mo-coated glass substrate using a K CONTROL COATER MODEL 201 (R K Print-Coat Instr., Litlington, UK) in a glovebox in an inert atmosphere. A film of 1 micron thickness is deposited on the substrate.

The substrate is removed and is heated at a temperature of 400° C. in an inert atmosphere. A thin film material is produced which is a photovoltaic absorber layer.

Example 39

Slot Die Coating a Molecular Precursor Ink Composition

A molecular precursor ink composition is prepared according to Example 32. The ink is slot die coated onto a polyethylene terephthalate substrate in an inert atmosphere. A film of 1.5 microns thickness is deposited on the substrate.

The substrate is removed and is heated at a temperature of 250° C. in an inert atmosphere A thin film material is produced which is a photovoltaic absorber layer.

Example 40

Screen Printing a Molecular Precursor Ink Composition

A molecular precursor ink composition is prepared according to Example 33. The molecular precursor ink is screen printed onto a Mo-coated stainless steel substrate in an inert atmosphere. A film of 2.8 microns thickness is deposited on the substrate.

The substrate is removed and is heated at a temperature of 230° C. in an inert atmosphere. A thin film material is produced which is a photovoltaic absorber layer.

Example 41

Spraying a Molecular Precursor Ink Composition

A molecular precursor ink composition is prepared according to Example 35. The molecular precursor ink is filtered with a 0.45 micron polyvinylidene difluoride (PVDF) filter. The ink is printed onto a MYLAR substrate using an M3D Aerosol Jet Deposition System (Optomec, Albuquerque) in a glovebox in an inert atmosphere. A film of 120 nm thickness is deposited on the substrate.

The substrate is removed and is heated at a temperature of 200° C. in an inert atmosphere. A thin film material is produced which is a photovoltaic absorber layer.

Example 42

Printing a Molecular Precursor Ink Composition

A molecular precursor ink composition is prepared according to Example 31. The ink is printed onto a molybdenum-coated glass substrate using a DIMATIX DMP-2831 materials printer (Fujifilm Dimatix, Lebanon, N.H.) in a glovebox in an inert atmosphere. A film of 1 micron thickness is deposited on the substrate. The substrate is removed and is heated at a temperature of 200° C. in an inert atmosphere A thin film material is produced which is a photovoltaic absorber layer.

Example 43

Spray Pyrolysis of a Molecular Precursor on a Substrate

A molecular precursor ink composition is prepared according to Example 29. The ink is sprayed onto a stainless steel substrate using a spray pyrolysis unit in a glovebox in an inert atmosphere, the spray pyrolysis unit having an ultrasonic nebulizer, precision flow meters for inert gas carrier, and a tubular quartz reactor in a furnace.

The spray-coated substrate is heated at a temperature of 250° C. in an inert atmosphere. A thin film material is produced which is a photovoltaic absorber layer.

Example 44

A molecular precursor ink composition is prepared according to Example 30. The ink is sprayed onto an aluminum substrate using a spray pyrolysis unit in a glovebox in an inert atmosphere, the spray pyrolysis unit having an ultrasonic nebulizer, precision flow meters for inert gas carrier, and a tubular quartz reactor in a furnace.

The spray-coated substrate is heated at a temperature of 250° C. in an inert atmosphere. A thin film material is produced which is a photovoltaic absorber layer.

Example 45

Preparation of a Solar Cell

A solar cell is made by depositing an electrode layer on a polyethylene terephthalate substrate. A thin film material photovoltaic absorber layer is coated onto the electrode layer according to Example 39. A CdS window layer is deposited on the absorber layer. An aluminum-doped ZnO TCO layer is deposited onto the window layer.

What is claimed is:

1. A compound comprising the formula $M^A\text{-}(ER^1)(ER^2)(ER^3)M^BR^4$, wherein $M^A$ is a monovalent metal atom, $M^B$ is an atom of Group 13, each E is independently S, Se, or Te, and $R^1$, $R^2$, $R^3$, and $R^4$ are the same or different and are independently selected from alkyl, aryl, heteroaryl, alkenyl, amido, and silyl, wherein the formula has the structure shown in one of FIG. 1 or 2.

2. The compound of claim 1, wherein $M^A$ is Cu or Ag, and $M^B$ is Ga or In.

3. The compound of claim 1, wherein each of $R^1$, $R^2$, $R^3$ and $R^4$ is independently (C1-12)alkyl.

4. The compound of claim 1, wherein each of $R^1$, $R^2$, $R^3$ and $R^4$ is independently (C1-4)alkyl.

5. The compound of claim 1, wherein the compound is crystalline.

6. The compound of claim 1, wherein the compound is a liquid at 25° C.

7. The compound of claim 1, wherein the compound is a dimer having the formula $(M^A\text{-}(ER^1)(ER^2)(ER^3)M^BR^4)_2$.

8. The compound of claim 1, wherein the compound has the formula $(M^{A1}\text{-}(ER^1)(ER^2)(ER^3)M^BR^4)(M^{A2}\text{-}(ER^1)(ER^2)(ER^3)M^BR^4)$, wherein $M^{A1}$ and $M^{A2}$ are different monovalent metal atoms.

9. A compound having the formula $Z\text{-}M^A\text{-}(ER^1)(ER^2)(ER^3)M^BR^4$, wherein $M^A$ is a divalent metal atom, Z is selected from alkyl, aryl, heteroaryl, alkenyl, amido, -ER and silyl, $M^B$ is an atom of Group 13, each E is independently S, Se, or Te, and $R^1$, $R^2$, $R^3$, and $R^4$ are the same or different and are independently selected from alkyl, aryl, heteroaryl, alkenyl, amido, and silyl, wherein R is alkyl or aryl and the formula has the structure shown in one of FIGS. 3 and 4.

10. A compound having the formula $M^A(ER^1Z)(ER^2)(ER^3)M^BR^4$, wherein Z is attached to $M^A$ and Z is a neutral moiety selected from —NR$_2$, —PR$_2$, —AsR$_2$, -ER, —SR, —OR, and —SeR, where R is alkyl or aryl, $M^B$ is an atom of Group 13, each E is independently S, Se, or Te, and $R^1$, $R^2$, $R^3$, and $R^4$ are the same or different and are independently selected from alkyl, aryl, heteroaryl, alkenyl, amido, and silyl, wherein the formula has the structure shown in FIG. 5.

11. The compound of claim 10, wherein Z is an anionic moiety selected from —NR$^-$, -E$^-$, —O$^-$, —R$^-$, -ERNR$^-$, -ERE$^-$, and —SiR$_2^-$, where R is alkyl or aryl.

12. The compound of claim 1, wherein the compound has any one of the formulas Cu—(S$^t$Bu)$_3$In$^i$Pr; Cu—(S$^t$Bu)$_3$In$^n$Bu; Cu—(S$^t$Bu)$_3$In$^n$Bu; Cu—(S$^t$Bu)$_3$In$^t$Bu; Cu—(Se$^t$Bu)$_3$Ga$^t$Bu; Cu—(Se$^t$Bu)$_3$Ga$^t$Bu; Cu—(Se$^t$Bu)$_3$In$^t$Bu; Cu—(Se$^t$Bu)$_3$In$^i$Pr; Cu—(Se$^t$Bu)$_3$In$^s$Bu; Cu—(Se$^t$Bu)$_3$Ga$^i$Pr; Au—(S$^t$Bu)$_3$In$^i$Pr; Ag—(S$^t$Bu)$_3$In$^n$Bu; Hg—(Se$^t$Bu)$_3$ Ga$^t$Bu; Cu—(S″Bu)$_2$(S$^t$Bu)In$^t$Bu; Cu—(S$^t$Bu)$_2$(S″Bu)In$^i$Pr; Cu—(S$^t$Bu)$_2$(S$^i$Pr)In″Bu; Cu—(S$^t$Bu)$_2$(Se$^i$Pr)In$^i$Pr; Cu-(Te$^t$Bu)$_2$(Se$^i$Pr)In″Bu; Cu—(Se$^t$Bu)$_2$(Te$^i$Pr)In″Bu; Cu—(S$^t$Bu)$_2$(Te$^i$Pr)In$^t$Bu; Cu—(S$^t$Bu)(S$^i$Pr)(S″Bu)In$^t$Pr; Cu—(Se$^t$Bu)(S$^i$Pr)(S″Bu)In″Bu; Cu—(S$^t$Bu)(S$^i$Pr)(Te″Bu)In$^t$Bu; Cu—(S$^t$Bu)(Se$^i$Pr)(Se″Bu)In$^i$Pr; Cu—(S$^t$Bu)$_3$In(n-octyl); Cu—(S$^t$Bu)$_3$In(n-dodecyl); Cu—(S$^t$Bu)$_3$In(branched-C18); Cu—(S$^t$Bu)$_3$In(branched-C22); Cu—(Se(n-hexyl))$_3$Ga$^t$Bu; Cu—(S(n-octyl))$_3$Ga$^t$Bu; and a dimer of any of the foregoing.

13. The compound of claim 1, wherein the compound has any one of the formulas: ($^i$PrIn(S$^t$Bu)$_3$-Cu)(Cu—(S$^t$Bu)$_3$Ga$^i$Pr); (″BuIn(S$^t$Bu)$_3$-Cu)(Cu—(S$^t$Bu)$_3$Ga″Bu); (″BuGa(Se$^t$Bu)$_3$-Cu)(Cu—(Se$^t$Bu)$_3$Tl$^t$Bu); ($^t$BuIn(S$^t$Bu)$_3$-Cu)(Cu—(S$^t$Bu)$_3$Ga$^t$Bu); ($^t$BuTl(Se$^t$Bu)$_3$-Cu)(Cu—(Se$^t$Bu)$_3$Ga$^t$Bu); ($^t$BuGa(S$^t$Bu)$_3$-Cu)(Cu—(S$^t$Bu)$_3$In$^t$Bu); ($^t$BuIn(Se$^t$Bu)$_3$-Cu)(Cu—(Se$^t$Bu)$_3$Ga$^t$Bu); and ($^i$PrIn(Se$^t$Bu)$_3$-Cu)(Cu—(Se$^t$Bu)$_3$Ga$^i$Pr), ($^i$PrIn(S$^t$Bu)$_3$-Cu)(Ag—(S$^t$Bu)$_3$Ga$^i$Pr); (″BuIn(S$^t$Bu)$_3$-Cu)(Au—(S$^t$Bu)$_3$Ga$^t$Bu); (″BuGa(Se$^t$Bu)$_3$-Cu)(Ag—(Se$^t$Bu)$_3$Tl$^t$Bu); ($^t$BuIn(S$^t$Bu)$_3$-Cu)(Au—(S$^t$Bu)$_3$Ga$^t$Bu); ($^t$BuTl(Se$^t$Bu)$_3$-Cu)(Ag—(Se$^t$Bu)$_3$Ga$^t$Bu); ($^t$BuGa(S$^t$Bu)$_3$-Cu)(Au—(S$^t$Bu)$_3$In$^t$Bu); ($^t$BuIn(Se$^t$Bu)$_3$-Cu)(Ag—(Se$^t$Bu)$_3$Ga$^t$Bu); ($^i$PrIn(Se$^t$Bu)$_3$-Cu)(Au—(Se$^t$Bu)$_3$Ga$^i$Pr), ($^i$PrGa(S$^t$Bu)$_3$-Au)(Au—(S$^t$Bu)$_3$In$^i$Pr); (″BuGa(S$^t$Bu)$_3$-Ag)(Ag—(S$^t$Bu)$_3$In″Bu); and ($^t$BuTl(Se$^t$Bu)$_3$-Hg)(Hg—(Se$^t$Bu)$_3$In$^t$Bu), ($^i$PrIn(S″Bu)(S$^t$Bu)$_2$-Cu)(Cu—(S$^t$Bu)$_2$(S″Bu)Ga$^i$Pr); (″BuIn(S$^i$Pr)(S$^t$Bu)$_2$-Cu)(Cu—(S$^t$Bu)$_2$(S$^i$Pr)Ga″Bu); ($^i$PrTl(Se$^i$Pr)(S$^t$Bu)$_2$-Cu)(Cu—(S$^t$Bu)$_2$(Se$^i$Pr)Ga$^i$Pr); (″BuGa(Se$^i$Pr)(Te$^t$Bu)$_2$-Cu)(Cu-(Te$^t$Bu)$_2$(Se$^i$Pr)In″Bu); (″BuTl(Te$^i$Pr)(Se$^t$Bu)$_2$-Cu)(Cu—(Se$^t$Bu)$_2$(Te$^i$Pr)In″Bu); ($^t$BuGa(Te$^i$Pr)(S$^t$Bu)$_2$-Cu)(Cu—(S$^t$Bu)$_2$(Te$^i$Pr)In$^t$Bu), ($^i$PrIn(S″Bu)(S$^i$Pr)(S$^t$Bu)—Cu)(Cu—(S$^t$Bu)(S$^i$Pr)(S″Bu)Ga$^i$Pr); (″BuIn(S″Bu)(S$^i$Pr)(Se$^t$Bu)—Cu)(Cu—(Se$^t$Bu)(S$^i$Pr)(S″Bu)Tl$^t$Bu); ($^t$BuGa(Te$^t$Bu)(S$^i$Pr)(Se$^t$Bu)—Cu)(Cu—(Se$^t$Bu)(S$^i$Pr)(Te″Bu)In$^t$Bu); ($^i$PrGa(Se″Bu)(Se$^i$Pr)(Se″Bu)—Cu)(Cu—(Se″Bu)(Se$^i$Pr)(Se″Bu)Tl$^i$Pr), ((n-octyl)In(S$^t$Bu)$_3$-Cu)(Cu—(S$^t$Bu)$_3$Ga(n-octyl)); ((n-dodecyl)In(S$^t$Bu)$_3$-Cu)(Cu—(S$^t$Bu)$_3$Ga(n-dodecyl)); ((branched-C18)Ga(S$^t$Bu)$_3$-Cu)(Cu—(Se$^t$Bu)$_3$In(branched-C18)); ((branched-C22)In(S$^t$Bu)$_3$-Cu)(Cu—(S$^t$Bu)$_3$Tl(branched-C22)); ($^t$BuTl(Se(n-hexyl))$_3$-Cu)(Cu—(Se(n-hexyl))$_3$In$^t$Bu); and ($^t$BuGa(Se(n-octyl))$_3$-Cu)(Cu—(Se(n-octyl))$_3$Tl$^t$Bu).

14. The compound of claim 9, wherein the compound has any one of the formulas: ($^t$BuS)Cu(S$^t$Bu)$_3$In$^i$Pr; ($^t$BuS)Cu(S$^t$Bu)$_3$In″Bu; ($^t$BuSe)Cu(S$^t$Bu)$_3$In″Bu; ($^t$BuS)Cu(S$^t$Bu)$_3$In$^t$Bu; ($^t$BuSe)Cu(Se$^t$Bu)$_3$Ga$^t$Bu; ($^t$BuS)Cu(S$^t$Bu)$_3$Ga$^t$Bu; ($^t$BuSe)Cu(Se$^t$Bu)$_3$In$^t$Bu; ($^t$BuSe)Cu(Se$^t$Bu)$_3$In$^i$Pr, ($^t$BuS)Cu(S$^t$Bu)$_3$Ga$^i$Pr; ($^t$BuS)Cu(S$^t$Bu)$_3$Tl$^i$Pr; ($^t$BuSe)Cu(Se$^t$Bu)$_3$Ga″Bu; ($^t$BuS)Cu(S$^t$Bu)$_3$Ga$^t$Bu; ($^t$BuSe)Cu(S$^t$Bu)$_3$Tl$^t$Bu; ($^t$BuSe)Cu(Se$^t$Bu)$_3$Ga$^i$Pr, ($^t$BuS)Zn(S$^t$Bu)$_3$In$^i$Pr; ($^t$BuSe)Hg(Se$^t$Bu)$_3$Ga$^t$Bu; ($^t$BuS)Cd(S$^t$Bu)$_3$In$^i$Pr; ($^t$BuS)V(S$^t$Bu)$_3$In″Bu; ($^t$BuS)Cu(S$^t$Bu)$_2$(S″Bu)In$^i$Pr; ($^t$BuS)Cu(S$^t$Bu)$_2$(S$^i$Pr)In″Bu; ($^t$BuS)Cu(S$^t$Bu)$_2$(Se$^i$Pr)In$^i$Pr; ($^t$BuTe)Cu(Te$^t$Bu)$_2$(Se$^i$Pr)In″Bu; ($^t$BuSe)Cu(Se$^t$Bu)$_2$(Te$^i$Pr)In″Bu; ($^t$BuS)Cu(S$^t$Bu)$_2$(Te$^i$Pr)In$^t$Bu, (″BuS)Cu(S$^t$Bu)(S$^i$Pr)(S″Bu)In$^t$Pr; (″BuS)Cu(Se$^t$Bu)(S$^i$Pr)(S″Bu)In″Bu; ($^i$PrS)Cu(Se$^t$Bu)(S$^i$Pr)(Te″Bu)In$^t$Bu; ($^i$PrSe)Cu(Se$^t$Bu)(Se$^i$Pr)(Se″Bu)In$^i$Pr, ($^t$BuS)Cu(S$^t$Bu)$_3$In(n-octyl); ($^t$BuS)Cu(S$^t$Bu)$_3$In(n-dodecyl); ($^t$BuSe)Cu(Se$^t$Bu)$_3$In(branched-C18); ($^t$BuS)Cu(S$^t$Bu)$_3$In(branched-C22); ((n-hexyl)Se)Cu(Se(n-hexyl))$_3$Ga$^t$Bu; ((n-octyl)S)Cu(S(n-octyl))$_3$Ga$^t$Bu, (″BuS)Cu(S$^t$Bu)$_3$In$^t$Bu; (″BuS)Cu(S$^t$Bu)$_3$In″Bu; ($^i$PrSe)Cu(Se$^t$Bu)$_3$In″Bu; ($^i$PrS)Cu(S$^t$Bu)$_3$In$^t$Bu; (″BuSe)Cu(Se$^t$Bu)$_3$Ga$^t$Bu; ($^i$PrS)Cu(S$^t$Bu)$_3$Ga$^t$Bu; (″BuSe)Cu(Se$^t$Bu)$_3$In$^t$Bu; ($^i$PrSe)Cu(Se$^t$Bu)$_3$In$^i$Pr, $^t$BuCu(S$^t$Bu)$_3$In$^i$Pr; $^t$BuZn(S$^t$Bu)$_3$In″Bu; $^t$BuZn(Se$^t$Bu)$_3$In$^t$Bu; $^t$BuZn(S$^t$Bu)$_3$In$^t$Bu; $^t$BuZn(Se$^t$Bu)$_3$Ga$^t$Bu; $^t$BuZn(S$^t$Bu)$_3$Ga$^t$Bu; $^t$BuZn(Se$^t$Bu)$_3$In$^t$Bu; $^t$BuCu(Se$^t$Bu)$_3$In$^i$Pr, $^t$BuZn(S$^t$Bu)$_3$In$^i$Pr; $^t$BuHg(Se$^t$Bu)$_3$Ga$^t$Bu; $^t$BuCd(S$^t$Bu)$_3$In$^i$Pr.

15. The compound of claim 10, wherein the compound has any one of the formulas: Cu(S(CH$_2$)$_2$Se)(S$^t$Bu)(S″Bu)In$^i$Pr; Cu(S(CH$_2$)$_2$Se)(S$^t$Bu)(S″Bu)In″Bu; Cu(Se(CH$_2$)$_2$NEt)(Se$^t$Bu)(Se″Bu)In″Bu; Cu(Se(CH$_2$)$_2$NMe)(Se$^t$Bu)(Se″Bu)In$^t$Bu; Cu(Se(CH$_2$)$_2$N(Phenyl))(Se$^t$Bu)(Se″Bu)Ga$^t$Bu; Cu(Se(CH$_2$)$_2$N$^t$Bu)(Se$^t$Bu)$_2$Ga$^t$Bu; Cu(Se(CH$_2$)$_2$Se)(Se$^t$Bu)(Se″Bu)In$^t$Bu; Cu(Se(CH$_2$)$_2$Se)(Se$^t$Bu)$_2$In$^i$Pr, Cu(S(CH$_2$)$_2$N$^t$Bu)(S$^t$Bu)(S″Bu)Ga$^i$Pr; Cu(S(CH$_2$)$_2$N$^i$Pr)(S$^t$Bu)(S″Bu)Tl$^t$Bu; Cu(Se(CH$_2$)$_2$N$^t$Bu)(S$^t$Bu)(S″Bu)Ga$^t$Bu; Cu(S(CH$_2$)$_2$N$^i$Pr)(S$^t$Bu)(S″Bu)Tl$^t$Bu; Cu(Se(CH$_2$)$_2$N$^t$Bu)(S$^t$Bu)(S″Bu)Tl$^t$Bu; Cu(Se(CH$_2$)$_2$N$^i$Pr)(S$^t$Bu)(S″Bu)Ga$^i$Pr, Cu(Se(CH$_2$)$_3$$^-$)(S$^t$Bu)$_2$In$^t$Bu, Cu(Se$^i$Pr)(S$^t$Bu)$_2$In$^t$Bu, Zn(S(CH$_2$)$_2$N$^t$Bu)(S$^t$Bu)(S″Bu)In$^i$Pr; Cd(S(CH$_2$)$_2$S)(S$^t$Bu)(S″Bu)In″Bu; Hg(S(CH$_2$)$_2$N$^i$Pr)(S$^t$Bu)(S″Bu)Ga$^t$Bu, Cu(S(CH$_2$)$_2$N$^t$Bu$_2$)$_2$(S″Bu)In$^i$Pr; Cu(S(CH$_2$)$_2$N$^t$Bu$_2$)$_2$(S$^i$Pr)In″Bu; Cu(S(CH$_2$)$_2$SR)$_2$(Se$^i$Pr)In$^i$Pr; Cu(Te(CH$_2$)$_2$SeR)$_2$(Se$^i$Pr)In″Bu; Cu(Se(CH$_2$)$_2$SeR)$_2$(Te$^i$Pr)In″Bu; Cu(S(CH$_2$)$_2$SeR)$_2$(Te$^i$Pr)In$^t$Bu, Au(S(CH$_2$)$_2$N$^i$Pr$_2$)$_2$(S″Bu)In$^i$Pr; Ag(S(CH$_2$)$_2$N$^t$Bu$_2$)$_2$(S$^i$Pr)In″Bu; Hg(S(CH$_2$)$_2$SR)$_2$(Se$^i$Pr)In$^i$Pr; Au(Te(CH$_2$)$_2$SeR)$_2$(Se$^i$Pr)In″Bu; Cu(Se(CH$_2$)$_2$SeR)$_2$(Te$^i$Pr)In″Bu; Cu(S(CH$_2$)$_2$SeR)$_2$(Te$^i$Pr)In$^t$Bu, Cu(S(CH$_2$)$_2$N$^t$Bu$_2$)(S$^i$Pr)(S″Bu)In$^i$Pr; Cu(Se(CH$_2$)$_2$SeR)(S$^i$Pr)(S″Bu)In″Bu; Cu(Se(CH$_2$)$_2$SR)(S$^i$Pr)(Te″Bu)In$^t$Bu; Cu(Se(CH$_2$)$_2$N$^i$Pr$_2$)(Se$^i$Pr)(Se″Bu)In$^i$Pr, Cu(S(CH$_2$)$_2$N$^t$Bu$_2$)$_3$In(n-octyl); Cu(S(CH$_2$)$_2$SeR)$_3$In(n-dodecyl); Cu(Se(CH$_2$)$_2$SeR)$_3$In(branched-C18); and Cu(S(CH$_2$)$_2$N$^t$Bu$_2$)$_3$In(branched-C22).

16. The compound of claim 1, wherein the compound has any one of the formulas: Ag—(S$^t$Bu)$_3$In$^i$Pr; Ag—(S$^t$Bu)$_3$In″Bu; Ag—(Se$^t$Bu)$_3$In″Bu; Ag—(S$^t$Bu)$_3$In$^t$Bu; Ag—(Se$^t$Bu)$_3$Ga$^t$Bu; Ag—(Se$^t$Bu)$_3$Ga$^s$Bu; Ag—(Se$^t$Bu)$_3$Ga$^t$Bu; Ag—(S$^t$Bu)$_3$Ga$^t$Bu; Ag—(Se$^t$Bu)$_3$In$^t$Bu; Ag—(Se$^t$Bu)$_3$In$^i$Pr; Ag—(Se$^t$Bu)$_3$In$^s$Bu; Ag—(Se$^t$Bu)$_3$Ga$^i$Pr; Ag—(S$^t$Bu)$_3$Ga$^i$Pr; Ag—(S$^t$Bu)$_3$Tl$^i$Pr; Ag—(S$^t$Bu)$_3$Tl″Bu; Ag—(Se$^t$Bu)$_3$Tl″Bu; Ag—(S$^t$Bu)$_3$Tl$^t$Bu; Ag—(Se$^t$Bu)$_3$Tl$^t$Bu; Ag—(Se$^t$Bu)$_3$Tl$^i$Pr; Ag—(S″Bu)$_2$(S$^t$Bu)In$^t$Bu; Ag—(S$^t$Bu)$_2$(S″Bu)In$^i$Pr; Ag—(S$^t$Bu)$_2$(S$^i$Pr)In″Bu; Ag—(S$^t$Bu)$_2$(Se$^i$Pr)In$^i$Pr; Ag-(Te$^t$Bu)$_2$(Se$^i$Pr)In″Bu; Ag—(Se$^t$Bu)$_2$(Te$^i$Pr)In″Bu; Ag—(S$^t$Bu)$_2$(Te$^i$Pr)In$^t$Bu; Ag—(S$^t$Bu)(S$^i$Pr)(S″Bu)In$^i$Pr; Ag—(Se$^t$Bu)(S$^i$Pr)(S″Bu)In″Bu; Ag—(Se$^t$Bu)(S$^i$Pr)(Te″Bu)In$^t$Bu; Ag—(Se$^t$Bu)(Se$^i$Pr)(Se″Bu)In$^i$Pr; Ag—(S$^t$Bu)$_3$In(n-octyl); Ag—(S$^t$Bu)$_3$In(n-dodecyl); Ag—(Se$^t$Bu)$_3$In(branched-C18); Ag—(S$^t$Bu)$_3$In(branched-C22); Ag—(Se(n-hexyl))$_3$Ga$^t$Bu; Ag—(S(n-octyl))$_3$Ga$^t$Bu; and a dimer of any of the foregoing.

17. An ink comprising a compound of claim 1 and a carrier.

18. The ink of claim 17, wherein the ink is a solution or suspension of the compound in an organic carrier.

19. The ink of claim 17, further comprising one or more components selected from the group of a surfactant, a dispersant, an emulsifier, an anti-foaming agent, a dryer, a filler, a resin binder, a thickener, a viscosity modifier, an anti-oxidant, a flow agent, a plasticizer, a conductivity agent, a crystallization promoter, an extender, a film conditioner, an adhesion promoter, and a dye.

20. The ink of claim 17, further comprising one or more components selected from the group of an additional indium-containing compound, an additional gallium-containing compound, a molybdenum-containing compound, a conducting polymer, copper metal, indium metal, gallium metal, zinc metal, an alkali metal, an alkali metal salt, an alkaline earth metal salt, a sodium chalcogenate, a calcium chalcogenate, cadmium sulfide, cadmium selenide, cadmium telluride, indium sulfide, indium selenide, indium telluride, gallium sulfide, gallium selenide, gallium telluride, zinc sulfide, zinc selenide, zinc telluride, copper sulfide, copper selenide, copper telluride, molybdenum sulfide, molybdenum selenide, molybdenum telluride, and mixtures of any of the foregoing.

\* \* \* \* \*